(12) United States Patent
Blumberg et al.

(10) Patent No.: US 10,626,175 B2
(45) Date of Patent: Apr. 21, 2020

(54) HUMANIZED AFFINITY MATURED ANTI-FCRN ANTIBODIES

(71) Applicant: Syntimmune, Inc., Boston, MA (US)

(72) Inventors: Laurence J. Blumberg, New York, NY (US); Richard S. Blumberg, Weston, MA (US); Susan Dana Jones, Boston, MA (US); Derry Roopenian, Salsbury Cove, ME (US); Robert George Edward Holgate, Royston (GB); Timothy David Jones, Cambridge (GB); Arron Robert Hearn, Ely (GB)

(73) Assignee: SYNTIMMUNE, INC., Boston, MA (US)

( * ) Notice: Subject to any disclaimer, the term of this patent is extended or adjusted under 35 U.S.C. 154(b) by 155 days.

(21) Appl. No.: 15/811,218

(22) Filed: Nov. 13, 2017

(65) Prior Publication Data

US 2018/0291101 A1    Oct. 11, 2018

Related U.S. Application Data

(63) Continuation-in-part of application No. PCT/US2016/032168, filed on May 12, 2016.

(60) Provisional application No. 62/160,423, filed on May 12, 2015, provisional application No. 62/217,490, filed on Nov. 9, 2015.

(51) Int. Cl.
C07K 16/18 (2006.01)
C07K 16/28 (2006.01)
A61K 39/395 (2006.01)

(52) U.S. Cl.
CPC ........ *C07K 16/2803* (2013.01); *A61K 39/395* (2013.01); *C07K 16/283* (2013.01); *C07K 2317/24* (2013.01); *C07K 2317/56* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2006/0031954 A1 | 2/2006 | Roopenian |
| 2011/0212087 A1 | 9/2011 | Strohl et al. |
| 2014/0328841 A1 | 11/2014 | Blumberg et al. |

FOREIGN PATENT DOCUMENTS

| | | |
|---|---|---|
| WO | 2005/013912 A2 | 2/2005 |
| WO | 2006/118772 A2 | 11/2006 |
| WO | 2007/087289 A2 | 8/2007 |
| WO | 2014/019727 A1 | 2/2014 |

OTHER PUBLICATIONS

Christianson, G. J. et al., "Monoclonal antibodies directed against human FcRn and their applications", mAbs (2012); vol. 4(2); pp. 208-16.
Aldevron Online Antibody Catalog, Oct. 22, 2014 [https://web.archive.org/web/20141022043305/http:/www.aldevron.com/products/antibodies/](website crawled on Oct. 22, 2014 at 4:33 am and 5 seconds), and embedded hyperlinks therein to PDF Data Sheets for FcRN-ADM31 and FcRN-DVN24. [DVN24 is the mouse monoclonal antibody referenced at [00202] of the instant application.].
Liu, L. et al., "Amelioration of Experimental Autoimmune Myasthenia Gravis in Rats by Nenatal FcR Blockade"; Journal of Immunology (2007); vol. 178:8, pp. 5390-5398.
Abdiche, Y. N. et al., "The Neonatal Fc Receptor (FcRn) binds independently to Both Sides of the IgG Homodimer with Identical Affinity", mAbs (2015); vol. 7:2; pp. 331-343.
Nixon, A. E., et al., "Fully Human Monoclonal Antibody Inhibitors of the Neonatal Fc Receptor Reduce Circulating IcG in Non-Humans Primates"; Front. In Immol. (2015); vol. 6:176; pp. 1-13.

*Primary Examiner* — Michael D Pak
(74) *Attorney, Agent, or Firm* — Fox Rothschild LLP

(57) ABSTRACT

Provided herein are recombinant antibodies and antigen-binding portions thereof useful for binding to FcRn and blocking binding of FcRn to IgG Fc. The FcRn-binding proteins can be used to treat a variety of disorders including autoimmune disorders.

2 Claims, 18 Drawing Sheets

Specification includes a Sequence Listing.

| Kabat No. | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 1 0 | 1 | 2 | 3 | 4 | 5 | 6 | 7 | 8 | 9 | 2 0 | 1 | 2 | 3 | 4 | 5 | 6 | 7 | 8 | 9 | 3 0 | 1 | 2 | 3 | 4 | 5 | 6 | 7 | 8 | 9 | 4 0 | 1 | 2 | 3 |
| VH1 | Q | V | Q | L | V | Q | S | G | A | E | L | K | K | P | G | A | S | V | K | L | S | C | K | A | S | G | Y | T | F | T | X | X | X | X | X | W | V | K | Q | A | T | G | Q |
| VH2 | Q | V | Q | L | V | Q | S | G | A | E | V | K | K | P | G | A | S | V | K | V | S | C | K | A | S | G | Y | T | F | T | X | X | X | X | X | W | V | R | Q | A | P | G | Q |
| VH3 | Q | V | Q | L | V | Q | S | G | A | E | V | K | K | P | G | A | S | V | K | V | S | C | K | A | S | G | Y | T | F | T | X | X | X | X | X | W | V | R | Q | A | P | G | Q |
| VH4 | Q | V | Q | L | V | Q | S | G | A | E | V | K | K | P | G | A | S | V | K | V | S | C | K | A | S | G | Y | T | F | T | X | X | X | X | X | W | V | R | Q | A | P | G | Q |

| Kabat No. | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| | 4 | 5 | 6 | 7 | 8 | 9 | 5 0 | 1 | 2 | A | 3 | 4 | 5 | 6 | 7 | 8 | 9 | 6 0 | 1 | 2 | 3 | 4 | 5 | 6 | 7 | 8 | 9 | 7 0 | 1 | 2 | 3 | 4 | 5 | 6 | 7 | 8 | 9 | 8 0 | 1 | 2ABC |
| VH1 | G | L | E | W | I | G | X | X | X | X | X | X | X | X | X | X | X | X | X | X | R | A | T | L | T | A | D | K | S | T | S | T | A | Y | M | E | L | R | S | L |
| VH2 | G | L | E | W | I | G | X | X | X | X | X | X | X | X | X | X | X | X | X | X | R | A | T | L | T | A | D | K | S | T | S | T | A | Y | M | E | L | R | S | L |
| VH3 | G | L | E | W | I | G | X | X | X | X | X | X | X | X | X | X | X | X | X | X | R | V | T | I | T | A | D | K | S | T | S | T | A | Y | M | E | L | R | S | L |
| VH4 | G | L | E | W | I | G | X | X | X | X | X | X | X | X | X | X | X | X | X | X | R | V | T | I | T | A | D | K | S | T | S | T | A | Y | M | E | L | R | S | L |

| Kabat No. | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | 3 | 4 | 5 | 6 | 7 | 8 | 9 | 9 0 | 1 | 2 | 3 | 4 | 5 | 6 | 7 | 8 | 9 | 1 0 0 | A | 1 | 2 | 3 | 4 | 5 | 6 | 7 | 8 | 9 | 1 1 0 | 1 | 2 | 3 | |
| VH1 | R | S | E | D | S | A | V | Y | F | C | A | R | X | X | X | X | X | X | X | X | X | X | X | R | G | T | G | T | T | V | T | V | S | S | (SEQ ID NO: 12) |
| VH2 | R | S | E | D | T | A | V | Y | F | C | A | R | X | X | X | X | X | X | X | X | X | X | X | R | G | T | G | T | T | V | T | V | S | S | (SEQ ID NO: 14) |
| VH3 | R | S | E | D | T | A | V | Y | Y | C | A | R | X | X | X | X | X | X | X | X | X | X | X | R | G | T | G | T | T | V | T | V | S | S | (SEQ ID NO: 16) |
| VH4 | R | S | E | D | T | A | V | Y | Y | C | A | R | X | X | X | X | X | X | X | X | X | X | X | R | G | T | G | T | T | V | T | V | S | S | (SEQ ID NO: 18) |

```
Kabat           1         2         3
No.    1234567890123456789012345678901234567
VK1    DIQMTQSPSYLSASVGDRVTITC KASDHINNWLA WYQ
VK2    DIQMTQSPSSLSASVGDRVTITC KASDHINNWLA WYQ
VK3    DIQMTQSPSSLSASVGDRVTITC KASDHINNWLA WYQ
VK5    DIQMTQSPSSLSASVGDRVTITC KASDHINNWLA WYQ Kabat      4         5         6         7
No.    890123456789012345678901234567890
VK1    QKPGQAPRLLIS GATSLET GVPSRFSGSGTGKDYTLTISSLQP
VK2    QKPGQAPRLLIS GATSLET GVPSRFSGSGSGKDYTLTISSLQP
VK3    QKPGQAPRLLIS GATSLET GVPSRFSGSGSGKDFTLTISSLQP
VK5    QKPGQAPRLLIS GATSLET GVPSRFSGSGTDFTLTISSLQP Kabat     9         10
No.    12345678901234567 8901234567 8
VK1    EDFATYYC QQYWSTPYT FGGGTKVEIK (SEQ ID NO:20)
VK2    EDFATYYC QQYWSTPYT FGGGTKVEIK (SEQ ID NO:22)
VK3    EDFATYYC QQYWSTPYT FGGGTKVEIK (SEQ ID NO:24)
VK5    EDFATYYC QQYWSTPYT FGGGTKVEIK (SEQ ID NO:26)
```

HUMANIZED AFFINITY MATURED ANTI-FCRN ANTIBODIES

CROSS-REFERENCE TO RELATED APPLICATIONS

This Application is a Continuation-In-Part of PCT Application No. PCT/US2016/032168, filed May 12, 2016, which claims priority to U.S. Provisional Patent Application No. 62/160,423, filed May 12, 2015, and U.S. Provisional Patent Application No. 62/217,490, filed Sep. 11, 2015, both of which are incorporated herein in their entirety.

FIELD OF THE INVENTION

The invention relates to antibodies and antigen-binding portions thereof that bind to FcRn and their use for modulating or inhibiting interaction of FcRn with antibody Fc regions. The antibodies are useful as therapeutics for treatment of autoimmune and other disorders.

SEQUENCE LISTING

The instant application contains a Sequence Listing which has been submitted in ASCII format via EFS-Web and is hereby incorporated by reference in its entirety. The Sequence Listing, created on Nov. 13, 2017, is named Sequence Listing.txt and is 90,812 bytes in size.

BACKGROUND OF THE INVENTION

The neonatal Fc receptor (FcRn) is an intracellular trafficking integral membrane Fc receptor for IgG. FcRn was originally identified as a receptor functioning in neonatal life. It was first isolated from rodent gut as a heterodimer between a 12 kDa and a 40-50 kDa protein (Rodewald & Kraehenbuhl 1984, J. Cell. Biol. 99(1 Pt2): 159s-154s; Simister & Rees, 1985, Eur. J. Immunol. 15:733-738) and was cloned in 1989 (Simister & Mostov, 1989, Nature 337:184-187). Cloning and subsequent crystallization of FcRn revealed it to have an approximately 50 kDa major histocompatibility complex (MHC) class I-like heavy chain in non-covalent association with a 12 kDa β2-microglobulin light chain (Raghavan et al., 1993, Biochemistry 32:8654-8660; Huber et al., 1993, J. Mol. Biol. 230:1077-1083). Although first recognized in connection with fetal and neonatal life, FcRn is today known to continue to function throughout adult life. FcRn resides primarily in the early acidic endosomes where it binds to the Fc region of IgG in a pH-dependent manner, with micro- to nanomolar affinity at pH 6.5, while binding of FcRn to Fc at physiological pH is negligible. The bulk of FcRn is present in endosomes in most cells, and the interaction between FcRn and its IgG Fc ligands occurs within that acidic environment. In some cells, such as hematopoietic cells, significant levels of FcRn can be detected on the cell surface in addition to intracellular expression (Zhu et al., 2001, J. Immunol. 166:3266-3276). In this case, when the extracellular milieu is acidic, as in the case of neoplastic or infectious conditions, it is possible that FcRn can bind to IgG on the cell surface of these cell types. FcRn regulates serum IgG concentrations by binding to and protecting endocytosed monomeric IgG from degradation in the lysosomal compartment, and transporting the IgG to the cell surface for release at neutral extracellular pH. Through this mechanism, FcRn is responsible for the long serum half-life of IgG, since IgG that is not bound by FcRn enters the lysosomal pathway and is degraded.

During the first stages of life, FcRn confers passive immunity to offspring before and after birth by mediating transfer of IgG across the maternal placenta or neonatal intestinal walls. FcRn continues to function throughout adult life and is expressed in various tissues, e.g., the epithelium of the lung and liver, the vascular endothelium, as well as in monocytes, macrophages, and dendritic cells.

FcRn-deficient mice are more resistant to autoimmune diseases caused by pathogenic IgG autoantibodies because they are unable to maintain high concentrations of pathogenic serum IgG (Christianson et al., 1996, J. Immunol. 156:4932-4939; Ghetie et al., 1996, Eur. J. Immunol. 26:690-696; Israel et al., 1996, Immunol. 89:573-578). Administration of antibodies engineered to have modified Fc regions that bind with higher affinity to FcRn was found to ameliorate disease in a murine arthritis model (Patel et al., 2011, J. Immunol. 187:1015-1022). High dose administration of IgG in a number of autoimmune diseases has a palliative effect that can be explained at least partially by saturation of FcRn-mediated protection of IgG, shortening the half-life of pathogenic IgG (Jin & Balthasar, 2005, Hum. Immunol. 66:403-410; Akilesh et al., 2004, J. Clin. Invest. 113:1328-1333; Li et al., 2005, J. Clin. Invest. 115:3440-3450). Accordingly, specific blockade of FcRn-IgG interaction can be used to promote degradation of pathogenic IgG antibodies, for example to treat IgG mediated autoimmune diseases and to clear therapeutic antibodies from serum after administration. For example, in a rat model of experimentally-induced autoimmune myasthenia gravis, treatment with an FcRn heavy-chain specific monoclonal antibody resulted in a reduction of serum IgG concentration and a decrease in severity of the disease (Liu et al., 2007, J. Immunol. 178:5390-5398).

An absence of FcRn in hematopoietic cells is associated with more rapid clearance of IgG containing immune complexes from the bloodstream (Qiao et al., 2008, Proc. Natl. Acad. Sci. USA 105: 9337-9342). This indicates that specific blockade of FcRn-IgG interactions will also promote the clearance of IgG containing immune complexes from the circulation.

FcRn regulates the movement of IgG, and any bound cargo, between different compartments of the body via transcytosis across polarized cells. This process plays an important role in mucosal protection from infection, e.g., in the gastrointestinal tract. FcRn transports IgG across the epithelial cell barrier of the intestines and into the lumen. After IgG binds antigen in the lumen, the IgG/antigen complex is transported back through the barrier by FcRn into the lamina propria, allowing for processing of the IgG/antigen complex by dendritic cells and presentation of antigen to CD4$^+$ T cells in regional lymph nodes.

FcRn also plays a critical role in MHC class II antigen presentation and MHC class I cross-presentation of IgG-complexed antigen. When antigen is presented as an IgG-containing immune complex (IC), dendritic cells that are CD8-CD11b$^+$CD11c$^+$ (inflammatory dendritic cells) display significant cross-presentation at low antigen doses in a pathway that is highly dependent upon FcRn expression. This pathway involves the internalization of the ICs by Fcγ receptors into an acidic endosome. Subsequent binding of the ICs by FcRn within antigen presenting cells (APCs) initiates specific mechanisms that result in trafficking of the antigen-bearing IC into compartments where antigen is processed into peptide epitopes compatible with loading onto MHC (Baker et al., 2011, Proc. Natl. Acad. Sci. USA 108:9927-9932; Christianson et al., 2012, mAbs vol. 4, page 208, Introduction). Thus, FcRn in DCs enhances MHC II antigen presentation and induces proliferation of antigen-specific CD4+ T-cells as well as exhibiting a fundamental role in antigen presentation to CD8+ T cells (cytotoxic T cells). This latter CD8+ T cell-pathway is called cross-presentation and involves the crossover of extracellular antigens into an MHC class I-dependent pathway.

Blockade of FcRn-Ig IC interaction inhibits antigen presentation of IC and subsequent T cell activation stimulated by immune-associated antigen presentation. Interactions with IgG IC in APCs such as DCs also promote secretion of inflammatory cytokines such as IL-12, IFNγ, and TNFα. Thus, blockade of FcRn-Ig IC interaction is useful to inhibit production of inflammatory cytokines by innate immune cells and antigen activated T cells.

FcRn contains a binding site for serum albumin that is distinct from its binding site for the Fc domain of IgG, due to ionic interactions between FcRn and IgG or albumin on opposite faces of the FcRn heavy chain (Chaudhury et al., 2006, Biochemistry 45:4983-4990). Like its binding to IgG, binding of FcRn to albumin is strongly pH-dependent, occurring at acidic pH (typically less than pH 6, and optimally at pH 5) but not at neutral pH. Similar to its role in protecting IgG from degradation, FcRn binding of albumin protects albumin from degradation and results in an extended serum half-life for albumin.

SUMMARY OF THE INVENTION

The present invention provides antibodies and antigen-binding portions thereof that bind to FcRn. The antibodies bind to an epitope of FcRn that overlaps the binding site for the Fc domain of IgG and reduce or inhibit binding of FcRn to IgG and IgG as an immune complex.

Provided herein is an antibody or antigen-binding fragment thereof which binds to FcRn comprising a heavy chain variable region, the heavy chain variable region comprising CDR1, CDR2, and CDR3, wherein:
the sequence of CDR1 is SEQ ID NO:2;
the sequence of CDR2 is SEQ ID NO:4; and
the sequence of CDR3 is SEQ ID NO:78.

In one embodiment, the sequence of CDR3 is SEQ ID NO:76. In another embodiment, the sequence of CDR3 is SEQ ID NO:74.

In other embodiments, the sequence of CDR3 is selected from the group consisting of SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:74, SEQ ID NO:76, and SEQ ID NO:78. In one embodiment, the sequence of CDR3 is SEQ ID NO:49 or SEQ ID NO:55.

In some embodiments of the antibody or antigen-binding fragment, the amino acid at Kabat position 103 of the heavy chain variable region is tryptophan. In some embodiments, the amino acid at Kabat position 103 of the heavy chain variable region is arginine.

Also provided herein is an antibody or antigen-binding fragment thereof which binds to FcRn comprising a light chain variable region, the light chain variable region comprising CDR1, CDR2, and CDR3, wherein:
the sequence of CDR1 is SEQ ID NO:6;
the sequence of CDR2 is SEQ ID NO:8; and
the sequence of CDR3 is selected from the group consisting of SEQ ID NO:59, SEQ ID NO:62, SEQ ID NO:65, and SEQ ID NO:68.

Also provided herein is an antibody or antigen-binding fragment thereof which binds to FcRn comprising a heavy chain variable region and a light chain variable region, wherein each of the heavy chain and the light chain variable regions comprises CDR1, CDR2, and CDR3, and wherein:
the sequence of CDR1 of the heavy chain is SEQ ID NO:2;
the sequence of CDR2 of the heavy chain is SEQ ID NO:4; and
the sequence of CDR3 of the heavy chain is selected from the group consisting of SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, and SEQ ID NO:57; and
the sequence of CDR1 of the light chain is SEQ ID NO:6;
the sequence of CDR2 of the light chain is SEQ ID NO:8; and
the sequence of CDR3 of the light chain is selected from the group consisting of SEQ ID NO:10, SEQ ID NO:59, SEQ ID NO:62, SEQ ID NO:65, and SEQ ID NO:68.

In some embodiments, the sequence of CDR3 of the heavy chain is SEQ ID NO:49 or SEQ ID NO:55; and the sequence of CDR3 of the light chain is SEQ ID NO:10. In some embodiments, the sequence of CDR3 of the heavy chain is SEQ ID NO:55; and the sequence of CDR3 of the light chain is SEQ ID NO:10.

In some embodiments, the antibody or antigen-binding fragment herein is a chimeric or humanized antibody or antigen-binding fragment.

Also provided herein is an antibody or antigen-binding fragment thereof which binds to FcRn comprising a heavy chain variable region, wherein the sequence of the heavy chain variable region is SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, or SEQ ID NO:58, or the sequence of the heavy chain variable region is at least 95% identical to the heavy chain variable region amino acid sequence of SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, or SEQ ID NO:58.

In some embodiments, the antibody or antigen-binding fragment further comprises a light chain variable region, wherein the sequence of the light chain variable region is SEQ ID NO:20 or SEQ ID NO:22. In some embodiments, the sequence of the heavy chain variable region is SEQ ID NO:50 or SEQ ID NO:56. In some embodiments, the sequence of the heavy chain variable region is SEQ ID NO:56 and the sequence of the light chain variable region is SEQ ID NO:22.

In some embodiments, the antibody or antigen-binding fragment further comprises a light chain variable region, wherein the sequence of the light chain variable region is SEQ ID NO:61, SEQ ID NO:64, SEQ ID NO:67, or SEQ ID NO:70, or the sequence of the light chain variable region is at least 95% identical to the light chain variable region amino acid sequence of SEQ ID NO:61, SEQ ID NO:64, SEQ ID NO:67, or SEQ ID NO:70.

In some embodiments, the sequence of the heavy chain variable region is SEQ ID NO:50 or SEQ ID NO:56 and the sequence of the light chain variable region is SEQ ID NO:20 or SEQ ID NO:22. In some embodiments, the sequence of the heavy chain variable region is SEQ ID NO:56 and the light chain variable region comprises the framework region of the light chain variable region amino acid sequence of SEQ ID NO:22.

Also provided is an antibody or antigen-binding fragment thereof which binds to FcRn comprising a light chain variable region, wherein the sequence of the light chain variable region is SEQ ID NO:61, SEQ ID NO:64, SEQ ID NO:67, or SEQ ID NO:70, or the sequence of the light chain variable region is at least 95% identical to the light chain variable region amino acid sequence of SEQ ID NO:61, SEQ ID NO:64, SEQ ID NO:67, or SEQ ID NO:70. In some embodiments, the sequence of the light chain variable region is SEQ ID NO:67. In some embodiments, the sequence of the light chain variable region is SEQ ID NO:67 and the antibody or antigen-binding fragment further comprises a heavy chain variable region, wherein the heavy chain variable region comprises the framework region of SEQ ID NO:12. In some embodiments, the sequence of the light chain variable region is SEQ ID NO:67 and the antibody or antigen-binding fragment further comprises a heavy chain variable region, wherein the sequence of the heavy chain variable region is SEQ ID NO:12.

Also provided herein is an antibody or antigen-binding fragment thereof which binds to FcRn comprising a heavy chain variable region, wherein the heavy chain variable region comprises the framework region of the heavy chain variable region amino acid sequence of SEQ ID NO:12, SEQ ID NO:14, SEQ ID NO:16, or SEQ ID NO:18, or a framework region that is at least 95% identical to the framework region of SEQ ID NO:12, SEQ ID NO:14, SEQ ID NO:16, or SEQ ID NO:18. In some embodiments, the heavy chain variable region comprises the framework region of the heavy chain variable region amino acid sequence of SEQ ID NO:12, or a framework region that is at least 95% identical to the framework region of SEQ ID NO:12.

Also provided is an antibody or antigen-binding fragment thereof which binds to FcRn comprising a light chain variable region, wherein the light chain variable region comprises the framework region of the light chain variable region amino acid sequence of SEQ ID NO:20, SEQ ID NO:22, SEQ ID NO:24, or SEQ ID NO:26, or a framework region that is at least 95% identical to the framework region of SEQ ID NO:20, SEQ ID NO:22, SEQ ID NO:24, or SEQ ID NO:26. In some embodiments, the light chain variable region comprises the framework region of the light chain variable region amino acid sequence of SEQ ID NO:20 or SEQ ID NO:22, or a framework region that is at least 95% identical to the framework region of SEQ ID NO:20 or SEQ ID NO:22. In some embodiments, the light chain variable region comprises the framework region of the light chain variable region amino acid sequence of SEQ ID NO:22, or a framework region that is at least 95% identical to the framework region of SEQ ID NO:22.

Also provided herein is an antibody or antigen-binding fragment thereof which binds to FcRn comprising a heavy chain variable region, wherein the heavy chain variable region comprises the framework region of the heavy chain variable region amino acid sequence of SEQ ID NO:12, SEQ ID NO:14, SEQ ID NO:16, or SEQ ID NO:18, or a framework region that is at least 95% identical to the framework region of SEQ ID NO:12, SEQ ID NO:14, SEQ ID NO:16, or SEQ ID NO:18 and further comprises a light chain variable region, wherein the light chain variable region comprises the framework region of the light chain variable region amino acid sequence of SEQ ID NO:20, SEQ ID NO:22, SEQ ID NO:24, or SEQ ID NO:26, or a framework region that is at least 95% identical to the framework region of SEQ ID NO:20, SEQ ID NO:22, SEQ ID NO:24, or SEQ ID NO:26.

In some embodiments of the antibodies described herein, the antibody has isotype IgG4. In some embodiments, the antibody contains S241P modifications in the heavy chains. In some embodiments, the antibody lacks C-terminal lysines in the heavy chains. In some embodiments, the antibody contains S241P modifications in the heavy chains and lacks C-terminal lysines in the heavy chains.

In some embodiments, the antibody or antigen-binding fragment described herein is an scFv, Fv, Fab', Fab, F(ab')$_2$, or diabody.

Also provided herein is an antibody that competes with or cross-blocks an antibody or antigen-binding fragment thereof which binds to FcRn described herein. Also provided are antibodies that bind to the same epitope as antibodies described herein.

Also provided herein is an isolated nucleic acid encoding an FcRn antibody or antigen-binding fragment described herein. Also provided herein is a nucleic acid vector comprising an isolated nucleic acid encoding an FcRn antibody or antigen-binding fragment described herein. Also provided herein is a prokaryotic or eukaryotic host cell comprising an isolated nucleic acid encoding an FcRn antibody or antigen-binding fragment described herein. Also provided herein is a composition comprising an FcRn antibody or antigen-binding fragment described herein and a pharmaceutically acceptable carrier.

Also provided herein is a method of modulating the interaction between FcRn and IgG Fc which comprises contacting FcRn with an antibody or antigen-binding-fragment described herein.

Also provided herein is a method of promoting antibody degradation by a cell which comprises contacting FcRn with an antibody or antigen-binding fragment described herein.

Also provided herein is a method of promoting antibody degradation in a subject, which comprises administering to the subject an effective amount of the antibody or antigen-binding fragment described herein. In some embodiments, the antibody that is degraded is an autoantibody. In some embodiments, the antibody that is degraded is a therapeutic antibody.

Also provided herein is a method of ameliorating an IgG-mediated disease in a subject, which comprises administering to the subject an amount of an antibody or antigen-binding fragment described herein effective to ameliorate the IgG-mediated disease.

Also provided herein is a method of inhibiting immune complex binding by FcRn or decreasing circulating immune complexes by inhibiting FcRn-immune complex interactions, which comprises contacting FcRn with an effective amount of an antibody or antigen-binding fragment described herein.

Also provided herein is a method of inhibiting presentation of an immune complexed antigen by an antigen presenting cell (APC), which comprises contacting the APC with an amount of an antibody or antigen-binding fragment described herein effective to inhibit presentation of the antigen.

Also provided herein is a method of inhibiting cross-presentation of an immune complexed antigen by an antigen presenting cell (APC), which comprises contacting the APC with an amount of an antibody or antigen-binding fragment described herein effective to inhibit cross-presentation of the antigen.

Also provided herein is a method of inhibiting secretion of an inflammatory cytokine by an antigen presenting cell (APC), which comprises contacting the APC with an amount of an antibody or antigen-binding fragment described herein effective to inhibit secretion of the inflammatory cytokine. In some embodiments, the inflammatory cytokine is interleukin-6 (IL-6), interleukin-12 (IL-12), or tumor necrosis factor-α (TNFα).

Also provided herein is a method of inhibiting T cell activation by an antigen presenting cell which comprises contacting the antigen presenting cell with an antibody or antigen-binding fragment described herein.

Also provided herein is a method of treating, inhibiting, or reducing the severity of an autoimmune disease in a subject in need thereof, which comprises administering an effective amount of an antibody or antigen-binding fragment described herein. In some embodiments, the autoimmune disease is selected from the group consisting of pemphigus vulgaris, pemphigus foliaceus, paraneoplastic pemphigus, rheumatoid arthritis, systemic lupus erythematosis, Crohn's disease, idiopathic thrombocytopenic purpura (ITP), heparin induced thrombocytopenia (HIT), thrombotic thrombocytopenic purpura (TTP), autoimmune hemolytic anemia (AIHA), myasthenia gravis (MG), Chronic Inflammatory Demyelinating Polyneuropathy (CIDP), multifocal motor neuropathy, neuromyelitis optica, autoimmune thrombocytopenia, immune neutropenia, antihemophilic FVIII inhibitor, antiphospholipid syndrome, Kawasaki Syndrome, ANCA-associated disease, polymyositis, dermatomyositis, bullous pemphigoid, multiple sclerosis (MS), Guillain-Barre Syndrome, chronic polyneuropathy, ulcerative colitis, diabetes mellitus, autoimmune thyroiditis, Graves' opthalmopathy, autoimmune urticaria, vasculitides, and Rasmussen's encephalitis.

Also provided herein is a method of identifying antibodies that bind FcRn at both acidic pH and physiological pH comprising two or more screening steps that are carried out at pH 5.8-6.4. In some embodiments, the method comprises:
  (a) contacting a collection of candidate antibodies with FcRn or a portion thereof at pH 5.8-6.4 and isolating the antibodies that bind to FcRn or a portion thereof;
  (b) contacting the isolated antibodies of step (a) with FcRn or a portion thereof at pH 6.8-7.6 and isolating the antibodies that bind to FcRn or a portion thereof; and
  (c) contacting the isolated antibodies of step (b) with FcRn or a portion thereof at pH 5.8-6.4 and isolating the antibodies that bind to FcRn or a portion thereof.

Also provided herein is a method of blocking the transmission of pathogenic antibodies across the placenta that comprises administering to a pregnant mammal in need thereof a therapeutically effective amount of an FcRn antibody or antigen binding fragment thereof.

Also provided herein is a method of increasing the clearance of ICs from a subject which comprises administering to a subject in need thereof an FcRn antibody or antigen-binding fragment thereof. In some embodiments, the subject has a vasculitis that is immune complex-mediated.

Also provided herein is a method for determining whether a test antibody or antigen-binding fragment thereof blocks or diminishes the interaction between FcRn and immune complexes comprising:
  (a) obtaining whole blood from a mammal;
  (b) adding an immune complex to a first portion of the whole blood;
  (c) measuring the amount of a cytokine in the whole blood after the addition of the immune complex to obtain a first amount of the cytokine;
  (d) adding a test antibody or antigen-binding fragment thereof to a second portion of the whole blood;
  (e) adding the immune complex to the second portion of the whole blood after, or at the same time as, the addition of the test antibody or antigen-binding fragment thereof; and
  (f) measuring the amount of the cytokine in the second portion of the whole blood after the addition of the immune complex to obtain a second amount of the cytokine.

In some embodiments, the mammal is a human. In some embodiments, the antibody or antigen-binding fragment thereof is humanized, chimeric, or non-naturally occurring fully human. In some embodiments, the antibody or antigen-binding fragment thereof is an IgG, Fab, F(ab')$_2$, diabody, FV, scFV, blocking peptide, or antigen-binding fragment thereof. In some embodiments, the antibody or antigen-binding fragment thereof comprises a heavy chain variable region having SEQ ID NO:56 and a light chain variable region having SEQ ID NO:22.

In some embodiments, the cytokine is tumor necrosis factor-α (TNF-α), interleukin-6 (IL-6), interleukin-10 (IL-10), or interleukin-12 (IL-12). In some embodiments, the immune complex is artificial, i.e., does not occur naturally in the mammal. In some embodiments, the immune complex comprises a multimeric complex of the 4-hydroxy-5-iodo-3-nitrophenyl acetyl group (NIP) and chicken ovalbumin (OVA) and an anti-NIP antibody.

Also provided herein is a method for determining the expected level of responsiveness of a patient to an anti-FcRn therapy comprising:
  (a) obtaining whole blood from the patient prior to beginning the anti-FcRn therapy;
  (b) adding an immune complex to a first portion of the whole blood;
  (c) measuring the amount of a cytokine in the whole blood after the addition of the immune complex to obtain a first amount of the cytokine;
  (d) adding an antibody or antigen-binding fragment thereof that is known to block or diminish the interaction between FcRn and immune complexes to a second portion of the whole blood;
  (e) adding the immune complex to the second portion of the whole blood after, or at the same time as, the addition of the antibody or antigen-binding fragment thereof;
  (f) measuring the amount of the cytokine in the second portion of the whole blood after the addition of the immune complex to obtain a second amount of the cytokine; and
  (g) determining the difference between the first amount of the cytokine and the second amount of the cytokine.

In some embodiments, the patient is a human.

In some embodiments, the anti-FcRn therapy is the administration of an antibody comprising a heavy chain variable region amino acid sequence of SEQ ID NO:56 and a light chain variable region sequence of SEQ ID NO:22.

In some embodiments, the antibody or antigen-binding fragment thereof is an IgG, Fab, F(ab')$_2$, diabody, FV, scFV, blocking peptide, or a fragment thereof. In some embodiments, the antibody or antigen-binding fragment thereof is a F(ab')$_2$. In some embodiments, the antibody or antigen-binding fragment thereof comprises a heavy chain variable region having SEQ ID NO:56 and a light chain variable region having SEQ ID NO:22.

In some embodiments, the cytokine is tumor necrosis factor-α (TNF-α), interleukin-6 (IL-6), interleukin-10 (IL-10), or interleukin-12 (IL-12). In some embodiments, the immune complex is artificial, i.e., does not occur naturally in the mammal. In some embodiments, the immune complex comprises a multimeric complex of the 4-hydroxy-5-iodo-3-nitrophenyl acetyl group (NIP) and chicken ovalbumin (OVA) and an anti-NIP antibody. In some embodiments, the difference determined in step (g) is compared to a control value. In some embodiments, the difference determined in step (g) is compared to a difference obtained when the method is carried out with an immune complex comprising an antibody with three point mutations (I253A/H310A/H435A) in the Fc domain that abolish binding to FcRn.

Also provided herein is a method for monitoring the response of a patient to an anti-FcRn therapy comprising:
(a) obtaining whole blood from the patient before an anti-FcRn therapy begins;
(b) adding an immune complex to the whole blood;
(c) measuring the amount of a cytokine in the whole blood after the addition of the immune complex to obtain a first amount of the cytokine;
(d) obtaining whole blood from the patient after an anti-FcRn therapy begins;
(e) adding the immune complex to the whole blood of step (d);
(f) measuring the amount of the cytokine in the whole blood after the addition of the immune complex in step (e) to obtain a second amount of the cytokine; and
(g) determining the difference between the first amount of the cytokine and the second amount of the cytokine.

In some embodiments, the patient is a human.

In some embodiments, the anti-FcRn therapy is the administration of an antibody comprising a heavy chain variable region amino acid sequence of SEQ ID NO:56 and a light chain variable region sequence of SEQ ID NO:22. In some embodiments, the antibody is an IgG, Fab, F(ab')2, diabody, FV, scFV, blocking peptide, or a fragment thereof. In some embodiments, the antibody is a F(ab')2.

In some embodiments, the cytokine is tumor necrosis factor-α (TNF-α), interferon-γ (IFN-γ), interleukin-6 (IL-6), interleukin-10 (IL-10), or interleukin-12 (IL-12). In some embodiments, the immune complex comprises a multimeric complex of the 4-hydroxy-5-iodo-3-nitrophenyl acetyl group (NIP) and chicken ovalbumin (NIP) and an anti-NIP antibody. In some embodiments, the difference determined in step (g) is compared to a control value. In some embodiments, the difference determined in step (g) is compared to a difference obtained when the method is carried out with an immune complex comprising an antibody with three point mutations (I253A/H310A/H435A) in the Fc domain that abolish binding to FcRn. In some embodiments, the anti-FcRn therapy is adjusted based on the difference between the first amount of the cytokine and the second amount of the cytokine determined in step (g).

Also provided herein is a method of promoting endogenous antibody degradation prior to the administration of a therapeutic antibody comprising administering an anti-FcRn antibody or fragment thereof that is specific for the IgG binding site of FcRn to a subject in need of treatment with the therapeutic antibody prior to administering the therapeutic antibody.

Also provided herein is a method of promoting degradation of an exogenous therapeutic antibody that has been administered to a subject, which comprises administering to the subject an effective amount of an anti-FcRn antibody or fragment thereof.

In some embodiments, the method further comprises the step of administering the therapeutic antibody to the subject. In some embodiments, the pharmacokinetics or pharmacodynamics of the therapeutic antibody is enhanced.

Also provided herein is a method of measuring the level of anti-FcRn antibody in a subject after administration of an anti-FcRn antibody, the method comprising obtaining whole blood from the subject after an anti-FcRn antibody has been administered, wherein the whole blood comprises monocytes; and measuring the monocyte cell surface FcRn expression level. In some embodiments, the subject is a mammal. In other embodiments, the mammal is a human.

BRIEF DESCRIPTION OF THE FIGURES

FIG. 1 shows the amino acid sequences of humanized heavy chain variants ($V_H1$-$V_H4$). The variants are based on human heavy chain variable domain sequences and are aligned to show changes in amino acids incorporated at certain positions to minimize potential immunogenicity Amino acid residues that vary among the humanized frameworks are underlined. Kabat CDRs are boxed.

FIG. 2 shows the amino acid sequences of humanized light chain variants (Vκ1-Vκ3, Vκ5). The variants are based on human light chain variable domain sequences and are aligned to show changes in amino acids incorporated at certain positions to minimize potential immunogenicity Amino acid residues that vary among the humanized frameworks are underlined. Kabat CDRs are boxed.

DETAILED DESCRIPTION

Figure 3:
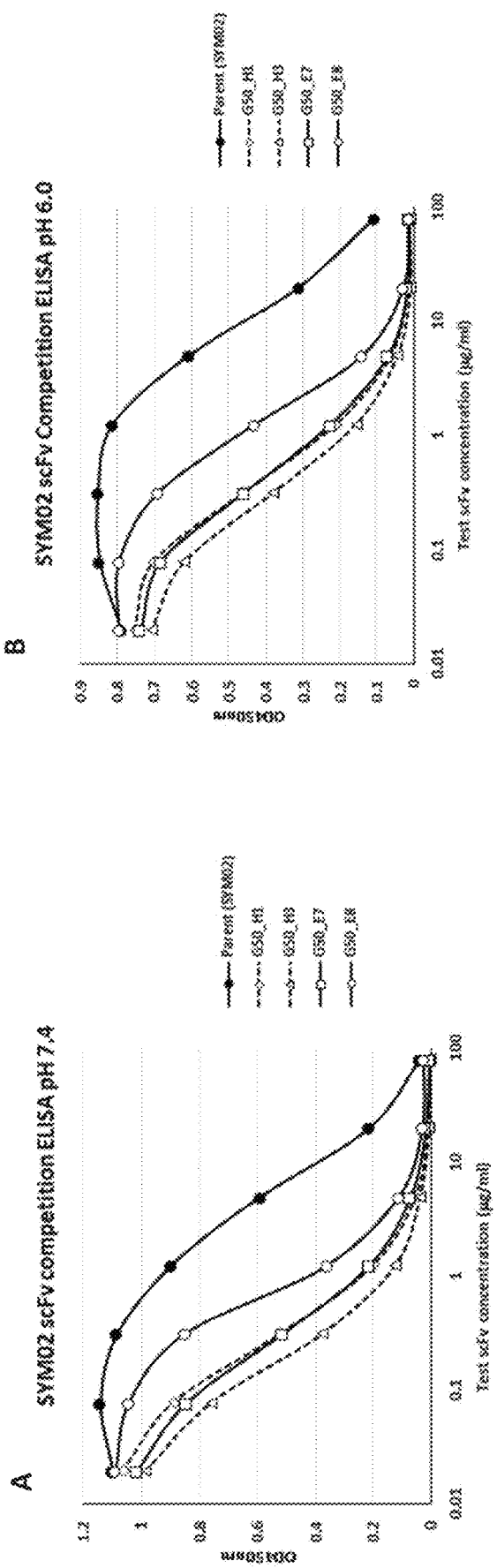
FIG. 3 shows a competitive ELISA comparing affinity matured heavy chains H1, H3, and E7, and affinity matured light chain E8, with the parent murine antibody. The affinity matured heavy chains were expressed as scFv with the humanized parental Vκ1 light chain and the affinity matured light chain was expressed as scFv with the humanized parental $V_H1$ heavy chain. scFv antibody was competed against biotinylated parent murine antibody for binding to immobilized FcRn at pH 7.4 (A) and pH 6.0 (B), and bound biotinylated parent murine antibody detected by streptavidin-HRP.

In one aspect, provided herein are antibodies and binding proteins that bind to FcRn. More particularly, the antibodies bind to an epitope of FcRn that overlaps the binding site for antibody Fc. Consequently, the antibodies modulate FcRn-mediated functions, such as binding of FcRn to IgG Fc, protection of IgG, and antigen presentation of immune complexes (IC). In another aspect, provided is an isolated nucleic acid comprising a sequence that encodes an FcRn antibody or antigen-binding portion thereof. In another aspect, provided is a composition suitable for administration to a subject which comprises and FcRn antibody or antigen-binding portion thereof and a pharmaceutically acceptable carrier.

In some embodiments, the antibodies disclosed herein inhibit the binding of human IgG to human FcRn but do not inhibit the binding of human serum albumin to human FcRn. In some embodiments, the antibodies disclosed herein decrease the serum half-life of human IgG but do not decrease the serum half-life of human serum albumin.

In another aspect, provided are methods of treatment. For example, by reducing binding of IgG Fc to FcRn, the antibodies or antigen-binding portions thereof set forth herein can be used to reduce the half-life of circulating IgG and treat or prevent antibody-mediated autoimmune disorders. Similarly the antibodies or antigen-binding portions thereof set forth herein may be used to reduce the half-life of therapeutic IgG and other therapeutic agents which comprise an IgG Fc region for stability. Such methods comprise administering to an individual in need of reduction of FcRn mediated IgG protection an amount of FcRn antibody sufficient to inhibit binding of FcRn to human IgG.

FcRn, also known as the neonatal Fc receptor, is an integral membrane Fc receptor for IgG. FcRn is a heterodimer of a membrane bound alpha-chain (GenBank accession no. NM004107) and soluble β2-microglobulin (β2m) (GenBank accession no. NM004048) and is structurally related to MHC class I molecules. FcRn regulates serum IgG concentrations by binding to and protecting endocytosed IgG from degradation in the lysosomal compartment, and transporting the IgG to the cell surface for release at neutral extracellular pH. Through this mechanism, FcRn is responsible for the long serum half-life of IgG. Accordingly, specific blockade of FcRn-IgG interaction can be used to promote degradation of pathogenic IgG antibodies. FcRn also binds multivalent IgG immune complexes (IC) within antigen presenting cells (APCs) such as dendritic cells (DCs), directing the bound IC into antigen processing pathways for presentation to T cells and activation of T cell mediated immune responses. Accordingly, specific blockade of FcRn-IC interaction can be used to inhibit T cell mediated immune responses, including reducing the production of inflammatory cytokines such as IL-6, IL-12, IFNγ, or TNFα.

Provided are antibodies that are derived from a murine antibody which specifically binds to FcRn and blocks binding of FcRn to IgG Fc but does not substantially bind to the albumin-binding site of FcRn. The antibodies have substantial improvements in binding affinity for FcRn at pH 7.4 and pH 6.0, and thus block binding of IgG Fc to FcRn under physiologic and acidic conditions. The antibodies are useful in the treatment of autoimmune and inflammatory diseases. The antibodies comprise one or more affinity matured CDRs. In some embodiments, the antibodies comprise one, two, three, four, five, or six CDRs described herein. The affinity maturation procedure provides antibodies that bind with high affinity to FcRn over the critical pH range 6.0 to 7.4. Thus, the antibodies effectively block binding of IgG Fc once internalized into the acidic environment of the endosome.

According to certain embodiments, the improved antibodies also feature humanized frameworks for reduced immunogenicity. In certain embodiments, CDRs of an FcRn-specific antibody are located in frameworks obtained from a human antibody. In other embodiments, CDRs of an FcRn-specific antibody are located in frameworks that are a composite of two or more human antibodies. In other embodiments, surface-exposed framework residues of an FcRn-specific antibody are replaced with framework residues of a human antibody. In a preferred embodiment, the frameworks are selected to minimize the presence of amino acid sequences predicted to be T cell epitopes over a wide population range. The CDRs may also be located in murine frameworks linked to human constant regions (i.e., chimeric antibodies).

As described further herein, for affinity maturation the heavy and light chain variable domain CDR3 regions were mutated and screened in scFv form at pH 6.0 and pH 7.4. Amino acid sequence variation was introduced into the heavy chain CDR3H region at amino acid positions 98-103 (a.a. 98-102 of CDR3H and a.a. 103 of FW4) using an oligonucleotide comprising the sequence KNCNNCNNCNNCSVCNWCYGG (SEQ ID NO:71) which provided for selected amino acids at each position as follows: a.a. 98: A, C, D, F, G, S, V, Y; a.a. 99: A, C, D, F, G, H, I, L, N, P, R, S, T, V, Y; a.a. 100: A, C, D, F, G, H, I, L, N, P, R, S, T, V, Y; a.a. 100a: A, C, D, F, G, H, I, L, N, P, R, S, T, V, Y; a.a. 101: A, D, G, H, P, R; a.a. 102: D, F, H, I, L, N, V, Y; a.a. 103: R, W Amino acid sequence variation was introduced into the light chain CDR3L region at amino acid positions 89-97 using the oligonucleotide sequence TGTMRSVMGTVSKRSRRCWMCYYCBW-CRYCTTC (SEQ ID NO:72), which provided for selected amino acids at each position, as follows: a.a. 88: C; a.a. 89: H, K, N, Q, R, S; a.a. 90: A, E, K, P, Q, T; a.a. 91: C, S, W, Y; a.a. 92: C, D, E, G, W, Y; a.a. 93: D, G, N, S; a.a. 94: N, S, T, Y; a.a. 95: F, L, P, S; a.a. 96: D, F, H, L, V, Y; a.a. 97: A, I, T, V.

As shown in the Examples below, this led to several CDR3H variants that conferred substantial improvements in FcRn binding affinity. Inspection of the variants obtained compared to the variability introduced into the CDR3H library indicates certain positions where amino acids remained relatively unchanged and others where variation could be introduced and result in improved binding. Accordingly, provided is an antibody or binding portion thereof that binds to FcRn, wherein the heavy chain comprises CDR3H, comprising certain amino acids that can be varied. In one such embodiment, CDR3H comprises $VX_1PPX_2X_3$, wherein $X_1$ is A, R, or S; $X_2$ is G, or R; and $X_3$ is I, L, or V (SEQ ID NO:73). In another such embodiment, the heavy chain CDR3H is $STTVX_1PPX_2X_3$, wherein $X_1$ is A, R, or S; $X_2$ is G, or R; and $X_3$ is I, L, or V (SEQ ID NO:74). In another such embodiment, the heavy chain CDR3H comprises $VX_1PPX_2X_3$, wherein $X_1$ is A, R, or S; $X_2$ is A, G, H, P, or R; and $X_3$ is H, I, L, or V (SEQ ID NO:75). In another such embodiment, the heavy chain CDR3H is $STTVX_1PPX_2X_3$, wherein $X_1$ is A, R, or S; $X_2$ is A, G, H, P, or R; and $X_3$ is H, I, L, or V (SEQ ID NO:76). In another such embodiment, the heavy chain CDR3H comprises $VX_1X_2X_3X_4X_5$, wherein $X_1$ is A, H, R, or S; $X_2$ is A, or P; $X_3$ is A, D, or P; $X_4$ is A, D, G, H, P, or R; $X_5$ is F, H, I, L, N, or V; and at least one of $X_2$ and $X_3$ is P (SEQ ID NO:77). In another such embodiment, the heavy chain CDR3H is $STTVX_1X_2X_3X_4X_5$, wherein $X_1$ is A, H, R, or S; $X_2$ is A, or P; $X_3$ is A, D, or P; $X_4$ is A, D, G, H, P, or R; $X_5$ is F, H, I, L, N, or V; and at least one of $X_2$ and $X_3$ is P (SEQ ID NO:78).

In certain embodiments, CDR3H is STTVSPADF (SEQ ID NO:27), STTVSPPPI (SEQ ID NO:29), STTVSPPAH (SEQ ID NO:31), or STTVAPPRL (SEQ ID NO:33). In certain embodiments, CDR3H is STTVHPDRN (SEQ ID NO:35), STTVSPPAL (SEQ ID NO:37), or STTVHPDHN (SEQ ID NO:39), STTVSPPHL (SEQ ID NO:41). In certain embodiments, CDR3H is STTVAPPPL (SEQ ID NO:43), STTVSPPHL (SEQ ID NO:45), STTVAPPGH (SEQ ID NO:47), or STTVSPPRV (SEQ ID NO:49). In certain embodiments, CDR3H is STTVSPPPL (SEQ ID NO:51), STTVAPPAH (SEQ ID NO:53), STTVRPPGI (SEQ ID NO:55), or STTVSAPGV (SEQ ID NO:57). In certain of these embodiments, the amino acid at position 103 of the heavy chain variable domain is tryptophan. In certain of these embodiments, the amino acid at position 103 of the heavy chain variable domain is arginine.

In certain embodiments wherein CDR3H is as set forth above, CDR1H is set forth by SEQ ID NO:2, and CDR2H set forth by SEQ ID NO:4.

Several heavy and light chain frameworks were developed, taking into account the framework sequences of the murine antibody in view of known antibody structures. The humanized frameworks were assembled from human variable domain sequences, with an eye to minimizing immunogenic T cell epitopes. Four such humanized heavy chain frameworks and four such light chain humanized frameworks are exemplified: $V_H1$ (SEQ ID NO:12); $V_H2$ (SEQ ID NO:14); $V_H3$ (SEQ ID NO:16); $V_H4$ (SEQ ID NO:18); Vκ1 (SEQ ID NO:20); Vκ2 (SEQ ID NO:22); Vκ3 (SEQ ID NO:24); and Vκ5 (SEQ ID NO:26). Corresponding oligonucleotide sequences for these exemplified humanized frameworks are set forth by: SEQ ID NO:11 ($V_H1$); SEQ ID NO:13 ($V_H2$); SEQ ID NO:15 ($V_H3$); SEQ ID NO:17 ($V_H4$); SEQ ID NO:19 (Vκ1); SEQ ID NO:21 (Vκ2); SEQ ID NO:23 (Vκ3); and SEQ ID NO:25 (Vκ5). In the heavy chain variable domain sequences provided in SEQ ID NO:12, SEQ ID NO:14, SEQ ID NO:16, and SEQ ID NO:18, CDR1H, CDR2H, and CDR3H amino acids are represented as "Xaa." The amino acid sequences of CDR1H and CDR2H are as set forth in SEQ ID NO:2 and SEQ ID NO: 4, respectively. A corresponding oligonucleotide sequence for CDR1H is set forth by SEQ ID NO:1 and a corresponding oligonucleotide sequence for CDR2H is set forth by SEQ ID NO:3. In the light chain variable domain sequences provided in SEQ ID NO:20, SEQ ID NO:22, SEQ ID NO:24, and SEQ ID NO:26, a particular amino acid is specified at all positions. The amino acid sequences of CDR1L is as set forth in SEQ ID NO:6, CDR2L as set forth in SEQ ID NO:8, and CDR3L as set forth in SEQ ID NO:10. Corresponding oligonucleotide sequences are as set forth by: SEQ ID NO:5 (CDR1L); SEQ ID NO:7 (CDR2L); and SEQ ID NO:9 (CDR3L). The locations of FWs and CDRs in the heavy and light chains will also be evident from FIG. 1 and FIG. 2, respectively.

Table 1 provides non-limiting examples of affinity matured, humanized FcRn-binding antibody heavy and light chain variable domains and CDRs wherein the CDR3H and CDR3L were affinity matured as described above. As describe herein, the variable domains were selected for improved binding at pH 6.0 and pH 7.4, and demonstrate substantially improved binding relative to the parent murine antibody.

TABLE 1

Antibody Amino Acid Sequences by SEQ ID NO

| | CDR1H | CDR2H | CDR3H | $V_H$ |
|---|---|---|---|---|
| A4 $V_H1$ | 2 | 4 | 27 | 28 |
| A7 $V_H1$ | 2 | 4 | 29 | 30 |
| A8 $V_H1$ | 2 | 4 | 31 | 32 |
| C4 $V_H1$ | 2 | 4 | 33 | 34 |
| C7 $V_H1$ | 2 | 4 | 35 | 36 |
| D1 $V_H1$ | 2 | 4 | 37 | 38 |
| E4 $V_H1$ | 2 | 4 | 39 | 40 |
| E7 $V_H1$ | 2 | 4 | 41 | 42 |
| F7 $V_H1$ | 2 | 4 | 43 | 44 |
| G4 $V_H1$ | 2 | 4 | 45 | 46 |
| G7 $V_H1$ | 2 | 4 | 47 | 48 |
| G9 $V_H1$ | 2 | 4 | 49 | 50 |
| H1 $V_H1$ | 2 | 4 | 51 | 52 |
| H2 $V_H1$ | 2 | 4 | 53 | 54 |
| H3 $V_H1$ | 2 | 4 | 55 | 56 |
| H4 $V_H1$ | 2 | 4 | 57 | 58 |

| | CDR1L | CDR2L | CDR3L | $V_L$ |
|---|---|---|---|---|
| E3_4 Vκ1 | 6 | 8 | 59 | 60 |
| E3_4 Vκ2 | 6 | 8 | 59 | 61 |
| B7 Vκ1 | 6 | 8 | 62 | 63 |
| B7 Vκ2 | 6 | 8 | 62 | 64 |
| E8 Vκ1 | 6 | 8 | 65 | 66 |
| E8 Vκ2 | 6 | 8 | 65 | 67 |
| F3 Vκ1 | 6 | 8 | 68 | 69 |
| F3 Vκ2 | 6 | 8 | 68 | 70 |

The affinity matured heavy chain CDR3s may be combined with a heavy chain CDR1 (e.g., a CDR1 having SEQ ID NO:2) and/or a heavy chain CDR2 (e.g., a CDR2 having SEQ ID NO:4). The affinity matured light chain CDR3s may be combined with a light chain CDR1 (e.g., a CDR1 having SEQ ID NO:6) and/or a light chain CDR2 (e.g., a CDR2 having SEQ ID NO:8). In some embodiments, the affinity matured, humanized FcRn-binding antibody comprises one, two, three, four, five, or six of the CDRs described herein.

As disclosed in the Examples below, various antibody variable domains exemplified herein are based on a murine antibody and contain affinity matured CDRs, and certain embodiments also feature humanized FWs. It will be evident that the heavy and light chain variable domains disclosed in Table 1 are designed to be compatible. Thus any heavy chain variable domain disclosed in Table 1 may be coexpressed with any disclosed light chain to create a functional anti-FcRn antibody. Moreover, an affinity matured heavy chain variable domain may be paired with a humanized non-affinity matured light chain variable domain disclosed herein, and an affinity matured light chain variable domain may be paired with a humanized non-affinity matured heavy chain variable domain. In a preferred embodiment, an affinity matured heavy chain variable domain may be paired with a humanized light chain variable domain. Also, Table 1 sets forth heavy chain CDRs in $V_H1$ and light chain CDRs in Vκ1 and Vκ2. The heavy chain CDRs are also compatible with, e.g., frameworks $V_H2$, $V_H3$, and $V_H4$ disclosed herein (see FIG. 1). The light chain CDRs are also compatible with, e.g., frameworks Vκ3 and Vκ5 disclosed herein (see FIG. 2). As used herein, the designations $V_H1$, $V_H2$, $V_H3$, $V_H4$, Vκ1, Vκ2, Vκ3, Vκ5 refer to exemplary humanized frameworks disclosed herein, and are not references to human germline gene families. It will be apparent that any heavy chain or light chain variable domain disclosed herein can be combined with a library of complementary variable domains and screened to identify new antibodies having improved or altered binding characteristics. In some embodiments, the sequence of the heavy chain variable region is the affinity matured humanized sequence of SEQ ID NO:56 and the sequence of the light chain variable region is humanized sequence of SEQ ID NO:22. In some embodiments, the affinity matured, humanized FcRn-binding antibody comprises one, two, three, four, five, or all of the CDRs of the heavy and light chain variable regions of SEQ ID NO:56 and SEQ ID NO:22. In particular, SEQ ID NO:56 includes a heavy chain CDR1 having the sequence of SEQ ID NO:2, a heavy chain CDR2 having the sequence of SEQ ID NO:4, and a heavy chain CDR3 having the sequence of SEQ ID NO:55, and SEQ ID NO:22 has a light chain CDR1 having the sequence of SEQ ID NO: 6, a light chain CDR2 having the sequence of SEQ ID NO: 8, and a light chain CDR3 hay the sequence of SEQ ID NO: 10.

Provided herein are antibodies and antigen binding portions that are similar, but not identical to, those disclosed in Table 1. The antibodies can have one or more amino acid substitutions, deletions, insertions, and/or additions. In certain embodiments, an FcRn antibody comprises a heavy chain variable domain that is at least 85%, at least 90%, or at least 95% identical to a heavy chain variable domain set forth in Table 1. In certain embodiments, an FcRn antibody comprises a light chain variable domain that is at least 85%, at least 90%, or at least 95% identical to a light chain variable domain set forth in Table 1. In certain embodiments, an antibody comprises a heavy chain variable domain set forth in Table 1 or a heavy chain variable domain that is at least 85%, at least 90%, or at least 95% identical to a heavy chain variable domain set forth in Table 1 and a light chain variable domain set forth in Table 1 or a light chain variable domain that is at least 85%, at least 90%, or at least 95% identical to a light chain variable domain set forth in Table 1.

In an embodiment, an FcRn antibody contains a heavy chain variable domain which comprises CDR sequences, i.e., CDR1H, CDR2H, and CDR3H, set forth in Table 1 and a framework (i.e., FW1, FW2, FW3, and FW4) of $V_H1$, $V_H2$, $V_H3$, or $V_H4$ or a framework that is at least 85%, 90%, or 95% identical to a framework of $V_H1$, $V_H2$, $V_H3$, or $V_H4$. In an embodiment, an FcRn antibody contains a heavy chain variable domain which comprises CDR sequences set forth in Table 1 and frameworks such that the heavy chain variable domain sequence is at least 85%, or at least 90%, or at least 95% identical to a variable domain set forth in Table 1.

In an embodiment, an FcRn antibody contains a light chain variable domain which comprises CDR sequences, i.e., CDR1L, CDR2L, and CDR3L, set forth in Table 1 and a framework (i.e., FW1, FW2, FW3, and FW4) of Vκ1, Vκ2, Vκ3, or Vκ5 or a framework that is at least 85%, 90%, or 95% identical to a framework of Vκ1, Vκ2, Vκ3, or Vκ5. In an embodiment, an FcRn antibody contains a light chain variable domain which comprises CDR sequences set forth in Table 1 and frameworks such that the light chain variable domain sequence is at least 85%, or at least 90%, or at least 95% identical to a light chain variable domain set forth in Table 1.

In an embodiment, an FcRn antibody contains a heavy chain variable domain which comprises CDR sequences, i.e., CDR1H, CDR2H, and CDR3H, set forth in Table 1 and a framework (i.e., FW1, FW2, FW3, and FW4) of $V_H1$, $V_H2$, $V_H3$, or $V_H4$ or a framework that is at least 85%, 90%, or 95% identical to a framework of $V_H1$, $V_H2$, $V_H3$, or $V_H4$, and a light chain variable domain which comprises Vκ1, Vκ2, Vκ3, or Vκ5 or a sequence that is at least 85%, 90%, or 95% identical to Vκ1, Vκ2, Vκ3, or Vκ5.

"Identity" refers to the number or percentage of identical positions shared by two amino acid or nucleic acid sequences, taking into account the number of gaps, and the length of each gap, which need to be introduced for optimal alignment of the two sequences.

Where an amino acid sequence is described as being at least 85%, or at least 90%, or at least 95% identical to another amino acid sequence, the amino acid sequences may differ by conservative substitutions (including where all substitutions are conservative substitutions).

Amino acid substitutions can be made, in some cases, by selecting substitutions that do not differ significantly in their effect on maintaining (a) the structure of the peptide backbone in the area of the substitution, (b) the charge or hydrophobicity of the molecule at the target sit; or (c) the bulk of the side chain. For example, naturally occurring residues can be divided into groups based on side-chain properties; (1) hydrophobic amino acids (methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Examples of substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

Methods and computer programs for determining sequence similarity are publicly available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at http://www.ncbi.nlm.nih.gov/blast/). In comparing sequences, these methods account for various substitutions, deletions, and other modifications.

As used herein, the term "Complementarity Determining Regions" (CDRs, i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region can comprise amino acid residues from a "complementarity determining region" as defined by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain. Likewise, "frameworks" (FWs) comprise amino acids 1-23 (FW1), 35-49 (FW2), 57-88 (FW3), and 98-107 (FW4) in the light chain variable domain and 1-30 (FW1), 36-49 (FW2), 66-94 (FW3), and 103-113 (FW4) in the heavy chain variable domain taking into account the Kabat numbering system (Kabat et al., Sequences of Proteins of Immunological Interest, 5th Ed. Public Health Service, National Institutes of Health, Bethesda, Md. (1987, 1991)).

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain.

Antibodies are proteins that recognize and bind to a specific antigen or substance. In preferred embodiments, the antibodies or antigen-binding portions set forth herein bind FcRn at least as strongly as the natural ligand (i.e., IgG Fc). Affinity, represented by the equilibrium constant for the dissociation of an antigen with an antibody (Kd), measures the binding strength between an antigenic determinant and an antibody binding site. The affinity of an antibody for an antigen may be determined by the use of a suitable surface plasmon energy resonance measurement. Such a measurement might be the BIACORE® assay described in International Patent Application Publication WO 2005/012359 and elsewhere herein. Other methods of determining affinity include enzyme-linked immunosorbent assays or competition assays such as radioimmunoassays.

Avidity is the measure of the strength of binding between an antibody with its antigen. Avidity is related to both the affinity between an antigenic determinant and an antigen binding site on the antibody, and the number of binding sites (valence) per antibody. For example, a monovalent antibody (e.g., Fab or scFv) has one binding site for a particular epitope. An IgG antibody has two antigen binding sites. Typical values of K (the reciprocal of the dissociation constant $K_d$) are $10^5$ to $10^{11}$ liters/mol. Any K weaker than $10^4$ liters/mol is considered to indicate binding which is nonspecific.

In certain embodiments, the antibodies or antigen-binding portions thereof described herein bind to the Fc-binding portion of human FcRn with a $K_d$ of $10^5$ to $10^{12}$ liters/mol, $10^6$ to $10^{12}$ liters/mol, $10^7$ to $10^{12}$ liters/mol, $10^8$ to $10^{12}$ liters/mol, $10^9$ to $10^{12}$ liters/mol, $10^{10}$ to $10^{12}$ liters/mol, or $10^{11}$ to $10^{12}$ liters/mol. In other embodiments, the antibodies or antigen-binding portions thereof described herein bind to the Fc-binding portion of human FcRn with a $K_d$ of $10^5$ to $10^{11}$ liters/mol, $10^6$ to $10^{11}$ liters/mol, $10^7$ to $10^{11}$ liters/mol, $10^8$ to $10^{11}$ liters/mol, $10^9$ to $10^{11}$ liters/mol, or $10^{10}$ to $10^{11}$ liters/mol. In other embodiments, the antibodies or antigen-binding portions thereof described herein bind to the Fc-binding portion of human FcRn with a $K_d$ of $10^5$ to $10^{10}$ liters/mol, $10^6$ to $10^{10}$ liters/mol, $10^7$ to $10^{10}$ liters/mol, $10^8$ to $10^{10}$ liters/mol, or $10^9$ to $10^{10}$ liters/mol. In other embodiments, the antibodies or antigen-binding portions thereof described herein bind to the Fc-binding portion of human FcRn with a $K_d$ of $10^5$ to $10^8$ liters/mol, $10^6$ to $10^8$ liters/mol, or $10^7$ to $10^8$ liters/mol.

In order to minimize immunogenicity when administered to a human, the antibodies or antigen-binding portions thereof set forth herein preferably include human constant domains. Thus, the antibodies can be any isotype or subtype, including but not limited to $IgG_1$, $IgG_{2a}$, $IgG_{2b}$, $IgG_3$, $IgG_4$, IgM, IgA, IgD, or IgE. The antibody class may be selected to optimize effector functions (e.g., to increase or reduce complement dependent cytotoxicity (CDC) or antibody dependent cellular cytotoxicity (ADCC)). In certain embodiments, the constant region (i.e., $C_H1$, $C_H2$, $C_H3$, and/or the hinge region) is modified, for example to increase or decrease binding to an Fc receptor. In certain embodiments, the constant domain is modified to promote or stabilize heavy chain-heavy chain binding. In certain embodiments, the antibody is an IgG4 antibody and the hinge region of the heavy chains is modified by changing the serine at position 241 to proline, leading to extended serum half-life (Angal et al., 1993, Mol. Immunol. 30:105-108). In certain embodiments, the antibody is an IgG4 antibody and the C-terminal lysines at position 478 of the heavy chains are deleted. In some embodiments, the $IgG_4$ antibody has both the S241P modifications and lacks the C-terminal lysines.

In certain embodiments, FcRn-binding antibody fragments are provided. An Fv is the smallest fragment that contains a complete heavy and light chain variable domain, including all six hypervariable loops (CDRs). Lacking constant domains, the variable domains are noncovalently associated. The heavy and light chains may be connected into a single polypeptide chain (a "single-chain Fv" or "scFv") using a linker that allows the $V_H$ and $V_L$ domains to associate to form an antigen binding site. See, e.g., Bird et al., 1988, Science 242:423 and Huston et al, 1988, Proc. Natl. Acad. Sci. USA 85:5879. In an embodiment, the linker is (Gly-Gly-Gly-Gly-Ser)$_3$. Since scFv fragments lack the constant domains of whole antibodies, they are considerably smaller than whole antibodies. scFv fragments are also free of normal heavy-chain constant domain interactions with other biological molecules which may be desired in certain embodiments.

"Antibodies," as used herein, refers to monomers as well as multimers. Intact antibodies, including multimers, or antibody fragments bearing antigen-binding regions of antibodies can be used. Antigen-binding regions include, without limitation, Fv, scFv, Fab, Fab' and F(ab')$_2$ fragments. Methods for preparing antibody fragments are well known in the art. For example, monovalent Fab fragments, which lack the heavy chain hinge region can be prepared from whole immunoglobulin by proteolytic digestion with papain. Bivalent F(ab')$_2$ fragments, which retain the heavy chain hinge region can be prepared by proteolytic digestion with pepsin.

Fragments of an antibody containing $V_H$, $V_L$, and optionally $C_L$, $C_H1$, or other constant domains can also be used. Such fragments may also be recombinantly produced. Many other useful antigen-binding antibody fragments are known in the art, and include, without limitation, diabodies, triabodies, single domain antibodies, and other monovalent and multivalent forms.

Further provided are multivalent antigen-binding proteins, which can be in the form, without limitation, of antibodies, antigen-binding fragments thereof, and proteins comprising all or part of antigen-binding portions of antibodies. Multivalent antigen-binding proteins may be monospecific, bispecific, or multispecific. The term specificity refers to the number of different types of antigenic determinants to which a particular molecule can bind. If an immunoglobulin molecule binds to only one type of antigenic determinant, the immunoglobulin molecule is monospecific. If the immunoglobulin molecule binds to different types of antigenic determinants then the immunoglobulin molecule is multispecific.

In one embodiment, a multivalent single chain antibody includes a variable light-chain fragment linked to a variable heavy-chain fragment (similar to an scFv), which is further linked by another peptide linker to at least one other antigen binding domain. Typically, the peptide linker is composed of about fifteen amino acid residues. In a preferred embodiment, the number of $V_L$ and $V_H$ domains is equivalent. For example, a bivalent single chain antibody can be represented as follows: $V_L$-$L_1$-$V_H$-$L_2$-$V_L$-$L_3$-$V_H$ or $V_L$-$L_1$-$V_H$-$L_2$-$V_H$-$L_3$-$V_L$ or $V_H$-$L_1$-$V_L$-$L_2$-$V_H$-$L_3$-$V_L$ or $V_H$-VL-$L_3$-$V_H$. Multivalent single chain antibodies which are trivalent or greater have one or more antibody fragments joined to a bivalent single chain antibody by additional peptide linkers. One example of a trivalent single chain antibody is:

Two single chain antibodies can be combined to form a diabody, also known as bivalent dimer. See, e.g., European Patent Application 0 404 097 or Hollinger et al., 1993, Proc. Natl. Acad. Sci. USA 90:6444. Diabodies have two chains. Each chain of the diabody includes a $V_H$ domain connected to a $V_L$ domain by a short linker of about 5-10 amino acid residues, e.g., (Gly-Gly-Gly-Gly-Ser), (Gly-Gly-Gly-Gly-Ser)$_2$. Such linkers are short enough to prevent intrachain pairing between domains on the same chain, thus driving interchain pairing between complementary domains on different chains and recreate two antigen-binding sites. The diabody structure is compact, with antigen-binding sites at opposite ends of the molecule.

$V_H$ and $V_L$ framework sequence variants and affinity matured antibodies can be subjected to a pre-clinical ex vivo assay to assess potential immunogenicity. One such assay is EPISCREEN™ which provides an effective technology for predicting T cell immunogenicity by quantifying T cell responses to protein therapeutics. The assay uses a cohort of blood donors carefully selected based on MHC class II haplotypes to best represent the number and frequency of HLA-DR allotypes expressed in the world population. The assay provides a method by which the immunogenicity of whole proteins can be assessed both in terms of magnitude and frequency of T cell responses (Jones et al., J Interferon Cytokine Res. 2004 24(9):560-72; Jones et al., J Thromb Haemost. 2005 3(5):991-1000).

Antibodies which compete with or cross-block the binding of an antibody disclosed herein to FcRn, or which themselves are cross-blocked from binding FcRn by an antibody disclosed herein, may be used in the methods of blocking FcRn activity disclosed herein. In some cases, these competing, cross-blocking, or cross-blocked antibodies bind to an epitope of FcRn which borders and/or overlaps with the epitope bound by an antibody described herein. In some cases, these competing, cross-blocking, or cross-blocked antibodies are chimeric, fully human, or humanized antibodies that bind to an epitope of FcRn which is the same as the epitope bound by an antibody described herein.

Competing, cross-blocking, and cross-blocked antibodies can be identified using any suitable method known in the art, including competition ELISAs or BIACORE® assays where binding of the competing or cross blocking antibody to human FcRn prevents the binding of an antibody disclosed herein or vice versa.

In certain embodiments, the competing or cross-blocking antibody is an antibody which blocks the binding of human IgG to human FcRn and which competes with or cross-blocks the binding of an antibody having a heavy chain sequence selected from the group consisting of SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, and SEQ ID NO:58 and a light chain sequence selected from the group consisting of SEQ ID NO:20, SEQ ID NO:22, SEQ ID NO:61, SEQ ID NO:64, SEQ ID NO:67, and SEQ ID NO:70. In some embodiments, the competition or cross-blocking is greater than 80%, greater than 85%, greater than 90%, or greater than 95%.

In certain embodiments, the competing or cross-blocking antibody is an antibody which blocks the binding of human IgG to human FcRn and which competes with or cross-blocks the binding of an antibody having a heavy chain sequence of SEQ ID NO:56 and a light chain sequence of SEQ ID NO:22. In some embodiments, the competition or cross-blocking is greater than 80%, greater than 85%, greater than 90%, or greater than 95%. In some embodiments, the antibody binds to the same epitope as an antibody having a heavy chain sequence of SEQ ID NO:56 and a light chain sequence of SEQ ID NO:22. In some embodiments, the antibody binds at residues 85-88, 113-116, and 130-133 of the alpha chain of human FcRn (SEQ ID NO: 79). In other embodiments, the antibody binds at residues 1-3 and 59 of the beta chain of human FcRn (SEQ ID NO: 80). In some embodiments, the antibody binds at residues 85-88, 113-116, and 130-133 of the alpha chain of human FcRn (SEQ ID NO: 79) and at residues 1-3 and 59 of the beta chain of human FcRn (SEQ ID NO: 80). In other embodiments, the antibody binds at one or more residues selected from residues 85-88, 113-116, and 130-133 of the alpha chain of human FcRn (SEQ ID NO: 79) and residues 1-3 and 59 of the beta chain of human FcRn (SEQ ID NO: 80).

In certain embodiments, the competing or cross-blocked antibody is an antibody which blocks the binding of human IgG to human FcRn and whose binding to FcRn is competed with or cross-blocked by an antibody having a heavy chain sequence selected from the group consisting of SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, and SEQ ID NO:58 and a light chain sequence selected from the group consisting of SEQ ID NO:20, SEQ ID NO:22, SEQ ID NO:61, SEQ ID NO:64, SEQ ID NO:67, and SEQ ID NO:70. In some embodiments, the competing or cross-blocked antibody is competed with or cross-blocked to greater than 80%, greater than 85%, greater than 90%, or greater than 95%.

In certain embodiments, the competing or cross-blocked antibody is an antibody which blocks the binding of human IgG to human FcRn and whose binding to FcRn is competed with or cross-blocked by an antibody having a heavy chain sequence of SEQ ID NO:56 and a light chain sequence of SEQ ID NO:22. In some embodiments, the competing or cross-blocked antibody is competed with or cross-blocked to greater than 80%, greater than 85%, greater than 90%, or greater than 95%.

In some embodiments, the competing, cross-blocking, or cross-blocked antibodies are chimeric, fully human, or are humanized. In some embodiments, the competing, cross-blocking, or cross-blocked antibodies bind to the Fc binding site of human FcRn with an affinity of $10^5$ to $10^{11}$ liters/mol., $10^6$ to $10^{11}$ liters/mol., $10^7$ to $10^{11}$ liters/mol., $10^8$ to $10^{11}$ liters/mol., $10^9$ to $10^{11}$ liters/mol., or $10^{10}$ to $10^{11}$ liters/mol.

Also provided herein are nucleic acids encoding anti-FcRn antibodies and functional fragments thereof, vectors, host cells and expression systems. The nucleic acids encoding anti-FcRn antibodies and functional fragments thereof may be, e.g., DNA, cDNA, RNA, synthetically produced DNA or RNA, or a recombinantly produced chimeric nucleic acid molecule comprising any of those polynucleotides either alone or in combination. For example, provided is an expression vectors containing a polynucleotide sequence encoding an anti-FcRn antibodies described herein operably linked to expression control sequences suitable for expression in a eukaryotic and/or prokaryotic host cell. A variety of expression vectors have been developed for the efficient synthesis of antibodies and fragments in prokaryotic cells such as bacteria and eukaryotic systems, including but not limited to yeast and mammalian cell culture systems have been developed. The vectors can comprise segments of chromosomal, non-chromosomal and synthetic DNA sequences.

Any suitable expression vector can be used. For example, prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages. An example of a vector useful in yeast is the 2p plasmid. Suitable vectors for expression in mammalian cells include well-known derivatives of SV40, adenovirus, retrovirus-derived DNA sequences and shuttle vectors derived from combination of functional mammalian vectors, such as those described above, and functional plasmids, e.g., pLenti6.3/V5-REST®, pT-Rex™-DEST31®, pGene/V5-HispGene/V5-His® (Life Technologies, Norwalk, Conn.).

Additional eukaryotic expression vectors are known in the art (e.g., P. J. Southern and P. Berg, J. Mol. Appl. Genet., 1, 327-341 (1982); Subramani et al., Mol. Cell. Biol., 1: 854-864 (1981); Kaufmann and Sharp, "Amplification And Expression of Sequences Cotransfected with a Modular Dihydrofolate Reductase Complementary DNA Gene," J. Mol. Biol. 159, 601-621 (1982); Kaufmann and Sharp, Mol. Cell. Biol. 159, 601-664 (1982); Scahill et al., "Expression And Characterization Of The Product Of A Human Immune Interferon DNA Gene In Chinese Hamster Ovary Cells," Proc. Nat'l Acad. Sci. USA 80, 4654-4659 (1983); Urlaub and Chasin, Proc. Nat'l Acad. Sci. USA 77, 4216-4220, (1980).

The expression vectors may contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from cytomegalovirus, polyoma, adenovirus, retrovirus, and simian virus, e.g., the early and late promoters or SV40, and other sequences known to control the expression of genes of prokaryotic or eukaryotic cells and their viruses or combinations thereof. Other expression control sequences that may be used include DNA regulatory sequences from the Chinese hamster elongation factor-1α (CHEF1) gene (Running Deer & Allison, 2004, Biotechnol. Prog. 20:880-889; U.S. Pat. No. 5,888,809).

Also provided are recombinant host cells containing the expression vectors previously described. Antibodies or antigen-binding portions thereof set forth herein can be expressed in cell lines other than in hybridomas. Nucleic acids, which comprise a sequence encoding a polypeptide as described herein, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, NS0 cells, Chinese Hamster Ovary (CHO) cells, Baby Hamster Kidney (BHK) cells and many others. In some embodiments, the cell is a myeloma cell, e.g., SP2/0, which can be transfected and grown in culture of in the peritoneal cavity of a mouse where high concentrations of IgG can be recovered from ascites fluid. Suitable additional eukaryotic cells include yeast and other fungi. Useful prokaryotic hosts include, for example, *E. coli*, such as *E. coli* SG-936, *E. coli* HB 101, *E. coli* Vκ3110, *E. coli* X1776, *E. coli* X2282, *E. coli* DHI, and *E. coli* MRC1, *Pseudomonas, Bacillus*, such as *Bacillus subtilis*, and *Streptomyces*.

These present recombinant host cells can be used to produce an antibody, or antigen-binding portion thereof, by culturing the cells under conditions permitting expression of the antibody or fragment thereof and purifying the antibody or fragment thereof from the host cell or medium surrounding the host cell. Thus, in one embodiment, provided is a method for the production of an antibody capable of binding the Fc-binding region of FcRn, said method comprising: (a) culturing a host cell as described above; and (b) isolating said antibody from the host cell or the culture medium of the host cell.

The transformed hosts can be grown in fermentors and cultured according to techniques known in the art. Once the desired level of expression of the antibodies is reached, the antibodies can be purified according to standard procedures of the art, including ammonium sulfate precipitation, purification on affinity columns, column chromatography, gel electrophoresis and the like. For use in the therapeutic methods described herein, it is preferred that the antibodies be purified to at least 90%, 95%, 98%, or 99% purity.

Targeting of the expressed antibody or fragment for secretion in the recombinant host cells can be facilitated by inserting a signal or secretory leader peptide-encoding sequence (see, Shokri et al., Appl Microbiol Biotechnol. 60(6):654-64 (2003), Nielsen et al., Prot. Eng. 10:1-6 (1997) and von Heinje et al., Nucl. Acids Res. 14:4683-4690 (1986)) at the 5' end of the antibody-encoding gene of interest. These secretory leader peptide elements can be derived from either prokaryotic or eukaryotic sequences. Accordingly suitably, secretory leader peptides are used, being amino acids joined to the N-terminal end of a polypeptide to direct movement of the polypeptide out of the host cell cytosol and secretion into the medium.

The antibodies or antigen-binding portions thereof can be fused to additional amino acid residues. Such amino acid residues can be a peptide tag, perhaps to facilitate isolation. Other amino acid residues for homing of the antibodies to specific organs or tissues are also contemplated.

In some embodiments, the antibody or antigen-binding portion thereof is conjugated to one or more effector molecules, which provide some desirable property (e.g., increased serum half-life) to the antibody or antigen-binding portion thereof. In a particular embodiment, the antibody or antigen-binding portion thereof is conjugated to polyethyleneglycol (PEG). The PEG may be attached to any amino acid side chain or terminal amino acid functional group, e.g., a free amino, imino, thiol, hydroxyl, or carboxyl group. Methods of attaching PEG to antibodies are known in the art and may be employed. See, e.g., European Patent Application EP 0948544; European Patent Application EP1090037; "Poly(ethyleneglycol) Chemistry, Biotechnical and Biomedical Applications," 1992, J. Milton Harris (ed), Plenum Press, New York; "Poly(ethyleneglycol) Chemistry and Biological Applications," 1997, J. Milton Harris & S. Zalipsky (eds), American Chemical Society, Washington D.C.; "Bioconjugation Protein Coupling Techniques for the Biomedical Sciences," 1998, M. Aslam & A. Dent, Grove Publishers, New York; or Chapman, A. 2002, Advanced Drug Delivery Reviews 2002, 54:531-545.

In another embodiment, an antibody or antigen-binding portion thereof as set forth herein is made by expressing a nucleic acid encoding the antibody in a transgenic animal, such that the antibody is expressed and can be recovered. For example, the antibody can be expressed in a tissue specific manner that facilitates recovery and purification. In one such embodiment, an antibody of the expressed in the mammary gland for secretion during lactation. Transgenic animals, include but are not limited to mice, goat, and rabbit.

Provided herein are methods of identifying antibodies that bind FcRn at both acidic pH and physiological pH. The methods comprise two or more screening steps that are carried out at acidic pH (e.g., pH 5.0-6.6, pH 5.8-6.4, pH 6.0-6.2, or pH 6.0). The two or more acidic screening steps are alternated with screening steps carried out at physiological pH (e.g., pH 6.8-8.2, pH 6.8-7.6, pH 7.2-7.4, or pH 7.4).

For example, one embodiment of such methods comprises:
  (a) contacting a collection of candidate antibodies with FcRn or a portion thereof at pH 5.8-6.4 and isolating the antibodies that bind to FcRn or a portion thereof;
  (b) contacting the isolated antibodies of step (a) with FcRn or a portion thereof at pH 6.8-7.6 and isolating the antibodies that bind to FcRn or a portion thereof;
  (c) contacting the isolated antibodies of step (b) with FcRn or a portion thereof at pH 5.8-6.4 and isolating the antibodies that bind to FcRn or a portion thereof.

Another embodiment comprises:
  (a) providing a collection of candidate FcRn-binding antibodies:
  (b) contacting the collection of candidate FcRn-binding antibodies with FcRn or a portion thereof at pH 6.0 under conditions such that complexes are formed between the FcRn or a portion thereof and at least some of the candidate FcRn-binding antibodies;

(c) isolating the complexes;

(d) separating the candidate FcRn-binding antibodies from the isolated complexes;

(e) contacting the separated candidate FcRn-binding antibodies from step (d) with FcRn or a portion thereof at pH 7.4 under conditions such that complexes are formed between the FcRn or a portion thereof and at least some of the candidate FcRn-binding antibodies;

(f) isolating the complexes formed in step (e);

(g) separating the candidate FcRn-binding antibodies from the isolated complexes of step (f);

(h) contacting the separated candidate FcRn-binding antibodies from step (g) with FcRn or a portion thereof at pH 6.0 under conditions such that complexes are formed between the FcRn or a portion thereof and at least some of the candidate FcRn-binding antibodies;

(i) isolating the complexes formed in step (h);

(j) separating the candidate FcRn-binding antibodies from the isolated complexes of step (i) to obtain antibodies that bind FcRn at both acidic pH and physiological pH.

In some embodiments, the collection of candidate FcRn-binding antibodies may be a library of antibodies or portions thereof (e.g., a library of scFvs displayed on phage).

In some embodiments, the concentration of FcRn or a portion thereof is decreased at each contacting step. For example, step (b) may be carried out at a concentration of 25 nM, step (e) may be carried out at a concentration of 2.5 nM, and step (h) may be carried out at a concentration of 0.25 nM.

In some embodiments, the FcRn or a portion thereof may be attached to a solid support, e.g., a magnetic bead. In such embodiments, the isolating steps may be simply the binding of the antibodies to the FcRn or a portion thereof attached to the solid support, e.g., when the solid support is a chromatography column. In some embodiments, the FcRn or a portion thereof may be attached to a moiety that facilitates isolation of the complexes between FcRn or a portion thereof and the antibodies. For example, the FcRn or a portion thereof may be attached to biotin.

Physical and functional properties of antibodies or antigen-binding portions thereof as set forth herein can be determined by routine procedures. For example, the ability of an antibody to block FcRn activity can be assessed by a number of methods. One way is to show competitive binding with an antibody known to bind to the Fc binding region of FcRn. Another is to show protection of serum Ig from catabolism. See, e.g., Akiles et al., 2007, J. Immunol. 179:4580-88. Another way is to measure the ability of FcRn to recycle or transcytose antibodies in the presence of a test agent. For example, Claypool et al., 2002, J. Biol. Chem. 277:28038-50 used Madin-Darby Canine Kidney (MDCK) cells transfected to express human FcRn and ($3_2$m to demonstrate transcytosis of IgG. Other suitable polarized epithelial cell lines that express FcRn endogenously include the human intestinal epithelial cell lines T84 and Caco-2. In the Examples, there is provided an assay method to determine the ability of antibodies or antigen-binding portions thereof as set forth herein to bind to FcRn and inhibit antigen presentation by Class II MHC and cross-presentation by Class I MHC.

Provided herein is a whole blood-based assay to determine the ability of an anti-FcRn antibody to modulate the processing of immune complexes (ICs). FcRn functions to bind monomeric IgG and divert it from catabolism, thus lengthening its serum half-life. Multimeric IgG or antigen-antibody ICs, on the other hand, interact with FcRn to activate cytokine production and to direct the ICs into antigen presentation pathways. A major role of FcRn is the regulation of cell-mediated immune functions, presumably via uptake, processing, and presentation of IgG-containing ICs. The activation of cytokine production associated with this aspect of FcRn biology allows for the development of a whole blood-based assay to determine the ability of an anti-FcRn antibody to modulate (e.g., block or diminish) this FcRn-IC interaction.

In one embodiment, the assay comprises obtaining whole blood from a mammal (e.g., a human or a non-human primate) and adding a pre-formed immune complex to the whole blood to stimulate the production of cytokines, in the presence or the absence of a test antibody or antigen-binding fragment thereof, and measuring the production of a suitable cytokine. If the test antibody or antigen-binding fragment thereof is able to block or diminish the amount of cytokine measured, as compared to the amount measured in the absence of the test antibody or antigen-binding fragment thereof, the test antibody or antigen-binding fragment thereof is considered to be capable of interfering with the interaction between FcRn and ICs. As a control to ensure that the measured cytokines are the result of interaction between FcRn and the IC, the assay may be run with an IC in which the IgGs are incapable of binding FcRn. Such IgGs are known (see, e.g., Qiao et al., 2008, Proc. Natl. Acad. Sci. USA 105: 9337-9342). Running the assay with such IgGs should result in no, or very little, cytokine production.

In another embodiment, the assay can also be used to predict which patients are likely to benefit from therapy with an anti-FcRn antibody or antigen-binding fragment thereof. In this version of the assay, the assay is run with an antibody or antigen-binding fragment thereof that is known to be effective in blocking or diminishing the interaction between FcRn and the IC. Those patients who show a significant reduction of cytokine production upon running the assay with the known anti-FcRn antibody or antigen-binding fragment thereof, as opposed to running the assay in the absence of the known anti-FcRn antibody or antigen-binding fragment thereof, will be more likely to benefit from therapy with an anti-FcRn antibody or antigen-binding fragment thereof than those patients who show lesser, or no, reductions in cytokine production.

Another version of the assays described above involves administering a test antibody or antigen binding fragment thereof or a known anti-FcRn antibody or antigen binding fragment thereof to a subject or a patient before the subject or patient's blood is obtained for use in the whole blood assay. In this version of the assay, a test antibody or antigen binding fragment thereof or a known anti-FcRn antibody or antigen binding fragment thereof is not added to the whole blood, since the test antibody or antigen binding fragment thereof or known anti-FcRn antibody or antigen binding fragment thereof will already be present in the blood.

Another use for the whole blood-based assay is to monitor the response of a patient to anti-FcRn therapy. In this embodiment, the assay is run on the blood of patients who have been receiving an anti-FcRn antibody or antigen-binding fragment thereof for a predetermined period of time. Pre-formed ICs are added to the blood and the amount of cytokines produced is measured. That amount is compared to the amount that had been produced from the same patient's blood obtained before treatment with the anti-FcRn antibody or antigen-binding fragment thereof began. If the amount of cytokine produced is less in the assay when it is run after treatment began, this indicates that the patient is responding to the therapy. If no difference, or an insignificant difference, in cytokine production is observed for the blood from the patient taken before treatment began, as compared to the blood taken after treatment had been ongoing for the predetermined period of time, this indicates that the patient is not significantly responding to the therapy. In those cases where there is a difference observed, the magnitude of the difference is an indication of the magnitude of the response—the greater the difference, the more the patient is responding to the anti-FcRn therapy. The assay in this version would not involve adding an anti-FcRn antibody or antigen-binding fragment thereof to the blood.

Provided herein is a method for determining whether a test antibody or antigen-binding fragment thereof blocks or diminishes the interaction between FcRn and immune complexes comprising:
(a) obtaining whole blood from a mammal;
(b) adding an immune complex to a first portion of the whole blood;
(c) measuring the amount of a cytokine in the whole blood after the addition of the immune complex to obtain a first amount of the cytokine;
(d) adding a test antibody or antigen-binding fragment thereof to a second portion of the whole blood;
(e) adding the immune complex to the second portion of the whole blood after, or at the same time as, the addition of the test antibody or antigen-binding fragment thereof;
(f) measuring the amount of the cytokine in the second portion of the whole blood after the addition of the immune complex to obtain a second amount of the cytokine; and
(g) determining the difference between the first amount of the cytokine and the second amount of the cytokine;
where if the first amount of the cytokine is greater than the second amount of the cytokine the test antibody or antigen-binding fragment thereof blocks or diminishes the interaction between FcRn and immune complexes.

Provided herein is a method for determining the expected level of responsiveness of a patient to an anti-FcRn therapy comprising:
(a) obtaining whole blood from the patient prior to beginning the anti-FcRn therapy;
(b) adding an immune complex to a first portion of the whole blood;
(c) measuring the amount of a cytokine in the whole blood after the addition of the immune complex to obtain a first amount of the cytokine;
(d) adding an antibody or antigen-binding fragment thereof that is known to block or diminish the interaction between FcRn and immune complexes to a second portion of the whole blood;
(e) adding the immune complex to the second portion of the whole blood after, or at the same time as, the addition of the antibody or antigen-binding fragment thereof;
(f) measuring the amount of the cytokine in the second portion of the whole blood after the addition of the immune complex to obtain a second amount of the cytokine; and
(g) determining the difference between the first amount of the cytokine and the second amount of the cytokine.

The magnitude of the difference between the first amount of the cytokine and the second amount of the cytokine, where the first amount is greater than the second amount, indicates the degree to which the patient is expected to respond to the anti-FcRn therapy. Depending on this degree of expected response, the patient may be selected to receive the anti-FcRn therapy.

Provided herein is a method for monitoring the response of a patient to an anti-FcRn therapy comprising:
(a) obtaining whole blood from the patient before the anti-FcRn therapy begins;
(b) adding an immune complex to the whole blood;
(c) measuring the amount of a cytokine in the whole blood after the addition of the immune complex to obtain a first amount of the cytokine;
(d) obtaining whole blood from the patient after the anti-FcRn therapy begins;
(e) adding the immune complex to the whole blood of step (d);
(f) measuring the amount of the cytokine in the whole blood after the addition of the immune complex in step (e) to obtain a second amount of the cytokine; and
(g) determining the difference between the first amount of the cytokine and the second amount of the cytokine.

The magnitude of the difference between the first amount of the cytokine and the second amount of the cytokine, where the first amount is greater than the second amount, indicates the degree to which the patient is responding to the anti-FcRn therapy. Based upon the observed degree of responsiveness, the anti-FcRn therapy may be adjusted. For example, if the first amount is only slightly greater than the second amount, the anti-FcRn therapy may be increased. If the anti-FcRn therapy is an antibody described herein, the frequency of the administration of the antibody may be increased and/or the dosage administered may be increased. Following adjustment of the therapy, the assay may be run again. In this way an iterative process of assay, therapy adjustment, assay, therapy adjustment, etc. may be carried out and an optimal level of therapy determined.

In some embodiments of the above-described methods, the difference between the first amount of the cytokine and the second amount of the cytokine is compared to a control value.

In some embodiments of the above-described methods, the mammal is a human. In some embodiments, the human is suffering from an autoimmune disease. In some embodiments, the human is suffering from an autoimmune disease selected from the group consisting of pemphigus vulgaris, pemphigus foliaceus, paraneoplastic pemphigus, rheumatoid arthritis, systemic lupus erythematosis, Crohn's disease, idiopathic thrombocytopenic purpura (ITP), heparin induced thrombocytopenia (HIT), thrombotic thrombocytopenic purpura (TTP), autoimmune hemolytic anemia (AIHA), myasthenia gravis (MG), Chronic Inflammatory Demyelinating Polyneuropathy (CIDP), multifocal motor neuropathy, neuromyelitis optica, autoimmune thrombocytopenia, immune neutropenia, antihemophilic FVIII inhibitor, antiphospholipid syndrome, Kawasaki Syndrome, ANCA-associated disease, polymyositis, dermatomyositis, bullous pemphigoid, multiple sclerosis (MS), Guillain-Barre Syndrome, chronic polyneuropathy, ulcerative colitis, diabetes mellitus, autoimmune thyroiditis, Graves' opthalmopathy, autoimmune urticaria, vasculitides, and Rasmussen's encephalitis.

In some embodiments, the immune complex is an immune complex of antigen+antigen-specific antibody. In some embodiments, the immune complex is artificial, i.e., does not occur naturally in the mammal. For example, the immune complex may be a multimeric complex of 4-hydroxy-5-iodo-3-nitrophenyl acetic acid (NIP), chicken ovalbumin (OVA), and an anti-NIP antibody. One possibility for the anti-NIP antibody is a chimeric IgG antibody that contains a murine variable region specific for 4-hydroxy-5-iodo-3-nitrophenyl acetic acid and an Fc domain from wild-type human IgG$_1$ (Claypool, 2004, Mol. Biol. Cell 15:1746-1759). In another embodiment, the anti-NIP antibody is an IgG antibody with three point mutations (I253A/H310A/H435A) in the Fc domain that abolish binding to FcRn. In some embodiments, the immune complex is a NIP-OVA-antibody complex comprising 5, 6, 7, 8, 9, 10, 11, 12, 13, 14, or 15 NIP moieties.

A function of the immune complexes in the assays described herein is to multimerize FcRn. Thus, the assay may be run with other substances that are able to carry out this function. For example, a substance having appropriately spaced Fc domains may be used. Such a substance might be a styrene bead coated with an antibody that has an Fc domain that is able to be recognized by FcRn or coated with a polypeptide containing appropriately spaced Fc domains. The antibody may be directly bound to the bead or an antigen which the antibody recognizes may be directly bound to the bead and the antibody may be attached to the bead by virtue of recognizing and binding to the antigen.

Accordingly, provided herein is a method of multimerizing FcRn comprising:
  (a) obtaining whole blood from a mammal; and
  (b) adding to the whole blood a substance having appropriately spaced Fc domains such that FcRn in the whole blood is multimerized.

In some embodiments, an anti-FcRn antibody or antigen-binding fragment thereof is added to the whole blood before, or at the same time as, the substance.

In some embodiments, the method comprises (c) measuring the amount of a cytokine in the whole blood. In some embodiments, the amount of the cytokine is measured in the absence and in the presence of an anti-FcRn antibody or antigen-binding fragment and the difference in amounts measured is determined.

In some embodiments of the above-described methods, the cytokine is tumor necrosis factor-α (TNF-α), interleukin-6 (IL-6), interleukin-10 (IL-10), or interleukin-12 (IL-12). The amount of cytokine in whole blood may be measured by methods known in the art. For example, the amount of cytokine protein may be measured with an antibody specific for the cytokine or the amount of mRNA transcript for the cytokine in the whole blood may be measured.

In some embodiments of the method described above for determining the expected level of responsiveness of a patient to anti-FcRn therapy, a report is generated that specifies the expected level of responsiveness and/or that the patient has been selected to receive anti-FcRn therapy, the report is communicated to a health care provider, and an anti-FcRn therapy is administered to the patient. In some embodiments, a report is generated that specifies the expected level of responsiveness and/or that the patient has been selected to receive anti-FcRn therapy, the report is communicated to a physician, and the physician administers the anti-FcRn therapy or directs another health care provided to administer the anti-FcRn therapy.

In some embodiments of the above-described assay methods, the antibody or antigen-binding fragment thereof is an IgG, Fab, F(ab')$_2$, diabody, FV, scFV, blocking peptide, or a fragment thereof. In some embodiments, the antibody or antigen-binding fragment thereof is a F(ab')$_2$. In some embodiments, the antibody or antigen-binding fragment thereof comprises a heavy chain variable region having SEQ ID NO:56 and a light chain variable region having SEQ ID NO:22.

In some embodiments of the above-described method for monitoring the response of a patient to an anti-FcRn therapy, the anti-FcRn therapy is the administration to the patient of an antibody that binds to the Fc-binding region of FcRn and blocks or diminishes the binding of IgG to FcRn. In some embodiments, the antibody is H3Vκ2, H3E8, G9Vκ2, or G9E8. In some embodiments, the antibody comprises a heavy chain CDR3 having the sequence SEQ ID NO:49 or SEQ ID NO:55. In some embodiments, the antibody comprises the heavy chain variable region amino acid sequence set forth in SEQ ID NO:50 or SEQ ID NO:56. In some embodiments, e.g., G9Vκ2, the antibody comprises the heavy chain variable region amino acid sequence set forth in SEQ ID NO:50 and the light chain variable region amino acid sequence set fourth in SEQ ID NO:22. In some embodiments, e.g., H3Vκ2, the antibody comprises the heavy chain variable region amino acid sequence set forth in SEQ ID NO:56 and the light chain variable region amino acid sequence set forth in SEQ ID NO:22. In some embodiments, the antibody is an IgG, Fab, F(ab')2, diabody, FV, scFV, blocking peptide, or a fragment thereof. In some embodiments, the antibody or antigen-binding fragment thereof is a F(ab')$_2$.

In some embodiments, the amount of antibody added to the whole blood is determined by testing various amounts and establishing a dose-response curve. In some embodiments, the amount of antibody added is sufficient to bring the antibody concentration in the whole blood to between 1 nM and 1 μM, between 10 nM and 750 nM, or between 100 nM and 500 nM.

In some embodiments of the above-described assay methods, the antibody or antigen-binding fragment thereof is humanized, chimeric, or non-naturally occurring fully human.

The specific region or epitope of human FcRn to which the antibodies disclosed herein bind can be identified by any suitable epitope mapping method known in the art. Such methods include screening peptides of varying lengths from FcRn for binding to the antibody in order to determine which amino acids of FcRn the antibody binds to. The peptides may be produced by well-known methods such as proteolytic digestion of FcRn or chemical synthesis. Techniques such as mass spectrometry may be used to identify peptides that bind the antibody. Alternatively, NMR spectroscopy or X-ray crystallography can be used. Once identified, the binding peptides may be used as immunogens to obtain additional antibodies which bind the same epitope of FcRn.

It is understood that the anti-FcRn antibodies or antigen-binding portions thereof set forth herein, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, histidine, glutamate, citrate, mannitol, trehalose, sucrose, arginine, acetate, Polysorbate 80, Poloxamer 188, and the like, as well as combinations thereof. Pharmaceutically acceptable carriers may further comprise minor amounts of auxiliary substances such as wetting or emulsifying agents, preservatives or buffers, which enhance the shelf life or effectiveness of the antibodies.

In some embodiments, the compositions comprising antibody and pharmaceutically acceptable carrier are lyophilized.

The compositions comprising antibody and pharmaceutically acceptable carrier may comprise the anti-FcRn antibodies or antigen-binding portions thereof set forth herein at various concentrations. For example, the compositions may comprise antibody at 10 mg/ml to 200 mg/ml, 25 mg/ml to 130 mg/ml, 50 mg/ml to 125 mg/ml, 75 mg/ml to 110 mg/ml, or 80 mg/ml to 100 mg/ml. The compositions also may comprise antibody at about 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, or 150 mg/ml.

In the methods described herein, a therapeutically effective amount of an antibody or antigen-binding portions thereof set forth herein is administered to a mammal in need thereof. The term "administering" as used herein means delivering the antibodies or antigen-binding portions thereof set forth herein to a mammal by any method that may achieve the result sought. They may be administered, for example, subcutaneously, intravenously or intramuscularly. Although antibodies or antigen-binding portions thereof set forth herein are particularly useful for administration to humans, they may be administered to other mammals as well. The term "mammal" as used herein is intended to include, but is not limited to, humans, laboratory animals, domestic pets and farm animals. "Therapeutically effective amount" means an amount of antibody or antigen-binding portions thereof set forth herein that, when administered to a mammal, is effective in producing the desired therapeutic effect. For example, depending on the disease, for an antibody, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

In certain embodiments, the antibody or antigen-binding portion thereof is administered to the mammal by intravenous infusion, i.e., introduction of the antibody or antigen-binding portion thereof into the vein of a mammal over a certain period of time. In certain embodiments, the period of time is about 5 minutes, about 10 minutes, about 30 minutes, about 1 hour, about 2 hours, about 4 hours, or about 8 hours.

In certain embodiments, the antibody or antigen-binding portion thereof is administered to the mammal by subcutaneous delivery, i.e., under the skin of the mammal, generally by pinching and lifting the skin away from underlying tissue and injecting the antibody or antigen-binding portion thereof into the space under the skin thereby formed.

In certain embodiments, a dose of a compound or a composition is administered to a subject every day, every other day, every couple of days, every third day, once a week, twice a week, three times a week, or once every two weeks. In other embodiments, two, three or four doses of a compound or a composition is administered to a subject every day, every couple of days, every third day, once a week or once every two weeks. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

Methods of administration include but are not limited to parenteral, intradermal, intravitrial, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound locally. This may be achieved, for example, and not by way of limitation, by local infusion, topical application, by injection, by means of a catheter, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (See Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (See, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

The above-described administration schedules are provided for illustrative purposes only and should not be considered limiting. A person of ordinary skill in the art will readily understand that all doses are within the scope of the invention.

"Autoimmune disease" refers to a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include neoplastic cells.

Antibodies and antigen-binding fragments that bind to FcRn can be administered to a subject to modulate an immune response or to treat, prevent, or diagnose disorders, such as immune disorders. The term "treating" refers to administering a therapy effective to improve or ameliorate a disorder or disease or reduce or prevent progression of a disorder or disease. An effective amount can vary, depending on, e.g., the condition or disorder, individual subject, and may be tailored to the subject. The antibodies and antigen-binding fragments that bind to FcRn can also be used in vitro.

In one embodiment, provided is a method of modulating the interaction between FcRn and IgG Fc which comprises contacting FcRn in a cell or in a subject with an FcRn antibody or antigen-binding fragment described herein. In an embodiment, the modulation inhibits the interaction between FcRn and IgG Fc. Thus, provided is a method of promoting antibody degradation by a cell or in a subject. In one embodiment, the antibody is an autoantibody. In another embodiment, the antibody is a therapeutic antibody.

In another embodiment, provided is a method of treating or ameliorating an IgG-mediated disease in a subject, which comprises administering to the subject an FcRn antibody or antigen binding fragment disclosed herein in an amount effective to treat or ameliorate the IgG-mediated disease. Such IgG-mediated diseases may be those that involve pathogenic IgG antibodies in monomeric form or as IgG-containing immune complexes (IC) and include coagulopathies, vasculitides, collagen disorders, dermatological diseases, neurological diseases, inflammatory bowel diseases, and organ-specific disorders.

In another embodiment, provided is a method of blocking the transmission of pathogenic antibodies across the placenta that comprises administering to a pregnant mammal in need thereof a therapeutically effective amount of an FcRn antibody or antigen binding fragment disclosed herein.

In another embodiment, provided is a method of inhibiting immune complex (IC) binding by FcRn, which comprises contacting FcRn in a cell or in a subject with an FcRn antibody or antigen-binding fragment described herein. Accordingly, also provided is a method of inhibiting presentation of an immune complexed antigen by an antigen presenting cell (APC), which comprises contacting the APC with an amount of an FcRn antibody or antigen-binding fragment thereof. Similarly, in another embodiment, provided is a method of inhibiting cross-presentation of an immune complexed antigen by an antigen presenting cell (APC), which comprises contacting the APC with an amount of an FcRn antibody or antigen-binding fragment thereof.

In another embodiment, provided is a method of increasing the clearance of ICs from a subject which comprises administering to a subject in need thereof an FcRn antibody or antigen-binding fragment described herein. Such methods may be used to treat vasculitides that are IC-mediated.

In another embodiment, provided is a method of inhibiting secretion of an inflammatory cytokine by an antigen presenting cell (APC), which comprises contacting the APC with an FcRn antibody or antigen-binding fragment thereof. Non-limiting examples of inflammatory cytokines include, e.g., interleukin-12 (IL-12), interleukin-6 (IL-6) and interferon γ (IFN γ).

In another embodiment, provided is a method of inhibiting T cell activation by an antigen presenting cell which comprises contacting the antigen presenting cell with an FcRn antibody or antigen-binding fragment described herein.

Provide herein is a method of treating an autoimmune disease, which comprises administering an effective amount of an FcRn antibody or antigen binding portion thereof to a patient in need thereof. Non-limiting example of diseases that can be treated include pemphigus (pemphigus vulgaris, pemphigus foliaceus or paraneoplastic pemphigus), Crohn's disease, idiopathic thrombocytopenic purpura (ITP), heparin induced thrombocytopenia (HIT), thrombotic thrombocytopenic purpura (TTP), Myasthenia Gravis (MG), and Chronic Inflammatory Demyelinating Polyneuropathy (CIDP). Additional non-limiting autoimmune diseases include autoimmune thrombocytopenia, immune neutropenia, antihemophilic FVIII inhibitor, antiphospholipid syndrome, Kawasaki Syndrome, ANCA-associated disease, polymyositis, bullous pemphigoid, multiple sclerosis (MS), Guillain-Barre Syndrome, chronic polyneuropathy, ulcerative colitis, diabetes mellitus, autoimmune thyroiditis, Graves' opthalmopathy, rheumatoid arthritis, ulcerative colitis, primary sclerosing cholangitis, systemic lupus erythematosus (SLE), autoimmune encephalomyelitis, Hashimoto's thyroiditis, Goodpasture's syndrome, autoimmune hemolytic anemia, scleroderma with anticollagen antibodies, mixed connective tissue disease, pernicious anemia, idiopathic Addison's disease, autoimmune-associated infertility, glomerulonephrtitis (e.g., crescentic glomerulonephritis, proliferative glomerulonephritis), insulin resistance, and autoimmune diabetes mellitus (type 1 diabetes mellitus; insulin dependent diabetes mellitus). Autoimmune disease has been recognized also to encompass atherosclerosis and Alzheimer's disease. In another embodiment, the autoimmune diseases include hepatitis, autoimmune hemophilia, autoimmune lymphoproliferative syndrome (ALPS), autoimmune uveoretinitis, glomerulonephritis, agammaglobulinemia, alopecia areata, amyloidosis, ankylosing spondylitis, autoimmune angioedema, autoimmune aplastic anemia, autoimmune dysautonomia, autoimmune hyperlipidemia, autoimmune immunodeficiency, autoimmune inner ear disease (AIED), autoimmune myocarditis, autoimmune pancreatitis, autoimmune retinopathy, autoimmune urticaria, autoimmune urticarial neuropathy, autoimmune axonal neuropathy, Balo disease, Behçet's disease, Castleman disease, celiac disease, Chagas disease, chronic recurrent multifocal osteomyelitis (CRMO), Churg-Strauss syndrome, cicatricial pemphigoid, benign mucosal pemphigoid, Cogan's syndrome, cold agglutinin disease, coxsackie myocarditis, CREST disease, essential mixed cryoglobulinemia, dermatitis herpetiformis, dermatomyositis, Devic's disease (neuromyelitis optica), dilated cardiomyopathy, discoid lupus, Dressler's syndrome, endometriosis, eosinophilic angiocentric fibrosis, Eosinophilic fasciitis, Erythema nodosum, Evans syndrome, Fibrosing alveolitis, Giant cell arteritis (temporal arteritis), Hashimoto's encephalitis, Henoch-Schonlein purpura, Herpes gestationis, Idiopathic hypocomplementemic tubulointestinal nephritis, multiple myeloma, multifocal motor neuropathy, NMDA receptor antibody encephalitis, IgG4-related disease, IgG4-related sclerosing disease, inflammatory aortic aneurysm, inflammatory pseudotumour, inclusion body myositis, interstitial cystitis, juvenile arthritis, Kuttner's tumour, Lambert-Eaton syndrome, leukocytoclastic vasculitis, lichen planus, lichen sclerosus, Ligneous conjunctivitis, Linear IgA disease (LAD), Lyme disease, chronic, mediastinal fibrosis, Meniere's disease, Microscopic polyangiitis, Mikulicz's syndrome, Mooren's ulcer, Mucha-Habermann disease, multifocal fibrosclerosis, narcolepsy, optic neuritis, Ormond's disease (retroperitoneal fibrosis), palindromic rheumatism, PANDAS (pediatric autoimmune neuropsychiatric disorders associated with Streptococcus), paraneoplastic cerebellar degeneration, paraproteinemic polyneuropathies, paroxysmal nocturnal hemoglobinuria (PNH), Parry Romberg syndrome, Parsonnage-Turner syndrome, periaortitis, periarteritis, peripheral neuropathy, perivenous encephalomyelitis, POEMS syndrome, polyarteritis nodosa, Type I, II, & III autoimmune polyglandular syndromes, polymyalgia rheumatic, postpericardiotomy syndrome, progesterone dermatitis, primary biliary cirrhosis, psoriasis, psoriatic arthritis, idiopathic pulmonary fibrosis, pyoderma gangrenosum, pure red cell aplasia, Raynaud's phenomenon, reflex sympathetic dystrophy, Reiter's syndrome, relapsing polychondritis, restless legs syndrome, rheumatic fever, Riede's thyroiditis, sarcoidosis, Schmidt syndrome, scleritis, Sjogren's syndrome, sperm and testicular autoimmunity, stiff person syndrome, subacute bacterial endocarditis (SBE), Susac's syndrome, sympathetic ophthalmia, Takayasu's arteritis, Tolosa-Hunt syndrome, transverse myelitis, undifferentiated connective tissue disease (UCTD), vesiculobullous dermatosis, vitiligo, Rasmussen's encephalitis, and Waldenstrom's macroglobulinaemia.

In other embodiments, provided are methods of treating an infectious diseases, which comprise administering an effective amount of an FcRn antibody or antigen binding portion thereof to a patient in need thereof.

In some embodiments, provided are methods for reducing the serum half-life of therapeutic proteins that contain Fc domains, e.g., therapeutic antibodies or non-antibody proteins comprising Fc domains Such methods can enhance the removal of such therapeutic proteins from the bloodstream if they cause unwanted physiological effects. Examples of therapeutic proteins that may be suitable for this method include TYSABRI® (natalizumab) and AVASTIN® (bevacizumab). In some embodiments, the method causes the half-life of the therapeutic protein to be diminished by about 10%, 20%, 30%, 40%, 50%, 60%, 70%, 80%, or 90%.

In some embodiments, provided are methods for the removal of IgG-linked radioactive tracers or other antibody-drug conjugates wherein there is a desire to remove these from the circulation. In some embodiments, blocking FcRn with an IgG lowering agent would be beneficial in decreasing endogenous IgG levels to allow for enhanced pharmacokinetics and pharmacodynamics of an IgG containing therapeutic agent. In this instance, pre-treatment with an anti-FcRn antibody that is specific for the IgG binding site prior to administration of such a therapeutic agent will lower the competition derived from the endogenous IgG antibodies in monomeric form or as IgG-containing immune complexes (IC) and allow for increased protection of the administered IgG-based therapeutic agent.

Provided herein are methods of using the FcRn antibodies or antigen-binding portions thereof as set forth herein. Accordingly, provided are the FcRn antibodies or antigen-binding portions thereof as set forth herein for use in modulating an immune response or treating, preventing, or diagnosing disorders, such as immune disorders. Also provided are the FcRn antibodies or antigen-binding portions thereof as set forth herein for use in modulating the interaction between FcRn and IgG Fc to promote antibody degradation by a cell or in a subject. In some embodiments, the antibody may be an autoantibody or a therapeutic antibody. Also provided are the FcRn antibodies or antigen-binding portions thereof as set forth herein for use in treating or ameliorating an IgG-mediated disease in a subject, where the IgG-mediated disease may be those that involve pathogenic IgG antibodies and include coagulopathies, vasculitides, collagen disorders, dermatological diseases, neurological diseases, inflammatory bowel diseases, and organ-specific disorders.

Provided herein are FcRn antibodies or antigen-binding portions thereof as set forth herein for use in inhibiting immune complex (IC) binding by FcRn, inhibiting presentation of an immune complexed antigen by an antigen presenting cell (APC), or inhibiting cross-presentation of an immune complexed antigen by an antigen presenting cell (APC). Also provided are the FcRn antibodies or antigen-binding portions thereof as set forth herein for use in inhibiting secretion of an inflammatory cytokine by an antigen presenting cell (APC), where the inflammatory cytokines include, e.g., interleukin-12 (IL-12), interleukin-6 (IL-6) and interferon γ (IFN γ). Also provided are the FcRn antibodies or antigen-binding portions thereof as set forth herein for use in inhibiting T cell activation.

Provided herein are the FcRn antibodies or antigen-binding portions thereof as set forth herein for use in treating pemphigus (pemphigus vulgaris, pemphigus foliaceus or paraneoplastic pemphigus), Crohn's disease, idiopathic thrombocytopenic purpura (ITP), heparin induced thrombocytopenia (HIT), thrombotic thrombocytopenic purpura (TTP), Myasthenia Gravis (MG), and Chronic Inflammatory Demyelinating Polyneuropathy (CIDP). Additional non-limiting autoimmune diseases include autoimmune thrombocytopenia, immune neutropenia, antihemophilic FVIII inhibitor, antiphospholipid syndrome, Kawasaki Syndrome, ANCA-associated disease, polymyositis, bullous pemphigoid, multiple sclerosis (MS), Guillain-Barre Syndrome, chronic polyneuropathy, ulcerative colitis, diabetes mellitus, autoimmune thyroiditis, Graves' opthalmopathy, rheumatoid arthritis, ulcerative colitis, primary sclerosing cholangitis, systemic lupus erythematosus (SLE), autoimmune encephalomyelitis, Hashimoto's thyroiditis, Goodpasture's syndrome, autoimmune hemolytic anemia, scleroderma with anticollagen antibodies, mixed connective tissue disease, pernicious anemia, idiopathic Addison's disease, autoimmune-associated infertility, glomerulonephrtitis (e.g., crescentic glomerulonephritis, proliferative glomerulonephritis), insulin resistance, and autoimmune diabetes mellitus (type 1 diabetes mellitus; insulin dependent diabetes mellitus). Autoimmune disease has been recognized also to encompass atherosclerosis and Alzheimer's disease. In another embodiment, the autoimmune diseases include hepatitis, autoimmune hemophilia, autoimmune lymphoproliferative syndrome (ALPS), autoimmune uveoretinitis, glomerulonephritis, agammaglobulinemia, alopecia areata, amyloidosis, ankylosing spondylitis, autoimmune angioedema, autoimmune aplastic anemia, autoimmune dysautonomia, autoimmune hyperlipidemia, autoimmune immunodeficiency, autoimmune inner ear disease (AIED), autoimmune myocarditis, autoimmune pancreatitis, autoimmune retinopathy, autoimmune urticaria, autoimmune urticarial neuropathy, autoimmune axonal neuropathy, Balo disease, Behçet's disease, Castleman disease, celiac disease, Chagas disease, chronic recurrent multifocal osteomyelitis (CRMO), Churg-Strauss syndrome, cicatricial pemphigoid, benign mucosal pemphigoid, Cogan's syndrome, cold agglutinin disease, coxsackie myocarditis, CREST disease, essential mixed cryoglobulinemia, dermatitis herpetiformis, dermatomyositis, Devic's disease (neuromyelitis optica), dilated cardiomyopathy, discoid lupus, Dressler's syndrome, endometriosis, eosinophilic angiocentric fibrosis, Eosinophilic fasciitis, Erythema nodosum, Evans syndrome, Fibrosing alveolitis, Giant cell arteritis (temporal arteritis), Hashimoto's encephalitis, Henoch-Schonlein purpura, Herpes gestationis, Idiopathic hypocomplementemic tubulointestitial nephritis, multiple myeloma, multifocal motor neuropathy, NMDA receptor antibody encephalitis, IgG4-related disease, IgG4-related sclerosing disease, inflammatory aortic aneurysm, inflammatory pseudotumour, inclusion body myositis, interstitial cystitis, juvenile arthritis, Kuttner's tumour, Lambert-Eaton syndrome, leukocytoclastic vasculitis, lichen planus, lichen sclerosus, Ligneous conjunctivitis, Linear IgA disease (LAD), Lyme disease, chronic, mediastinal fibrosis, Meniere's disease, Microscopic polyangiitis, Mikulicz's syndrome, Mooren's ulcer, Mucha-Habermann disease, multifocal fibrosclerosis, narcolepsy, optic neuritis, Ormond's disease (retroperitoneal fibrosis), palindromic rheumatism, PANDAS (pediatric autoimmune neuropsychiatric disorders associated with Streptococcus), paraneoplastic cerebellar degeneration, paraproteinemic polyneuropathies, paroxysmal nocturnal hemoglobinuria (PNH), Parry Romberg syndrome, Parsonnage-Turner syndrome, periaortitis, periarteritis, peripheral neuropathy, perivenous encephalomyelitis, POEMS syndrome, polyarteritis nodosa, Type I, II, & III autoimmune polyglandular syndromes, polymyalgia rheumatic, postpericardiotomy syndrome, progesterone dermatitis, primary biliary cirrhosis, psoriasis, psoriatic arthritis, idiopathic pulmonary fibrosis, pyoderma gangrenosum, pure red cell aplasia, Raynaud's phenomenon, reflex sympathetic dystrophy, Reiter's syndrome, relapsing polychondritis, restless legs syndrome, rheumatic fever, Riede's thyroiditis, sarcoidosis, Schmidt syndrome, scleritis, Sjogren's syndrome, sperm and testicular autoimmunity, stiff person syndrome, subacute bacterial endocarditis (SBE), Susac's syndrome, sympathetic ophthalmia, Takayasu's arteritis, Tolosa-Hunt syndrome, transverse myelitis, undifferentiated connective tissue disease (UCTD), vesiculobullous dermatosis, vitiligo, Rasmussen's encephalitis, or Waldenstrom's macroglobulinaemia.

In the methods described herein, a therapeutically effective amount of an antibody or antigen-binding portion thereof set forth herein may be administered in combination (e.g., simultaneously, sequentially, or separately) with other agents, drugs, or hormones. In some embodiments, the other agents, drugs, or hormones may be small molecules, peptides, or proteins, including antibodies or antigen-binding fragments. In some embodiments, the other agents, drugs, or hormones may be administered in the same composition, or in separate compositions. In some embodiments, the other agents, drugs, or hormones are known agents, compounds, or hormones for treating the disorders, diseases, or conditions described herein. For example, in some embodiments, the other agent may be a monoclonal antibody therapy for the treatment of an immune-mediated disease. In other embodiments, the other agent may be an inhibitor of the complement system. For example, combinations directed at the Fc gamma receptor and FcRn are described in WO 2015/164605, incorporated herein by reference in its entirety.

In some embodiments, the other agents, drugs, or hormones are immunosupressant agents, immunostimulatory agents, immunomodulators, or a combination thereof. In some embodiments, the other agents, drugs, or hormones are intravenous Ig therapy; nonsteroidal anti-inflammatory drugs (NSAID); corticosteroids; cyclosporins, rapamycins, ascomycins, or their immunosuppressive analogs, e.g., cyclosporinA, cyclosporin G, FK-506, rapamycin, 40-0-(2-hydroxy)ethyl-rapamycin; cyclophosphamide; azathioprene; methotrexate; microphenyolate; brequinar; FTY 720; leflunomide; mnizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD 58 or their ligands; other immunomodulatory compounds, e.g. CTLA4Ig; other adhesion molecule inhibitors, e.g., mAbs or low molecular weight inhibitors including selectin antagonists and VLA-4 antagonists; immunomodulatory cytokines, e.g., alpha-interferon, gamma-interferon, or tumor necrosis factor-alpha; or immunostimulatory cytokines, e.g., interleukin-2.

Provided herein are methods of measuring the level of anti-FcRn antibody in a subject after administration of an anti-FcRn antibody, the method comprising obtaining whole blood from the subject after administration of an anti-FcRn antibody, wherein the whole blood comprises monocytes, and measuring the monocyte cell surface FcRn expression level. Without being limited to any specific theory, it has been shown that there is a correlation between monocyte cell surface levels of FcRn and presence of anti-FcRn antibodies. The monocyte cell surface FcRn expression level may be measured by any method known in the art, and may include, e.g., geomean fluorescence intensity.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Example 1

Humanization of Variable Domains

Heavy and light chain variable regions suitable for human administration were designed based on a mouse monoclonal antibody selected for its ability to bind to FcRn and block the binding of FcRn and IgG Fc. The mouse antibody does not substantially bind to human serum albumin Using a model of the monoclonal antibody based on existing antibody structures, variable region frameworks for the human antibody were designed from segments of human V regions. In order to minimize potential immunogenicity, several variants were designed with amino acids selected at certain framework locations designed to remove human T cell epitopes.

Heavy and light chain V region genes were constructed from overlapping oligonucleotides assembled into full length genes using the ligase chain reaction (LCR), followed by amplification and addition of restriction sites suitable for cloning.

Four heavy chains variants were constructed with a human IgG4 constant region. The variants are designated $V_H1$, $V_H2$, $V_H3$, and $V_H4$. The amino acid sequences of the variable domains of the heavy chain variants are represented by SEQ ID NOS:12, 14, 16, and 18 respectively. The oligonucleotide sequences of the variable domains of the heavy chain variants are represented by SEQ ID NOS:11, 13, 15, and 17 respectively. FIG. 1 shows an alignment of the four variants. Four light chain variants were constructed and expressed as human kappa chains. The variants are designated Vκ1, Vκ2, Vκ3, and Vκ5. The amino acid sequences of the light chain variants are represented by SEQ ID NOS:20, 22, 24, and 26 respectively. The oligonucleotide sequences of the variable domains of the light chain variants are represented by SEQ ID NOS:19, 21, 23, and 25 respectively. FIG. 2 shows an alignment of the four variants.

Antibodies were expressed as whole IgGs by cloning V region genes into a mammalian expression vector with an upstream cytomegalovirus immediate/early promoter/enhancer, an immunoglobulin signal sequence, and immunoglobulin constant region. The vectors were transfected into HEK EBNA cells, expression quantified, and antibodies purified on Protein A columns.

All 16 heavy-light chain combinations of the four heavy chain and four light chain variants were expressed by transient transfection into HEK EBNA cells. The antibodies were purified on Protein A sepharose columns and quantified. As indicated above, FcRn resides primarily in the early acidic endosomes where it captures endocytosed IgG by binding to the Fc region at a low pH. To block binding of FcRn to Fc of endocytosed IgG, it is also desirable that the FcRn antibodies will bind to FcRn exposed to the intercellular milieu at physiologic pH (e.g., pH 7.4). Therefore, the binding of the purified antibodies to FcRn was assessed in a competition ELISA assay at pH 6.0 and pH 7.4.

For the ELISA, a Nunc Immuno MaxiSorp 96 well flat bottom microtitre plate was pre-coated overnight at pH 7.4 with an FcRn antibody specific for an albumin-binding epitope distinct from the Fc-binding region. The following day 1 µg/ml recombinant human FcRn (Sino Biological Inc.

Cat. No. CT009-H08H) diluted in PBS pH 7.4 was added to the wells and incubated for 1 hour at 37° C. A four-fold dilution series of control or test IgG4 antibodies from 25 μg/ml to 0.0015 μg/ml was premixed with a constant concentration of biotinylated parent murine antibody, added to the plates and incubated for 1 hour at 37° C. The binding of the biotinylated mAb was detected with streptavidin-HRP and TMB substrate. Absorbance was read at 450 nm and the binding curves plotted. The binding of the 16 combinations was tested at both pH 7.4 and pH 6.0 and quantified by comparison to the parent murine antibody, as shown in Table 2.

TABLE 2

Relative Affinity

| Variant | Average titer (μg/ml) | Average relative IC$_{50}$ (relative to chimeric parent IgG$_4$) | |
|---|---|---|---|
| | | pH 7.4 | pH 6 |
| murine parent | 48.11 | 1 | 1 |
| V$_H$1/Vκ1 | 82.19 | 1.14 | 1.09 |
| V$_H$1/Vκ2 | 48.54 | 1.19 | 0.82 |
| V$_H$1/Vκ3 | 39.52 | 1.98 | 1.56 |
| V$_H$1/Vκ5 | 58.61 | 2.02 | 1.75 |
| V$_H$2/Vκ1 | 113.52 | 1.24 | 0.92 |
| V$_H$2/Vκ2 | 100.74 | 1.39 | 1.01 |
| V$_H$2/Vκ3 | 88.11 | 1.93 | 1.37 |
| V$_H$2/Vκ5 | 9.43 | 2.49 | 2.49 |
| V$_H$3/Vκ1 | 103.85 | 1.40 | 1.26 |
| V$_H$3/Vκ2 | 130.82 | 1.30 | 1.07 |
| V$_H$3/Vκ3 | 106.68 | 2.01 | 1.73 |
| V$_H$3/Vκ5 | 121.78 | 2.60 | 2.26 |
| V$_H$4/Vκ1 | 46.20 | 1.36 | 1.21 |
| V$_H$4/Vκ2 | 34.22 | 1.28 | 1.02 |
| V$_H$4/Vκ3 | 118.37 | 1.77 | 1.70 |
| V$_H$4/Vκ5 | 107.84 | 1.98 | 2.43 |

Example 2

Affinity Maturation

To improve binding affinity at acidic and physiologic pH, the heavy and light chain variable domain CDR3 regions were mutated and screened in scFv form at pH 6.0 and pH 7.4. To prepare scFvs, genes encoding V$_H$ and Vκ were assembled with a 15 amino acid (G$_4$S)$_3$ linker using overlap PCR. The scFv sequence was cloned into a phagemid vector as a gene 3 fusion protein, and the vector transformed into E. coli (TG1). The affinity maturation process was conducted using the V$_H$1 and Vκ1 variants. For screening, a library of heavy chain CDR3s in V$_H$1 was combined with the humanized parental Vκ1 light chain and a library of light chain CDR3s in Vκ1 was combined with the humanized parental V$_H$1 heavy chain.

Amino acid sequence variation was introduced into the heavy chain CDR3H region at amino acid positions 98-103 (a.a. 98-102 of CDR3H and a.a. 103 of FW4) using the oligonucleotide sequence KNCNNCNNCNNCSVCNW-CYGG (SEQ ID NO:71) which provided for selected amino acids at each position, as follows: a.a. 98: A, C, D, F, G, S, V, Y; a.a. 99: A, C, D, F, G, H, I, L, N, P, R, S, T, V, Y; a.a. 100: A, C, D, F, G, H, I, L, N, P, R, S, T, V, Y; a.a. 100a: A, C, D, F, G, H, I, L, N, P, R, S, T, V, Y; a.a. 101: A, D, G, H, P, R; a.a. 102: D, F, H, I, L, N, V, Y; a.a. 103: R, W Amino acid sequence variation was introduced into the light chain CDR3L region at amino acid positions 89-97 using the oligonucleotide sequence TGTMRSVMGTVSKRSRRCW-MCYYCBWCRYCTTC (SEQ ID NO:72), which provided for selected amino acids at each position, as follows: a.a. 88: C; a.a. 89: H, K, N, Q, R, S; a.a. 90: A, E, K, P, Q, T; a.a. 91: C, S, W, Y; a.a. 92: C, D, E, G, W, Y; a.a. 93: D, G, N, S; a.a. 94: N, S, T, Y; a.a. 95: F, L, P, S; a.a. 96: D, F, H, L, V, Y; a.a. 97: A, I, T, V.

For each CDR, a library of about 5-10×10$^7$ phage containing on the order of 3-6×10$^6$ DNA sequences (i.e., about 10-20 copies of each DNA sequence were represented) was screened for binding to soluble antigen. Specifically, the phage libraries were mixed with soluble biotinylated FcRn, followed by capture of FcRn-antibody phage complexes on streptavidin-coated beads. To obtain antibodies that bind to FcRn in acidic endosomes as well as at physiologic pH, successive rounds of library screening were conducted at alternating pH. Also, to increase the stringency of each successive screening round, the concentration of FcRn antigen was reduced. The initial selection round was conducted with a target concentration of 25 nM antigen at pH 6.0. The second round was conducted at 2.5 nM antigen concentration at pH 7.4. The third round was conducted at 0.25 nM antigen concentration at pH 6.0.

A total of about 60 scFv antibodies from the V$_H$ CDR3 and V$_L$ CDR3 libraries were selected for further study. The scFv antibodies were prepared from bacterial periplasmic extracts, and tested by competition ELISA at pH 6.0 and pH 7.4. In the competition ELISA, the scFv antibody fragments were competed against biotinylated parent murine antibody for binding to immobilized FcRn. As in the ELISA used to test humanized variants, a 96 well flat bottom microtitre plate was pre-coated with 1 μg/ml of an FcRn antibody specific for an albumin-binding epitope distinct from the Fc-binding region. Binding was determined at pH 7.4 and pH 6.0. FIG. 3 shows increased binding affinity for three of the affinity matured heavy chains (H1, H3, E7) expressed as scFv with the humanized parental Vκ1 light chain, and one of the affinity matured light chains (E8) expressed as scFv with the parental V$_H$1 heavy chain, at both pH 6.0 and pH 7.4. Table 3 shows improved binding observed for 15 heavy chains and two light chains, quantified by comparison with the parent murine antibody.

TABLE 3

Relative Affinity

| Variant | SEQ ID NO | CDR Sequence | Fold decrease in IC$_{50}$ (relative to humanized parent scFV) | |
|---|---|---|---|---|
| | | | pH 7.4 | pH 6 |
| murine parent | | | 1 | 1 |
| H1 V$_H$1 | 52 | STTVSPPPL(W) | 36.42 | 17.09 |
| H3 V$_H$1 | 56 | STTVRPPGI(W) | 50.00 | 25.51 |
| E7 V$_H$1 | 42 | STTVSPPHL(W) | 37.44 | 16.41 |

TABLE 3-continued

| | | | Relative Affinity | |
| | | | Fold decrease in $IC_{50}$ (relative to humanized parent scFV) | |
| Variant | SEQ ID NO | CDR Sequence | pH 7.4 | pH 6 |
| --- | --- | --- | --- | --- |
| A7 $V_H1$ | 30 | STTVSPPPI(W) | 19.98 | 16.97 |
| H4 $V_H1$ | 58 | STTVSAPGV(W) | 9.29 | 6.50 |
| E4 $V_H1$ | 40 | STTVHPDHN(W) | 16.78 | 3.65 |
| C4 $V_H1$ | 34 | STTVAPPRL(W) | 24.44 | 18.58 |
| A4 $V_H1$ | 28 | STTVSPADF(R) | 7.18 | 5.04 |
| C7 $V_H1$ | 36 | STTVHPDRN(W) | 10.12 | 8.50 |
| H2 $V_H1$ | 54 | STTVAPPAH(W) | 23.78 | 14.20 |
| G7 $V_H1$ | 48 | STTVAPPGH(W) | 30.79 | 17.66 |
| D1 $V_H1$ | 38 | STTVSPPAL(W) | 26.88 | 15.06 |
| F7 $V_H1$ | 44 | STTVAPPPL(W) | 26.35 | 16.43 |
| G4 $V_H1$ | 46 | STTVSPPHL(W) | 29.01 | 18.89 |
| G9 $V_H1$ | 50 | STTVSPPRV(W) | 25.27 | 21.71 |
| murine parent | | | 1 | 1 |
| E8 Vκ1 | 66 | CHQYYSTPYT | 11.66 | 7.21 |
| B7 Vκ1 | 63 | CHQYYNTPYT | 6.58 | 6.38 |

Substantial improvements in binding were measured for scFvs containing affinity matured heavy chain CDR3s in the $V_H1$ framework. Therefore these heavy chains were carried forward for testing in combination with improved light chains. As shown in Example 1 above, the Vκ1 and Vκ2 light chains demonstrated similar binding when paired with $V_H1$ (and other $V_H$ variants), and the Vκ2 framework was predicted to be less immunogenic than Vκ1. Therefore Vκ1 and Vκ2-based light chains containing affinity matured CDR3 were carried forward for testing in combination with improved heavy chains.

Example 3

Development of IgG Antibodies

Eight affinity matured heavy chains (A8, C4, F7, G4, G7, G9, H1, and H3) were selected and expressed with a humanized light chain (Vκ1 or Vκ2) containing CDR3 of E8. The sixteen combinations were expressed as bivalent IgG4 antibodies by transient transfection of HER cells, followed by purification of the IgG4 antibodies. The affinity matured heavy chains were also expressed in combination with humanized but non-affinity matured light chains and certain affinity matured light chains were expressed with humanized but non-affinity matured heavy chains.

Example 4

Figure 4:
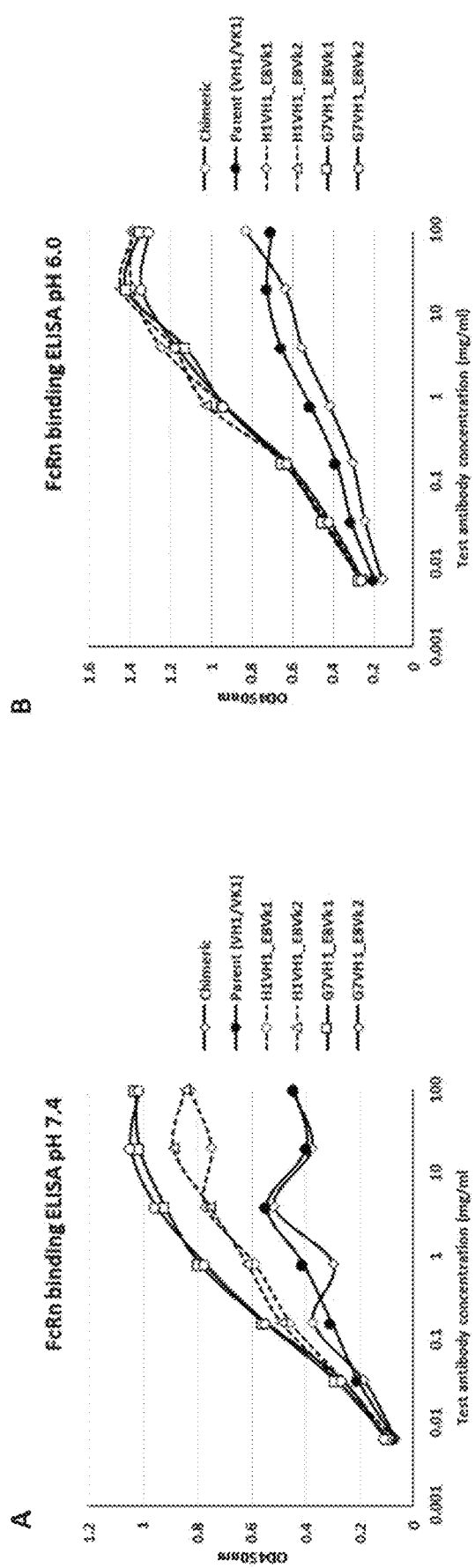
FIG. 4 shows a direct binding assay comparing IgG4 antibodies comprising humanized parental ($V_H1$Vκ1), or affinity matured (H1$V_H1$_E8Vκ1, H1$V_H1$_E8Vκ2, G7$V_H1$_E8Vκ1, G7$V_H1$_E8Vκ2) heavy and light chains, and the chimeric parent murine antibody. Antibodies were reacted with immobilized FcRn at pH 7.4 (A) and pH 6.0 (B), and bound antibody detected with anti-human kappa-HRP.

Antigen Binding and Blocking Characteristics of IgG4 Antibodies as Determined by ELISA Affinity matured IgG was compared to humanized parental $V_H1$/Vκ1 IgG by direct binding ELISA. A Nunc Immuno MaxiSorp 96 well flat bottom microtitre plate was pre-coated overnight at pH 7.4 with an FcRn antibody specific for an albumin-binding epitope distinct from the Fc-binding region. The following day 1 µg/ml recombinant human FcRn (Sino Biological Inc. Cat. No. CT009-H08H) diluted in PBS pH 7.4 was added to the wells and incubated for 1 hour at 37° C., followed by blocking of non-specific binding with 4% milk/PBS. Titrated humanized parental or affinity matured IgGs were added to wells followed by detection of bound antibody using anti-human kappa-HRP. FIG. 4 shows increased binding of H1$V_H1$_E8Vκ1, H1$V_H1$_E8Vκ2, G7$V_H1$_E8Vκ1, and G7$V_H1$_E8Vκ2 IgG to immobilized FcRn compared to the humanized parental $V_H1$Vκ1 IgG or chimeric parent murine antibody.

The IgG4 antibodies also were tested for antigen binding in a competition ELISA at pH 6.0 and pH 7.4. A Nunc Immuno MaxiSorp 96 well flat bottom microtitre plate (Fisher, cat. no. DIS-971-030J) was pre-coated with 1 µg/ml of an FcRn antibody specific for an albumin-binding epitope distinct from the Fc-binding region overnight at pH 7.4. The following day, 1 µg/ml recombinant human FcRn (Sino Biological Inc. cat. no. CT009-H08H) diluted in PBS pH 7.4 was added to the wells and incubated for 1 hour at 37° C. After washing the plates 3× with PBST pH 7.4, the plates were blocked with PBSM pH 7.4 for 1 hour at 37° C. From this point onwards, all wash and incubation steps were performed at the chosen assay pH (pH 6.0 or 7.4). After washing 3× with PBST, a four-fold dilution series of tested antibodies from 25 µg/ml to 0.006 µg/ml final concentration was premixed with a constant concentration of biotinylated parent murine antibody (0.4 µg/ml, final concentration), added to the FcRn coated plates and incubated for 1 hour at 37° C. Following 3×PBST washes, the binding of the biotinylated mAb was detected with streptavidin-HRP (Sigma, cat. no. S5512) and TMB substrate (Invitrogen, cat. no. 00-2023). The reaction was stopped with 3 M HCl, absorbance read at 450 nm on a Dynex Technologies MRX TC II plate reader and the binding curves plotted.

Figure 5:
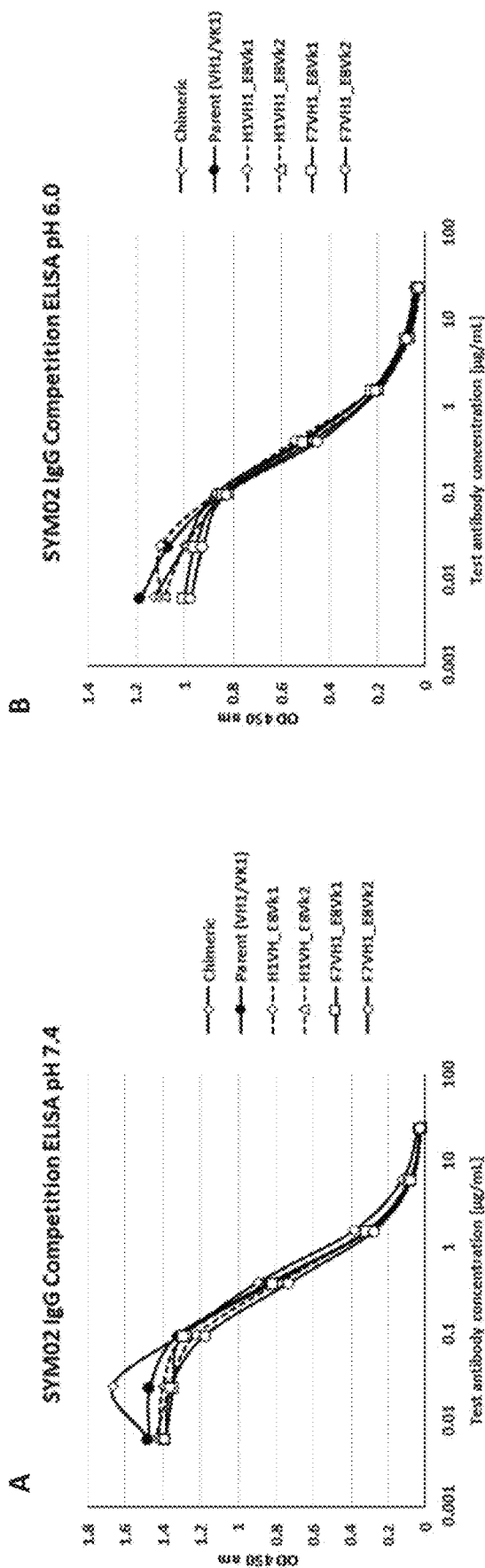
FIG. 5 shows a competitive ELISA comparing IgG4 antibodies comprising humanized parental ($V_H1$Vκ1), or affinity matured (H1$V_H1$_E8Vκ1, H1$V_H1$_E8Vκ2, F7$V_H1$_E8Vκ1, F7$V_H1$_E8Vκ2) heavy and light chains, and the chimeric parent murine antibody. Test antibodies were competed against the biotinylated parent murine antibody at pH 7.4 (A) and pH 6.0 (B), and bound biotinylated parent murine antibody detected by streptavidin-HRP.

As shown in FIG. 5 for four of the antibodies (H1V$_H$1_E8Vκ1, H1V$_H$1_E8Vκ2, F7V$_H$1_E8Vκ1, V$_H$1_E8Vκ2), the affinity matured IgGs behaved similarly to the chimeric parent murine antibody and the humanized parental V$_H$1Vκ1 antibody in the competition ELISA.

Figure 6:
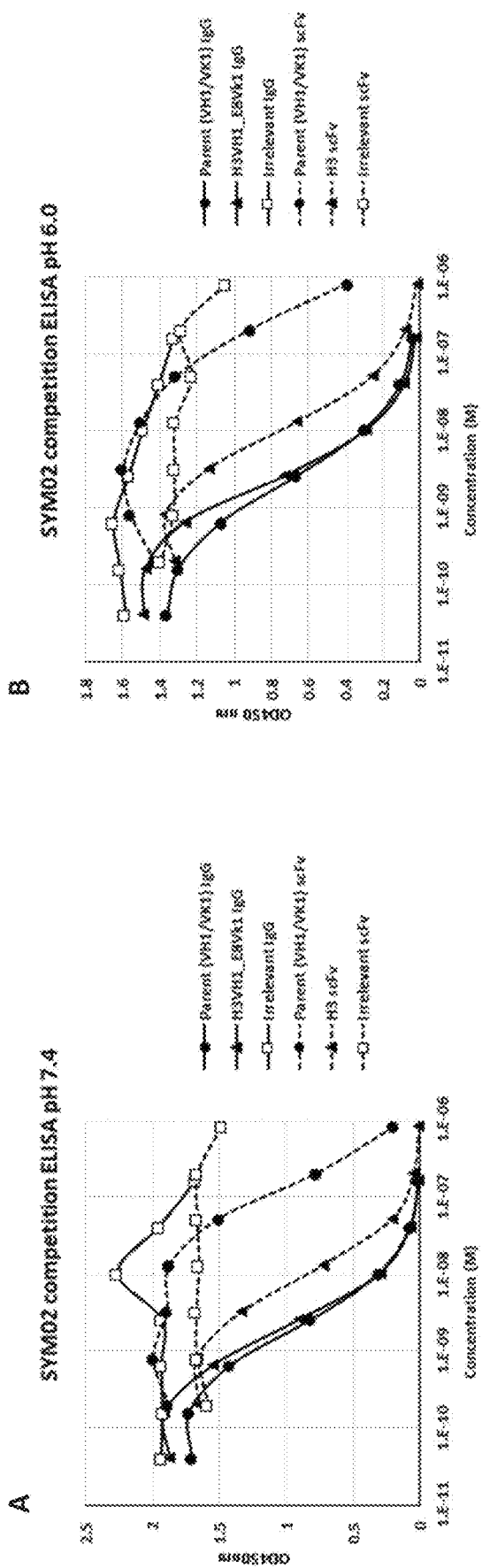
FIG. 6 shows a competitive ELISA comparing monovalent scFv and divalent IgG antibodies, comprising humanized parental ($V_H1$Vκ1) or affinity matured (H3$V_H1$_E8Vκ1) variable domains Test antibodies were competed against biotinylated parent murine antibody at pH 7.4 (A) and pH 6.0 (B), and bound biotinylated parent murine antibody detected by streptavidin-HRP.

The competition ELISA was also used to compare certain combinations of affinity matured heavy and light chains expressed in monovalent (scFv) or bivalent (IgG) form with the humanized parental V$_H$1Vκ1. FIG. 6 compares binding of H3V$_H$1_E8Vκ1 IgG, H3V$_H$1_Vκ1 scFv, V$_H$1Vκ1 IgG, and V$_H$1Vκ1 scFv at both pH 7.4 and pH 6.0. In scFv form, the affinity matured H3V$_H$1_Vκ1 scFv demonstrated significantly improved binding compared to the V$_H$1Vκ1 scFv parent. Also, compared to the scFv form, when expressed as bivalent IgG, both H3V$_H$1_E8Vκ1 IgG and V$_H$1Vκ1 demonstrated improved binding.

Additional combinations of humanized affinity matured heavy chains and humanized affinity matured light chains were tested in the competition ELISA. Combinations of humanized affinity matured heavy chains and humanized non-affinity matured light chains also were tested. The results obtained are summarized in Tables 4 and 5, which show the average relative IC$_{50}$ values for experiments performed at pH 7.4 and pH 6.0 and the number (n) of experiments. IC$_{50}$ values of the combinations were normalized to the chimeric parent murine antibody tested on the same plate.

TABLE 4

| Humanized affinity matured combination | pH 7.4 Average relative IC$_{50}$ | pH 6.0 Average relative IC$_{50}$ |
| --- | --- | --- |
| Chimeric | 1.0 | 1.0 |
| VH1/Vκ1 | 0.87 | 0.81 |
| VH1_G4/Vκ1_E8 | 1.18 (n = 2) | 1.53 (n = 2) |
| VH1_F7/Vκ1_E8 | 0.78 (n = 1) | 1.38 (n = 2) |
| VH1_H1/Vκ1_E8 | 0.84 (n = 1) | 1.13 (n = 3) |
| VH1_G7/Vκ1_E8 | 0.87 (n = 1) | 0.85 (n = 3) |
| VH1_A8/Vκ1_E8 | 0.74 (n = 1) | 0.75 (n = 3) |
| VH1_G9/Vκ1_E8 | 0.82 (n = 1) | 0.93 (n = 3) |
| VH1_C4/Vκ1_E8 | 0.95 (n = 2) | 0.91 (n = 2) |
| VH1_H3/Vκ1_E8 | 1.01 (n = 1) | 0.57 (n = 2) |
| VH1_G4/Vκ2_E8 | 1.10 (n = 1) | 1.23 (n = 2) |
| VH1_F7/Vκ2_E8 | 0.98 (n = 1) | 1.33 (n = 2) |
| VH1_H1/Vκ2_E8 | 0.93 (n = 1) | 1.04 (n = 3) |
| VH1_G7/Vκ2_E8 | 0.88 (n = 1) | 0.80 (n = 3) |
| VH1_A8/Vκ2_E8 | 0.84 (n = 1) | 0.71 (n = 3) |
| VH1_G9/Vκ2_E8 | 1.58 (n = 1) | 1.03 (n = 3) |
| VH1_C4/Vκ2_E8 | 1.47 (n = 2) | 0.84 (n = 2) |
| VH1_H3/Vκ2_E8 | 0.73 (n = 1) | 0.58 (n = 2) |

TABLE 5

| Combination | pH 7.4 Average relative IC$_{50}$ | pH 6.0 Average relative IC$_{50}$ |
| --- | --- | --- |
| Chimeric | 1.0 | 1.0 |
| VH1/Vκ1 | 1.06 | 0.92 |
| VH1_H3/Vκ1 | 0.62 (n = 3) | 0.57 (n = 2) |
| VH1_C4/Vκ1 | 0.59 (n = 3) | 0.60 (n = 3) |
| VH1_G4/Vκ1 | 0.86 (n = 3) | 0.81 (n = 3) |
| VH1_G9/Vκ1 | n.d. | n.d. |
| VH1_G7/Vκ1 | n.d. | n.d. |
| VH1_F7/Vκ1 | 0.66 (n = 3) | 0.76 (n = 3) |
| VH1_H1/Vκ1 | 0.88 (n = 3) | 0.80 (n = 2) |
| VH1_A8/Vκ1 | 0.89 (n = 3) | 0.87 (n = 3) | n.d. = not done

The binding of humanized affinity matured antibodies to FcRn was further assessed in a competition ELISA assay with whole human IgG at pH 6.0. A Nunc Immuno Max- iSorp 96 well flat bottom microtitre plate (Fisher, cat. no. DIS-971-030J) was pre-coated overnight at pH 7.4 with 1 µg/ml of an FcRn antibody specific for an albumin-binding epitope distinct from the Fc-binding region of FcRn. The following day, 0.5 µg/ml recombinant human FcRn (Sino Biological Inc. cat. no. CT009-H08H) diluted in PBS pH 7.4 was added to the wells and incubated for one hour at 37° C. After washing the plates 3× with PBST pH 7.4, the plates were blocked with PBSM pH 7.4 for one hour at 37° C. From this point onwards, all wash and incubation steps were performed at assay pH 6.0. After washing 3× with PBST, a three-fold dilution series of tested antibodies from 25 µg/ml to 0.034 µg/ml final concentration was premixed with a constant concentration of biotinylated human serum IgG (Sigma, cat. no. 14506, 25 µg/ml final concentration), added to the plates and incubated for one hour at 37° C. Following 3×PBST washes, the binding of the biotinylated IgG was detected with streptavidin-HRP (Sigma, cat. no. S5512) and TMB substrate (Invitrogen, cat. no. 00-2023). The reaction was stopped with 3 M HCl, absorbance read at 450 nm on a Dynex Technologies MRX TC II plate reader and binding curves plotted.

The binding of combinations of humanized affinity matured heavy chains with humanized affinity matured light chains to FcRn at pH 6.0 in the presence of human serum IgG was compared to that of the chimeric parent murine antibody. The results are summarized in Table 6. Average relative IC$_{50}$ values were normalized to the chimeric antibody tested on the same plate.

TABLE 6

| Combinations | Average relative IC$_{50}$ | Number of experiments |
| --- | --- | --- |
| Chimeric | 1.00 | — |
| VH1/Vκ1 | 0.80 | 12 |
| VH1_G4/Vκ1_E8 | 1.04 | 3 |
| VH1_F7/Vκ1_E8 | 0.94 | 3 |
| VH1_H1/Vκ1_E8 | 0.92 | 3 |
| VH1_G7/Vκ1_E8 | 0.80 | 3 |
| VH1_A8/Vκ1_E8 | 0.94 | 3 |
| VH1_G9/Vκ1_E8 | 0.85 | 3 |
| VH1_C4/Vκ1_E8 | 0.72 | 3 |
| VH1_H3/Vκ1_E8 | 0.98 | 3 |
| VH1_G4/Vκ2_E8 | 0.91 | 3 |
| VH1_F7/Vκ2_E8 | 0.48 | 3 |
| VH1_H1/Vκ2_E8 | 0.90 | 3 |
| VH1_G7/Vκ2_E8 | 0.84 | 3 |
| VH1_A8/Vκ2_E8 | 0.79 | 3 |
| VH1_G9/Vκ2_E8 | 0.81 | 3 |
| VH1_C4/Vκ2_E8 | 0.53 | 3 |
| VH1_H3/Vκ2_E8 | 0.77 | 3 |

The binding of combinations of humanized affinity matured heavy chains with humanized non-affinity matured light chains to FcRn at pH 6.0 in the presence of human serum IgG was compared to that of the parent murine FcRn antibody. The results are summarized in Table 7. Average relative IC$_{50}$ values were normalized to the parent murine antibody tested on the same plate.

TABLE 7

| Combinations | Average relative IC$_{50}$ | Number of experiments |
| --- | --- | --- |
| Parent | 1.00 | — |
| VH1_H1/Vκ2_E8 | 0.66 | 2 |
| VH1_H1/Vκ1 | 0.73 | 2 |
| VH1_H3/Vκ2_E8 | 0.69 | 3 |

TABLE 7-continued

| Combinations | Average relative IC$_{50}$ | Number of experiments |
|---|---|---|
| VH1__H3/Vκ1 | 0.41 | 3 |
| VH1__G9/Vκ2__E8 | 0.60 | 3 |
| VH1__G9/Vκ1 | 0.61 | 3 |
| VH1__C4/Vκ2__E8 | 0.66 | 2 |
| VH1__C4/Vκ1 | 0.65 | 2 |
| VH1__G4/Vκ2__E8 | 1.20 | 2 |
| VH1__G4/Vκ1 | 0.87 | 2 |
| VH1__F7/Vκ2__E8 | 0.95 | 2 |
| VH1__F7/Vκ1 | 0.91 | 2 |
| VH1__G7/Vκ2__E8 | 0.98 | 2 |
| VH1__G7/Vκ1 | 0.90 | 2 |
| VH1__A8/Vκ2__E8 | 0.52 | 2 |
| VH1__A8/Vκ1 | 0.53 | 2 |

Additional data relating to some combinations of humanized affinity matured heavy and light chains as well as some combinations of humanized affinity matured heavy chains paired with humanized non-affinity matured light chains is shown in Table 8 below.

TABLE 8

| hIgG competition | pH 6.0 relative IC$_{50}$ to chimeric | pH 6.0 relative IC$_{50}$ to parent | hIgG competition | pH 6.0 relative IC$_{50}$ to chimeric | pH 6.0 relative IC$_{50}$ to parent | hIgG competition | pH 6.0 relative IC$_{50}$ to chimeric | pH 6.0 relative IC$_{50}$ to parent |
|---|---|---|---|---|---|---|---|---|
| Chimeric | 1.00 | | chimeric | 1.00 | | chimeric | 1.00 | |
| VH1/VK1(PARENT) | 0.79 | 1.00 | VH1/VK1(PARENT) | 0.86 | 1.00 | VH1/VK1(PARENT) | 0.84 | 1.00 |
| G7/E8VK1 | 0.72 | 0.91 | A8/E8VK1 | 0.74 | 0.86 | H3/VK1 | 0.46 | 0.70 |
| G7/E8VK2 | 0.85 | 1.07 | A8/E8VK2 | 0.53 | 0.61 | F7/VK1 | 0.73 | 1.09 |
| G9/E8VK1 | 0.68 | 0.86 | H3/E8VK1 | 0.63 | 0.73 | C4/VK1 | 0.55 | 0.82 |
| G9/E8VK2 | 0.64 | 0.81 | H3/E8VK2 | 0.55 | 0.63 | | | |

Example 5

Determination of mAb Binding Kinetics Using Surface Plasmon Resonance

Antibodies were diluted into 10 mM NaAc, pH 4.5, and immobilized onto BIACORE® CM5 chips to RU levels of approximately 500-1000. Analysis was performed by injection of FcRn at concentrations of 12-800 nM in 1×PBS-P at pH 7.4 or pH 6.0. Table 9 shows kinetic data fitted using a 1:1 Langmuir model.

TABLE 9

| | Binding kinetics of anti-human FcRn mAbs | | | | | |
|---|---|---|---|---|---|---|
| | pH 7.4 | | | pH 6.0 | | |
| Anti-FcRn mAbs | Ka (1/Ms) | Kd (1/s) | KD (nM) | Ka (1/Ms) | Kd (1/s) | KD (nM) |
| G4V$_H$1E8Vκ2 | 5.43E+04 | 5.44E−04 | 13.1 | 2.29E+05 | 2.98E−04 | 1.3 |
| H1V$_H$1E8Vκ2 | 4.38E+04 | 4.37E−04 | 12.1 | 4.67E+05 | 3.25E−04 | 0.7 |
| G7V$_H$1E8Vκ2 | 4.81E+04 | 5.35E−04 | 14.6 | 2.52E+05 | 3.10E−04 | 1.3 |
| A8V$_H$1E8Vκ2 | 4.38E+04 | 6.79E−04 | 18.2 | 3.19E+05 | 4.38E−04 | 1.4 |
| G9V$_H$1E8Vκ2 | 1.01E+05 | 4.11E−04 | 4.1 | 6.24E+05 | 3.49E−04 | 0.6 |
| H3V$_H$1E8Vκ2 | 1.14E+05 | 5.21E−04 | 4.8 | 7.00E+05 | 3.65E−04 | 0.5 |
| H3V$_H$1Vκ1 | 1.97E+05 | 2.12E−04 | 1.1 | 7.43E+05 | 1.32E−04 | 0.2 |
| C4V$_H$1Vκ1 | 1.14E+05 | 2.47E−04 | 2.2 | 4.56E+05 | 1.63E−04 | 0.4 |
| chimeric murine parent | 1.37E+05 | 3.54E−04 | 2.7 | 5.61E+05 | 2.45E−04 | 0.4 |

In a further study, affinities of IgGs comprising affinity matured heavy and light chains were compared to the humanized parental V$_H$1/Vκ1 antibody by BIACORE®. Antibodies were captured on a CM5 chip coated with protein A and analyte (FcRn) flowed over the surface. As indicated below in Table 10, antibodies comprising affinity matured heavy and light chains displayed affinities similar to the humanized parental V$_H$1/Vκ1 antibody.

TABLE 10

| | Binding kinetics of anti-human FcRn mAbs | | | |
|---|---|---|---|---|
| | Ka (1/Ms) | Kd (1/s) | KD (nM) | $\chi^2$ |
| V$_H$1/Vκ1 | 3.2E5 | 4.3E−4 | 1.39 | 0.11 |
| H3V$_H$1__E8Vκ2 | 3.2E5 | 6.0E−4 | 1.9 | 0.15 |
| G7V$_H$1__E8Vκ2 | 3.3E5 | 7.1E−4 | 2.1 | 0.15 |
| G9V$_H$1__E8Vκ2 | 6.1E5 | 5.1E−4 | 0.84 | 0.25 |
| H1V$_H$1__E8Vκ2 | 2.1E5 | 2.5E−4 | 1.2 | 0.02 |

Pairwise comparisons were made between antibodies having Vκ1 vs. Vκ2, holding constant an affinity matured heavy chain (i.e., G9V$_H$1, H3V$_H$1, or H1V$_H$1) and between H3V$_H$1 and G9V$_H$1, holding Vκ2 constant. Protein A (Sigma Cat. No. P6031) was coated onto Flow Cells (Fc) 1, 2, 3 and 4 of a series S CM5 sensor chip (GE Healthcare Cat. No. BR100530) surface using standard amine coupling chemistry Immobilization was carried out at a protein concentration of 20 μg/ml in 10 mM acetate buffer pH 5.0 to a target response level of 500 resonance units (RUs). 10 nM antibody was captured on F$_c$ 2, 3 and 4 at 10 μl/min to give an RU of ~172 (analyte binding level (R$_{max}$) of 50-150 RU) and the surface allowed to stabilize.

For kinetic analysis, a 2-fold dilution range was selected from 50-0.02 nM FcRn. The association phase of FcRn analyte was monitored for 450 seconds, and dissociation was measured for 1500 seconds, at 40 μl/min F$_c$1 was a reference channel and was subtracted from other flow cells to correct for non-specific binding. Kinetic values are based on a 1:1 binding model (Table 11).

TABLE 11

Binding kinetics of anti-human FcRn mAbs

| mAbs | $F_c$ | Ka (1/Ms) | Kd (1/s) | KD (nM) | $\chi^2$ |
|---|---|---|---|---|---|
| G9V$_H$1__Vκ1 | 3 | 3.80E5 | 1.34E-4 | 0.35 | 0.30 |
| G9V$_H$1__Vκ2 | 4 | 4.25E5 | 1.40E-4 | 0.39 | 0.19 |
| H3V$_H$1__Vκ1 | 3 | 4.66E5 | 1.11E-4 | 0.24 | 0.28 |
| H3V$_H$1__Vκ2 | 4 | 5.46E5 | 1.20E-4 | 0.22 | 0.30 |
| H1V$_H$1__Vκ1 | 3 | 2.96E5 | 8.76E-5 | 0.30 | 0.55 |
| H1V$_H$1__Vκ2 | 4 | 2.89E5 | 9.28E-5 | 0.32 | 0.54 |
| H3V$_H$1__Vκ2 | 3 | 4.78E5 | 1.11E-4 | 0.23 | 0.25 |
| G9V$_H$1__Vκ2 | 4 | 3.18E5 | 1.27E-4 | 0.40 | 0.20 |

In a further study, surface plasmon resonance (SPR) was conducted using a Biacore 3000 instrument (GE Healthcare) with CM5 sensor chips coupled with mAbs (~500-700 resonance units) using amine-coupling chemistry as described by the manufacturer. The coupling was performed by injecting 3 μg/ml of each protein into 10 mM sodium acetate, pH 4.5 (GE Healthcare), using the amine coupling kit (GE Healthcare). HBS-P buffer pH 7.4 (0.01 M HEPES, 0.15 M NaCl, 0.005% surfactant P20) or phosphate buffer pH 6.0 (67 mM phosphate buffer, 0.15 M NaCl, 0.005% Tween 20) were used as running buffer and dilution buffer. Binding kinetics were determined by injecting titrated amounts of monomeric His-tagged hFcRn (400.0-12.5 nM) over immobilized Abs at pH 7.4 or pH 6.0. All SPR experiments were conducted at 25° C. with a flow rate of 40 μl/min Binding data were zero-adjusted, and the reference cell value subtracted. The Langmuir 1:1 ligand binding model provided by the BIAevaluation software (version 4.1) was used to determine the binding kinetics. The closeness of the fit is described by the statistical value $\chi^2$.

Figure 7:
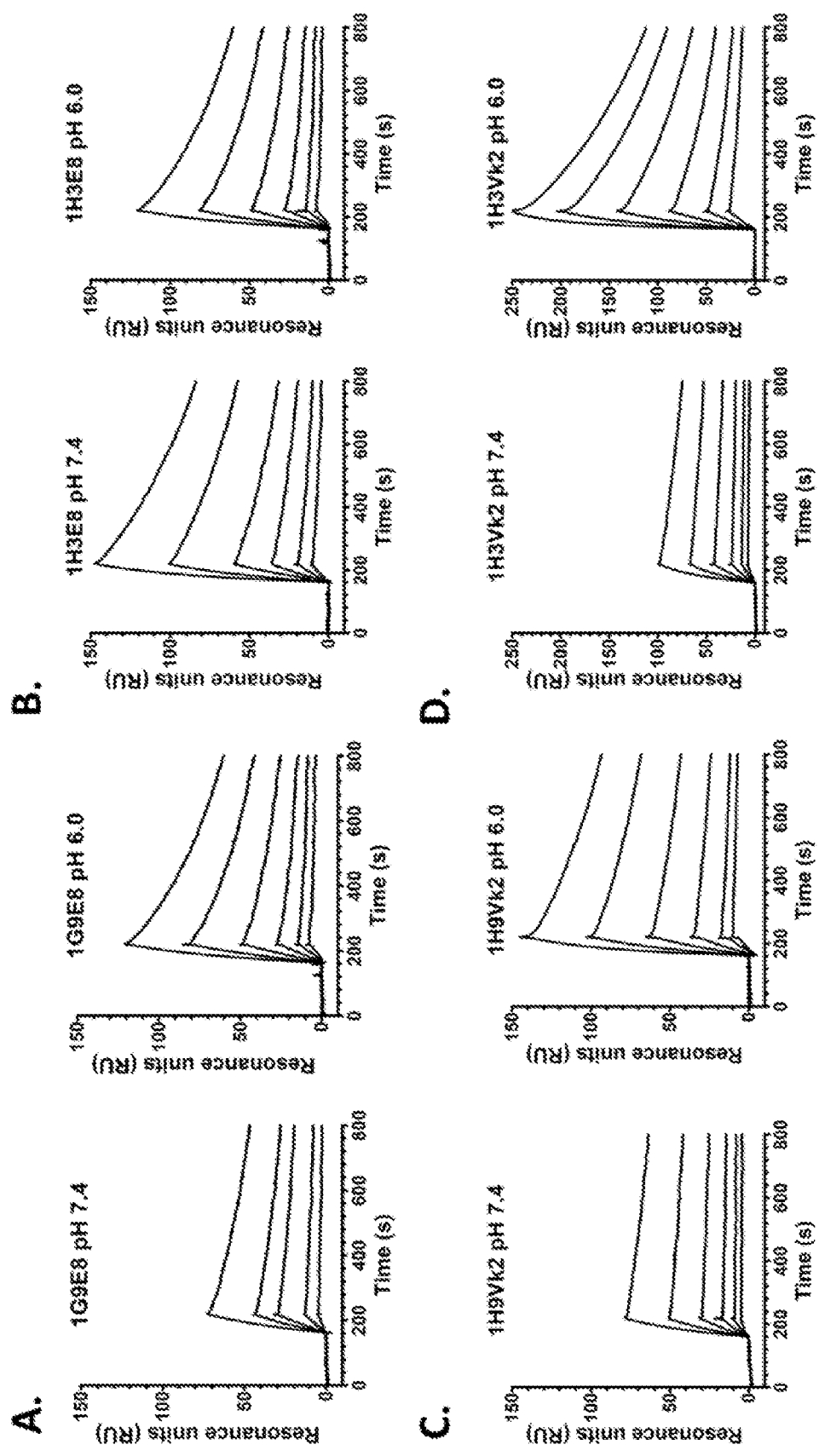
FIG. 7 shows binding of mAbs to human FcRn at pH 7.4 and 6.0. IgG antibodies comprising G9 or H3 affinity matured heavy chains paired with affinity matured E8 or humanized parental Vκ2 light chains were coupled to a BIACORE® CM5 sensor chip. Sensorgrams show binding of titrated amounts of monomeric human FcRn injected over the immobilized mAbs at pH 7.4 and pH 6.0. (A) G9E8, (B) H3E8, (C) G9Vκ2, (D) H3Vκ2.
Figure 8:
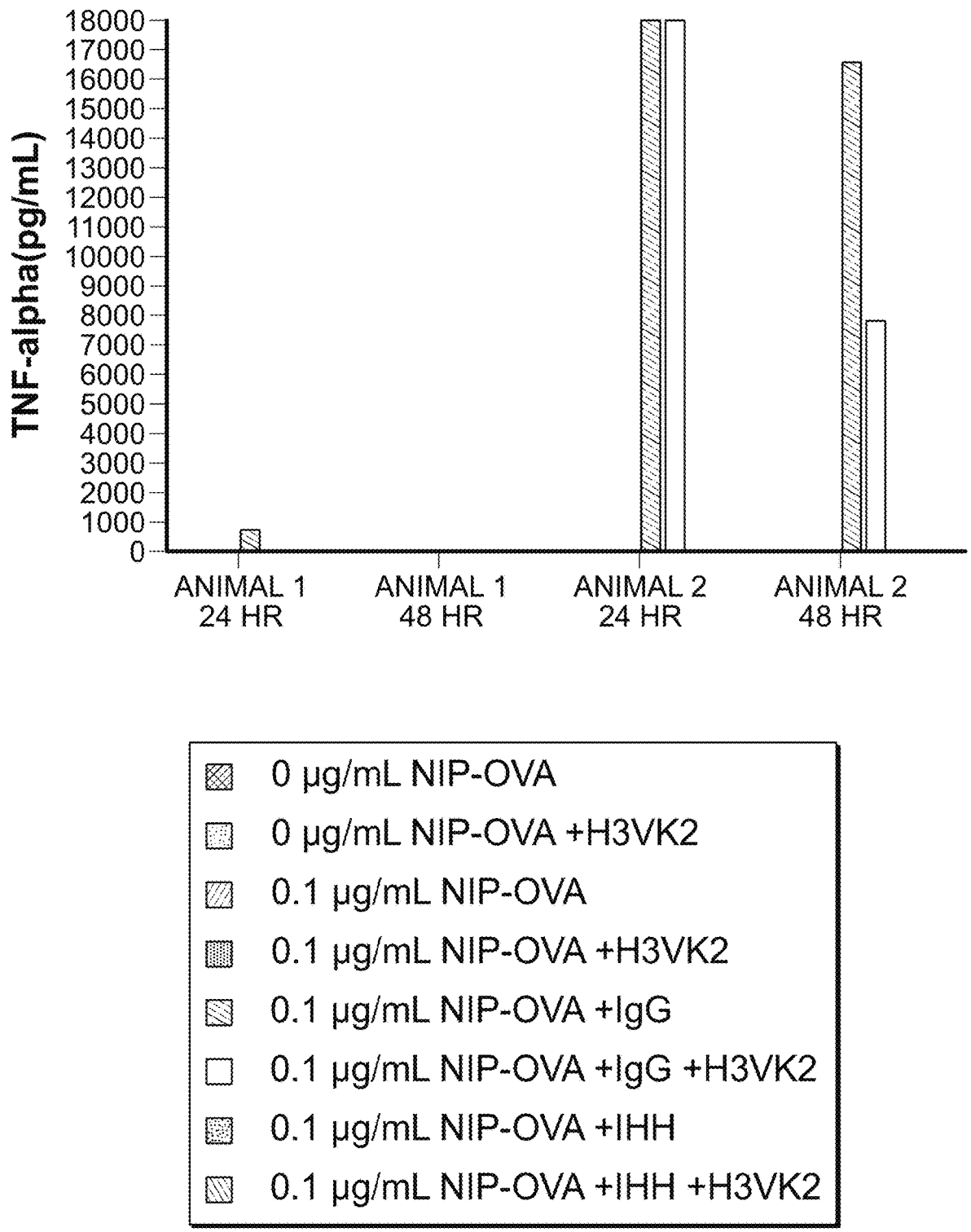
FIG. 8 shows the results of a whole blood assay in which the release of tumor necrosis factor-α (TNF-α) was measured. Black bars represent the assay run with 0.1 µg/ml NIP-OVA-IgG complexes but no H3Vκ2; Gray bars represent the assay run with 0.1 µg/ml NIP-OVA-IgG complexes in the presence of H3Vκ2. The four bar graphs represent, reading from left to right: animal 1 at 24 hours; animal 1 at 48 hours; animal 2 at 24 hours; animal 2 at 48 hours. Animal 1 was a non-responder, i.e., the amount of TNF-α produced was negligible upon stimulation with NIP-OVA-IgG complexes. The production of TNF-α by animal 2 at 24 hours was actually inhibited by H3Vκ2; this inhibition was masked because such a large amount of TNF-α was produced that both the black and gray bars were off the scale of this graph.
Figure 9:
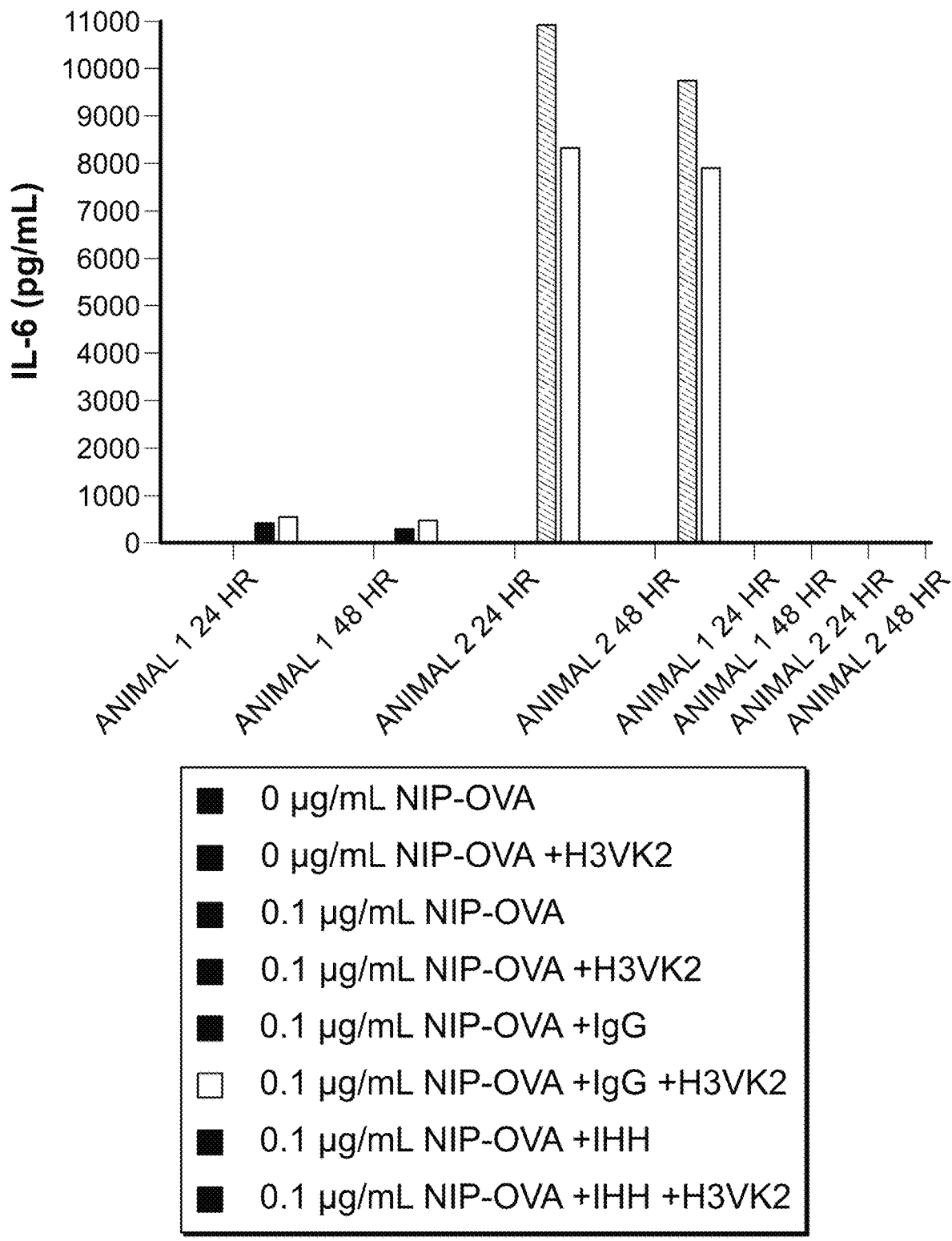
FIG. 9 shows the results of a whole blood assay in which the release of interleukin-6 (IL-6) was measured. Black bars represent the assay run with 0.1 µg/ml NIP-OVA-IgG complexes but no H3Vκ2; Gray bars represent the assay run with 0.1 µg/ml NIP-OVA-IgG complexes in the presence of H3Vκ2. The four bar graphs represent, reading from left to right: animal 1 at 24 hours; animal 1 at 48 hours; animal 2 at 24 hours; animal 2 at 48 hours.
Figure 10:
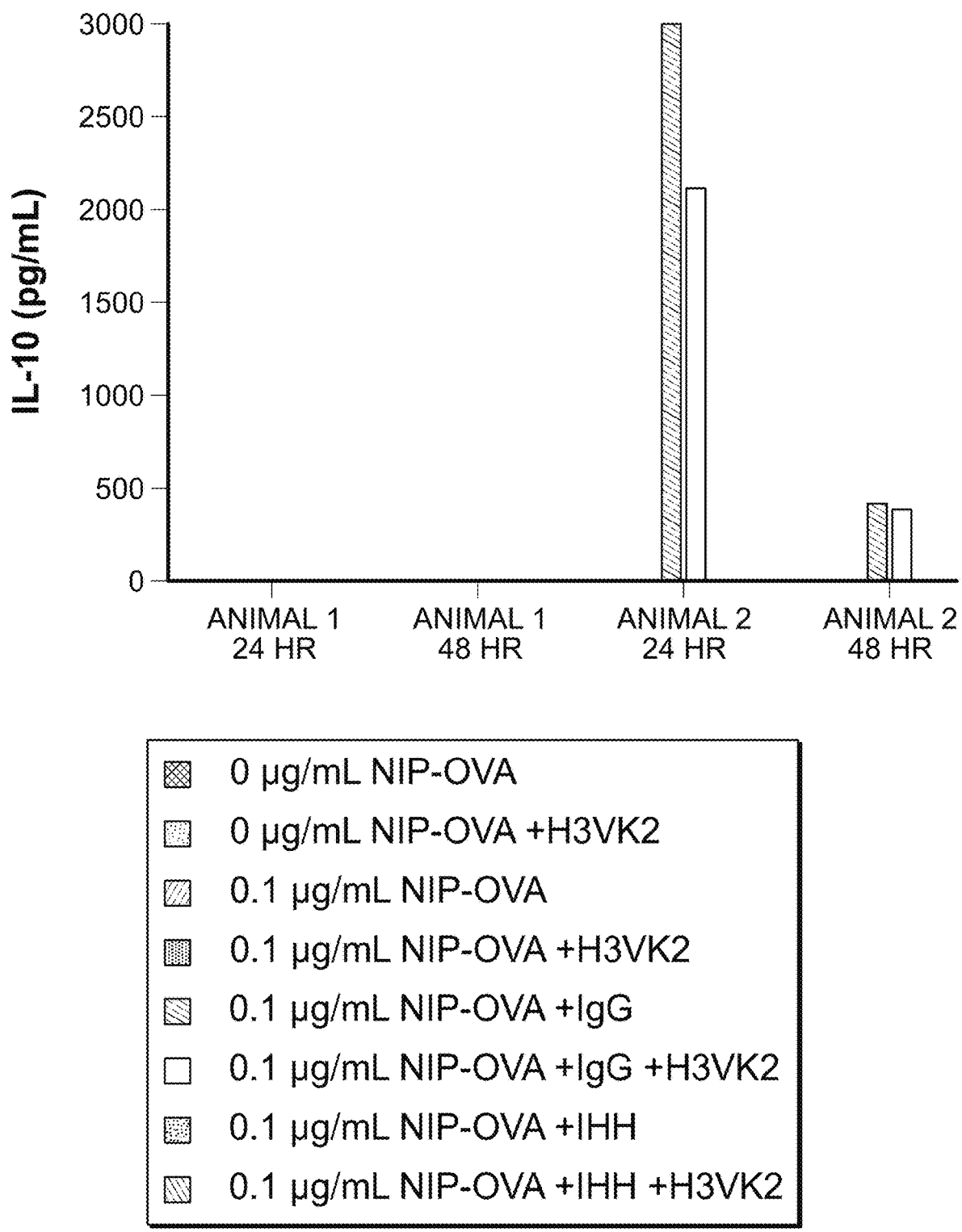
FIG. 10 shows the results of a whole blood assay in which the release of interleukin-10 (IL-10) was measured. Black bars represent the assay run with 0.1 µg/ml NIP-OVA-IgG complexes but no H3Vκ2; Gray bars represent the assay run with 0.1 µg/ml NIP-OVA-IgG complexes in the presence of H3Vκ2. The four bar graphs represent, reading from left to right: animal 1 at 24 hours; animal 1 at 48 hours; animal 2 at 24 hours; animal 2 at 48 hours.

FIG. 7 shows plots of binding association and dissociation for affinity matured heavy chain G9 or H3, paired with variant light chain Vκ2 or affinity matured light chain E8, determined by surface plasmon resonance. Kinetic rate constants are provide in 12, below. The kinetic rate constants were obtained using a simple first-order (1:1) Langmuir bimolecular interaction model. The kinetic values represent the average of duplicates. The $\chi^2$ (chi-square) values represent the fit to the binding model used.

TABLE 12

Binding kinetics of anti-human FcRn mAbs

| Anti-FcRn mAbs | pH 7.4 | | | | pH 6.0 | | | |
|---|---|---|---|---|---|---|---|---|
| | Ka ($10^4$/Ms) | Kd ($10^{-4}$/s) | KD (nM) | $\chi^2$ | Ka ($10^4$/Ms) | Kd ($10^{-4}$/s) | KD (nM) | $\chi^2$ |
| G9E8 | 4.1 ± 0.1 | 6.7 ± 0.4 | 16.3 | 1.3 | 6.9 ± 0.2 | 12.0 ± 0.1 | 17.4 | 2.3 |
| H3E8 | 6.8 ± 0.3 | 9.2 ± 0.1 | 13.5 | 1.0 | 13.4 ± 0.5 | 12.9 ± 0.2 | 9.6 | 6.0 |
| G9Vκ2 | 6.1 ± 0.1 | 3.0 ± 0.0 | 4.9 | 0.5 | 8.5 ± 0.1 | 6.3 ± 0.1 | 7.4 | 0.9 |
| H3Vκ2 | 8.1 ± 0.1 | 4.1 ± 0.1 | 5.1 | 1.0 | 13.0 ± 1.0 | 5.0 ± 0.2 | 3.8 | 5.0 |

In a further study, surface plasmon resonance (SPR) was conducted using a Biacore 3000 instrument (GE Healthcare) with CM5 sensor chips coupled with antibodies (~550 resonance units (RU)) using amine-coupling chemistry as described by the manufacturer. The coupling was performed by injecting 2.5 μg/ml of each protein into 10 mM sodium acetate, pH 4.5 (GE Healthcare), using the amine coupling kit (GE Healthcare). HBS-P buffer pH 7.4 (0.01 M HEPES, 0.15 M NaCl, 0.005% surfactant P20) or phosphate buffer pH 6.0 (67 mM phosphate buffer, 0.15 M NaCl, 0.005% Tween 20) were used as running buffer and dilution buffer. Binding kinetics were determined by injecting titrated amounts (400.0-12.5 nM) of monomeric His-tagged human FcRn (hFcRn) (JTA) over immobilized mAb H3Vk2 at pH 7.4 or pH 6.0. For human IgG1 (hIgG1) and human IgG4 (hIgG4), 10.000-325.0 nM were injected. All SPR experiments were conducted at 25° C. with a flow rate of 40 μl/min Binding data were zero-adjusted, and the reference cell value subtracted. The Langmuir 1:1 ligand binding model provided by the BIAevaluation software (version 4.1) was used to determine the binding kinetics. The closeness of the fit is described by the statistical value χ2.

Figure 12:
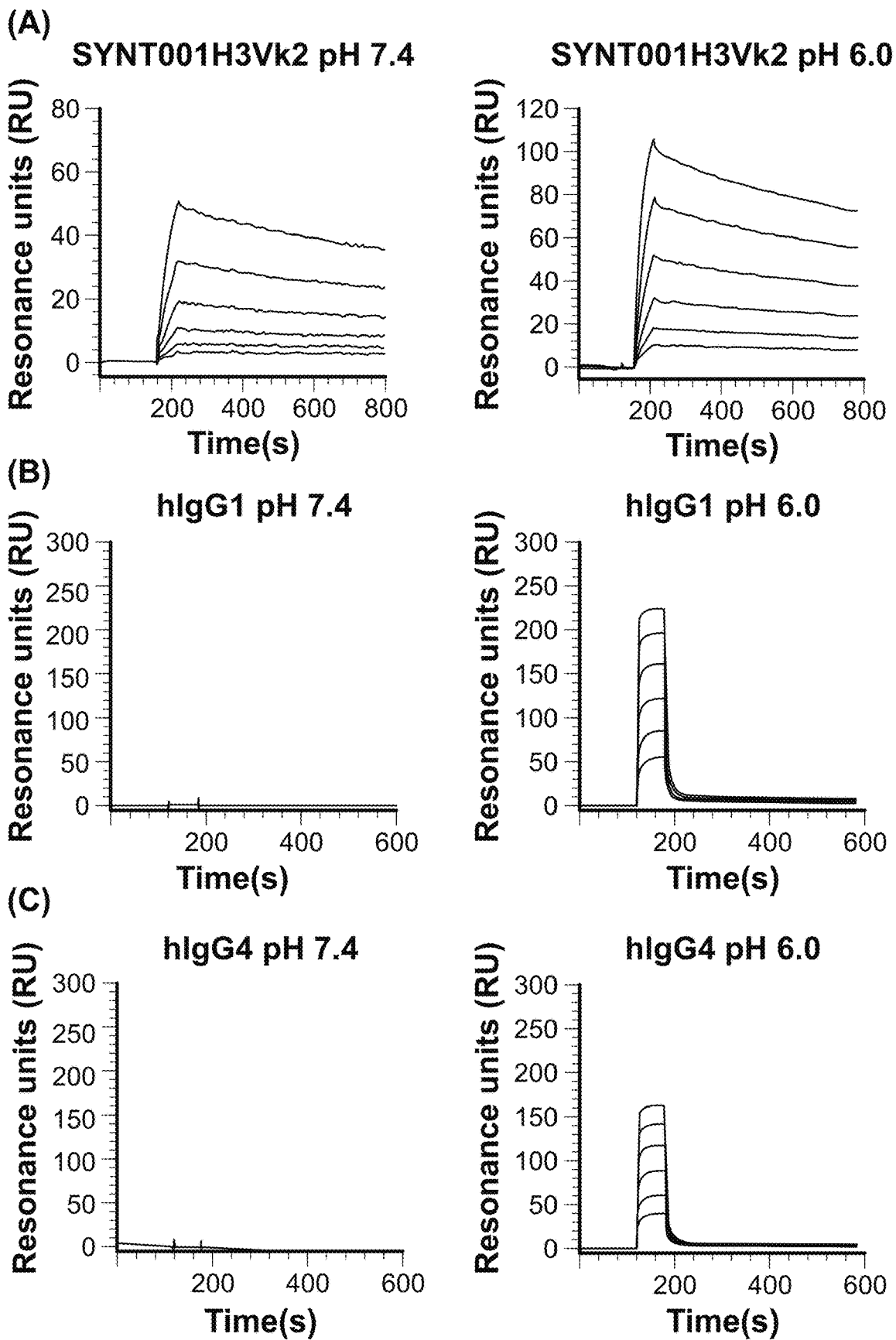
FIG. 12 shows the binding of human IgG subclasses IgG1 and IgG4 as well as anti-human FcRn mAb H3Vk2 to human FcRn at pH 7.4 and pH 6.0. Representative sensorgrams showing binding of titrated amounts of hFcRn injected over the immobilized (A) H3Vk2, (B) hIgG1, and (C) hIgG4 at pH 7.4 and pH 6.0.

FIG. 12 shows plots of binding association and dissociation for hIgG1, hIgG4, and H3Vk2. Table 13 below shows the results in tabular form.

TABLE 13

Binding kinetics of human IgG1, human IgG4, anti-FcRn mAb H3Vk2

| | pH 7.4 | | | | pH 6.0 | | | |
|---|---|---|---|---|---|---|---|---|
| | Ka ($10^4$/Ms) | Kd ($10^{-4}$/s) | KD (nM) | $\chi^2$ | Ka ($10^4$/MS) | Kd ($10^{-4}$/s) | KD (nM) | $\chi^2$ |
| hIgG1 | NA | NA | NA | | 10.8 ± 0.3 | 823.9 ± 5.4 | 762.8/1250 | 1.2/3.0 |
| MgG4 | NA | NA | NA | | 9.9 ± 0.4 | 1000.0 ± 0.2 | 1010.1/970 | 1.8/0.2 |
| H3Vκ2 | 7.9 ± 0.2 | 5.6 ± 0.2 | 7.0 | 0.3 | 12.0 ± 0.6 | 4.6 ± 0.1 | 3.8 | 5.0 |

The kinetic rate constants were obtained using a simple first-order (1:1) Langmuir bimolecular interaction model. The kinetic values represent the average of duplicates.
The $\chi^2$ (chi-square) values represent the fit to the binding model used.
The kinetic rates are rough estimates as the data do not fit well with the Langmuir binding model.
NA: not acquired due to weak binding.
The KD values for hIgG1 and hIgG4 were estimated using a steady-state affinity model.

As expected, hIgG1 and hIgG4 were shown to bind in a strictly pH dependent manner with KDs of roughly 1 μM at pH 6.0, and only very weak biding responses were obtained at neutral pH (at the highest concentration injected, 10.000 nM).

In a further study, the binding of H3Vk2 to cynomolgus monkey FcRn and to human FcRn obtained from two different suppliers was tested.

Surface plasmon resonance (SPR) was conducted using a Biacore 3000 instrument (GE Healthcare) with CM5 sensor chips coupled with mAb H3Vk2 (~550 resonance units (RU)) using amine-coupling chemistry as described by the manufacturer. The coupling was performed by injecting 2.5 μg/ml of H3Vk2 into 10 mM sodium acetate, pH 4.5 (GE Healthcare), using the amine coupling kit (GE Healthcare). HBS-P buffer pH 7.4 (0.01 M HEPES, 0.15 M NaCl, 0.005% surfactant P20) or phosphate buffer pH 6.0 (67 mM phosphate buffer, 0.15 M NaCl, 0.005% Tween 20) were used as running buffer and dilution buffer. Binding kinetics were determined by injecting titrated amounts (400.0-12.5 nM) of receptors over immobilized Ab at pH 7.4 or pH 6.0 (monomeric His-tagged human FcRn (hFcRn) (JTA) or human and cynomolgus FcRn (cFcRn) obtained from SINO Biological Inc). All SPR experiments were conducted at 25° C. with a flow rate of 40 μl/min Binding data were zero-adjusted, and the reference cell value subtracted. The Langmuir 1:1 ligand binding model provided by the BIAevaluation software (version 4.1) was used to determine the binding kinetics. The closeness of the fit is described by the statistical value χ2.

Figure 13:
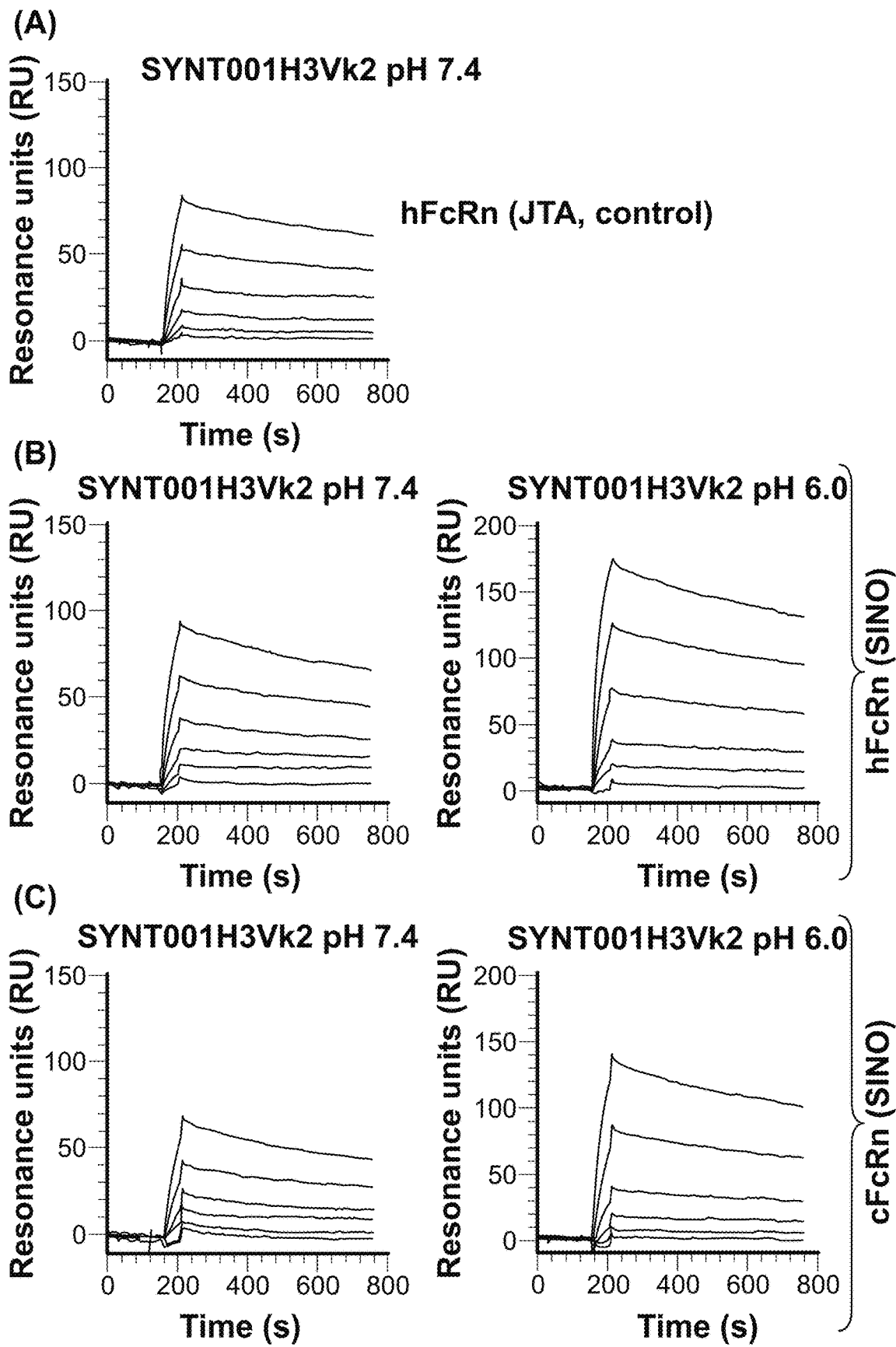
FIG. 13 shows binding of H3Vk2 to human and cynomolgus FcRn at pH 7.4 and pH 6.0. Representative sensorgrams showing binding of titrated amounts of (A) hFcRn injected over the immobilized Ab at pH 7.4, (B) hFcRn at pH 7.4 and pH 6.0, and (C) cFcRn at pH 7.4 and pH 6.0.
Figure 14:
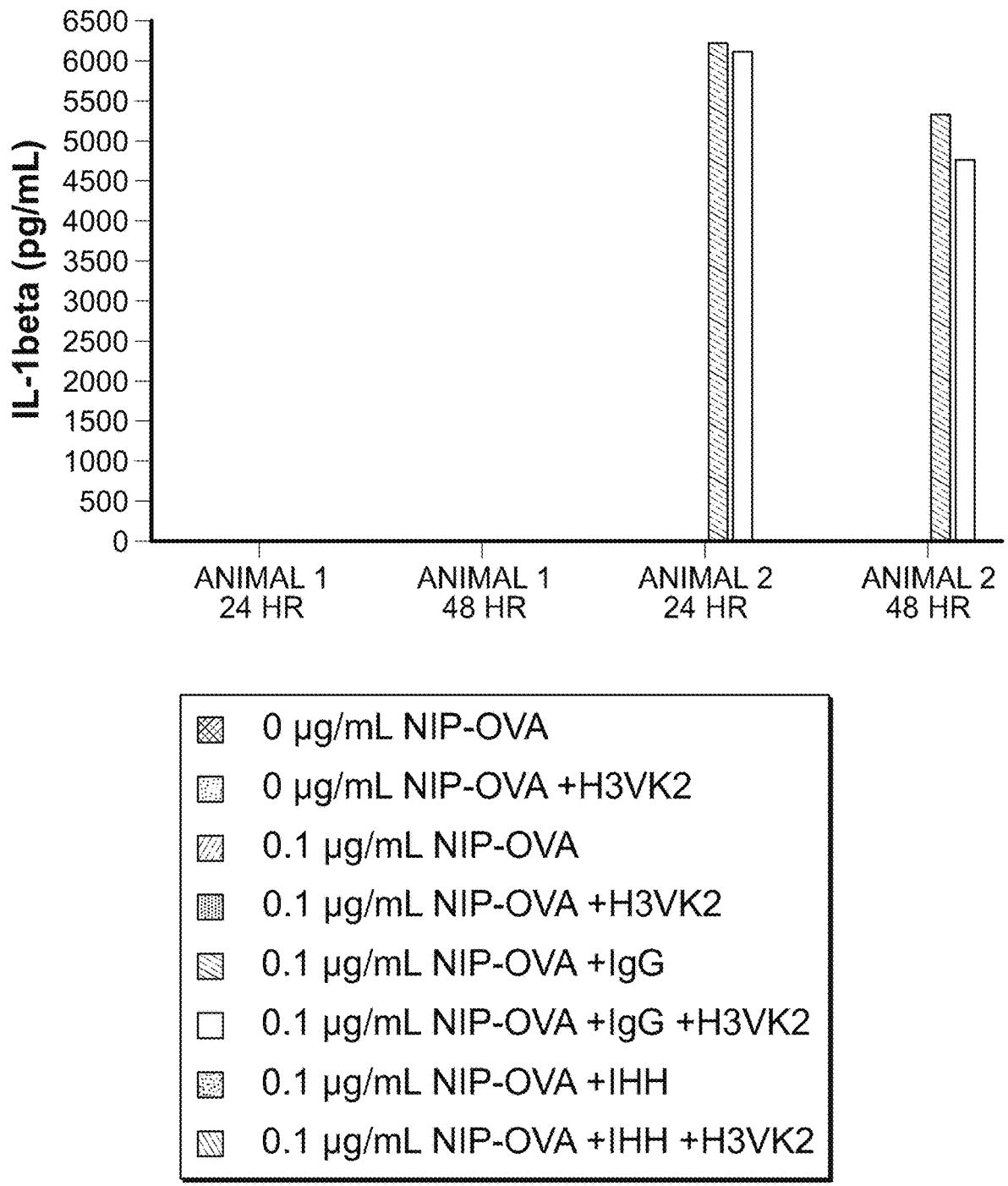
FIG. 14 shows the results of a whole blood assay in which the release of interleukin-1β (IL-1β) was measured. Black bars represent the assay run with 0.1 µg/ml NIP-OVA-IgG complexes but no H3Vκ2; Gray bars represent the assay run with 0.1 µg/ml NIP-OVA-IgG complexes in the presence of H3Vκ2. The four bar graphs represent, reading from left to right: animal 1 at 24 hours; animal 1 at 48 hours; animal 2 at 24 hours; animal 2 at 48 hours.

FIG. 13 shows plots of binding association and dissociation. Table 14 below shows the results in tabular form.

TABLE 14

Binding kinetics of H3Vk2

| Anti-FcRn mAbs | Ka ($10^4$/Ms) | Kd ($10^{-4}$/s) | KD (nM) | $\chi^2$ |
|---|---|---|---|---|
| pH 7.4 | | | | |
| hFcRn (JTA) H3Vk2 | 6.9 ± 0.2 | 3.2 ± 0.3 | 4.6 | 1.3 |
| hFcRn (SINO) H3Vk2 | 7.2 ± 0.2 | 4.3 ± 0.2 | 5.9 | 2.9 |
| pFcRn (SINO) H3Vk2 | 4.7 ± 0.1 | 5.6 ± 0.0 | 11.9 | 3.0 |
| pH 6.0 | | | | |
| hFcRn (SINO) H3Vk2 | 7.4 ± 0.1 | 4.3 ± 0.2 | 5.8 | 12.0 |
| pFcRn (SINO) H3Vk2 | 2.2 ± 0.2 | 5.1 ± 0.4 | 2.3 | 9.8 |

[a] The kinetic rate constants were obtained using a simple first-order (1:1) Langmuir bimolecular interaction model. The kinetic values represent the average of duplicates.
[b] The $\chi^2$ (chi-square) values represent the fit to the binding model used.
*The kinetic rates are rough estimates as the data do not fit well with the Langmuir binding model.

In this experimental set-up, the binding kinetics of H3 Vk2 toward human and cynomolgus FcRn obtained from SINO Biological Inc. was determined. As a comparison, monomeric human FcRn produced in-house and used in certain previous studies (JTA) was included at pH7.4. The commercial human form from SINO Biological Inc. gave very similar kinetic constants as that of the in-house produced human version. Cynomolgus FcRn was shown to bind the Ab at both pH conditions but with somewhat (roughly 2-fold) weaker affinity at pH 7.4 than the human receptor.

Example 6

Antigen Presentation Assay

Preparation of Bone Marrow Dendritic Cells (BMDCs)—Bone marrow (BM) cells are harvested from eight female B6.Cg-Fcgrt$^{tm1Dcr}$ Tg(FCGRT)32Dcr/DcrJ mice (Jackson Laboratory Stock No. 014565). These mice harbor a knock-out allele of the FcRn α-chain (Fcgrt$^{tm1Dcr}$) and express a human FcRn α-chain (FCGRT) transgene under control of the human FcRn promoter. BM cells are plated at 2×10$^6$/10 cm$^2$ into about 70 non-TC treated petri dishes in complete RPMI (C-RPMI). The BM cells are supplemented with GM-CSF (20 ng/ml) on day 3 and 6, and harvested (or frozen) for use on days 8-12 of BMDC culture.

In the antigen presentation assay, FcRn-mediated presentation of antigen by BMDCs is assessed by T cell activation. Specifically, BMDCs are incubated with an immune complex of antigen+antigen-specific antibody (NIP-OVA+anti-NIP-IgG) followed by determination of activation of antigen-specific T cells. The ability of anti-FcRn antibodies (compared to a non-specific control antibody of matching isotype) to inhibit antigen presentation (by blocking binding of FcRn to IC, thereby blocking NIP-OVA processing and presentation to T cells) is assessed by determining T cell activation. T cell activation is assessed using ELISAs to quantifying IL2 and IFN-γ production. Controls for non-specific antigen presentation (i.e., background levels of antigen presentation not mediated by FcRn) are provided by incubating BMDCs with test antibody and uncomplexed antigen (i.e., NIP-OVA without anti-NIP-IgG).

BMDCs are first incubated with test antibody or isotype control. Specifically, BMDCs are seeded into 96 well plates at $5\times10^4$/100 µl/well and incubated at 37° C. for 30-60 minutes. To each well is added 100 µl of each test antibody (or isotype control) to achieve an antibody concentration of 50, 25, 12.5, 6.25, or 3.125 nM. The BMDC-antibody mixtures are incubated for 30-60 minutes prior to immune complex (IC) addition. Sufficient wells are prepared to test each series of antibody dilutions for inhibition of activation of CD4$^+$ and CD8$^+$ T cells, and measurements in triplicate.

Immune Complex (IC) Formation 2.5 ml each of anti-NIP-IgG (2× concentration=200 µg/ml) and NIP-ovalbumin ("NIP-OVA")(2× concentration=200 µg/ml) are mixed and incubated at 37° C. for 60 minutes to form 200 µg/ml immune complexes (IC). An untreated (i.e., uncomplexed) 5 ml sample of 100 µg/ml NIP-OVA is prepared.

A mixture of each test antibody (or isotype control) and IC is prepared for addition to the BMDCs. Each test antibody is also mixed with NIP-OVA to provide background controls. Specifically, serial dilutions of the test antibodies (100, 50, 25, 12.5, 6.25 nM) are prepared, and 250 µl of each dilution is added to 250 µl of IC, as well as to 250 µl of 100 µg/ml NIP-OVA), producing test antibody+IC or test antibody+NIP-OVA solutions containing 50, 25, 12.5, 6.25, and 3.125 nM concentrations of the test antibodies.

The 96-well plates containing test antibody-treated-BDMCs are centrifuged, all but 25 µl/well of media is drawn off, and 100 µl of the test antibody+IC or test antibody+NIP-OVA solutions are added to the wells followed by incubation at 37° C. for 2-3 hrs.

T Cell Preparations

To obtain CD8$^+$ T cells, single cell suspensions are harvested from spleen and lymph nodes of female OTI, C57BL/6-Tg(TcraTcrb)1100Mjb/J mice (Jackson Laboratory Stock No. 003831). These transgenic mice express a transgenic T cell receptor designed to recognize ovalbumin residues 257-264 in the context of H2K$^b$ and are used to study the role of peptides in positive selection and the response of CD8$^+$ T cells to antigen. A Miltenyi kit is used to deplete non-CD8$^+$ T cells.

To obtain CD4$^+$ T cells, single cell suspensions are harvested from spleen and lymph nodes of female OTII, B6.Cg-Tg(TcraTcrb)425Cbn/J mice (Jackson Laboratory Stock No. 004194). These transgenic mice express the mouse alpha-chain and beta-chain T cell receptor that pairs with the CD4 coreceptor and is specific for chicken ovalbumin 323-339 in the context of I-Ab. A Miltenyi kit is used to deplete non-CD4$^+$ T cells.

The 96-well plates containing BDMCs, test antibodies, and IC (or uncomplexed NIP-OVA) are centrifuged, all but 25 µl/well is removed, and the wells are washed twice with prewarmed C-RPMI.

T cells (either CD4$^+$ or CD8$^+$) in amounts of $1.5\times10^5$/200 µl/well, are incubated for 24 hours at 37° C. 150 µl is harvested from each well for quantification of IL2 by ELISA. 150 µl/well of C-RPMI is added back to each well, followed by incubation for an additional 48 hours (72 hours total) at 37° C. At that point, 150 µl is harvested from each well for quantification of IFN-gamma by ELISA.

OTI (CD8$^+$) and OTII (CD4$^+$) T cell responses to each culture condition are assessed by measuring IL2 and IFN-gamma secretion into the culture supernatant by ELISA. IL2 is measured from both cultures at 24 hours diluted 1 to 3 for OTI, and diluted 1 to 20 for OTII. IFN-γ is measured from OTI cultures at 24 hours diluted 1 to 3, and OTII cultures at 72 hours diluted 1 to 20.

Example 7

Immunogenicity Testing

Antibodies are subjected to a pre-clinical ex vivo T cell assay (EPISCREEN®, Antitope Ltd.). Using a cohort selected to represent the number and frequency of HLA-DR allotypes expressed in the world population, the EPISCREEN® (Antitope Ltd.) assay effectively predicts T cell immunogenicity by quantifying T cell responses to protein therapeutics.

Example 8

Whole Blood Assay

An assay using whole blood from cynomolgus monkeys was developed in order to test the ability of anti-FcRn antibodies to block the production of cytokines in a physiologically relevant environment. To the whole blood was added either 0.1 µg/ml NIP-OVA or 0.1 µg/ml NIP-OVA to which an anti-NIP human IgG was bound. The NIP-OVA-IgG functioned as a surrogate immune complex in the assay, binding to FcRn and initiating effector functions of FcRn such as cytokine production. Addition of NIP-OVA-IgG resulted in copious production of the cytokines tumor necrosis factor-α (TNF-α), interleukin-6 (IL-6), interleukin-10 (IL-10), and interleukin-1β (IL-1β) (see the black bars in FIGS. 8, 9, 10, and 14, respectively). In contrast, addition of NIP-OVA alone did not result in cytokine release. When the IgG in NIP-OVA-IgG was replaced with IHH, an anti-NIP human IgG1 with three point mutations (I253A/H310A/H435A) in the Fc domain that abolish binding to FcRn (Qiao et al., 2008, Proc. Natl. Acad. Sci. USA 105: 9337-9342), no cytokine release was observed, demonstrating that the effect measured in the assay was FcRn-dependent.

Addition of NIP-OVA-IgG in the presence of the anti-FcRn antibody H3Vκ2 resulted in marked diminution of the amount of cytokines produced (see the gray bars in FIGS. 8, 9, 10, and 14 respectively). This demonstrates the effectiveness of the anti-FcRn antibodies described herein to block one of the effects of the interaction between FcRn and IC. It is notable that not all of the monkeys produced significant amounts of cytokines in this assay. Thus, not all of the monkeys exhibited measurable inhibition of cytokine production by H3Vκ2. Those monkeys that did not produce significant amounts of cytokines would not be good candidates for receiving therapy with an anti-FcRn antibody. Conversely, those monkeys which exhibited production of significant amounts of cytokines and showed good inhibition of cytokine production in the presence of H3Vκ2 would be good candidates for receiving therapy with an anti-FcRn antibody.

Figure 11:
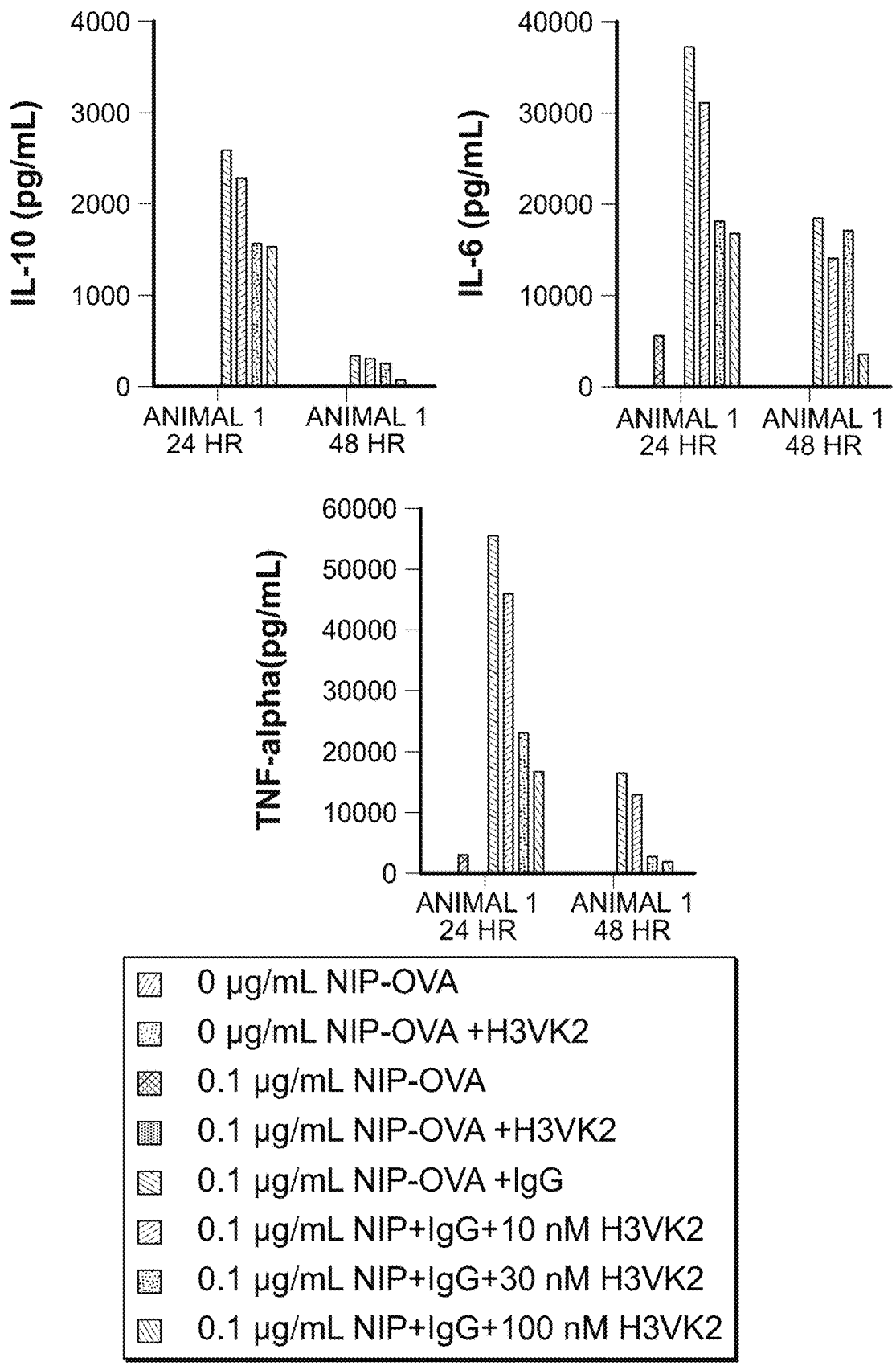
FIG. 11 shows the results of another whole blood assay. The rightmost bars (shown in green, blue, and red) demonstrate that H3Vκ2 has a dose-dependent inhibitory effect on the amount of cytokines produced.

FIG. 11 shows the results of another run of the whole blood-based assay in which increasing amounts of H3Vκ2 were added. As the rightmost three bars of the graphs indicate, a dose-dependent inhibitory effect of H3Vκ2 on the amount of cytokines produced was observed.

Figure 17:
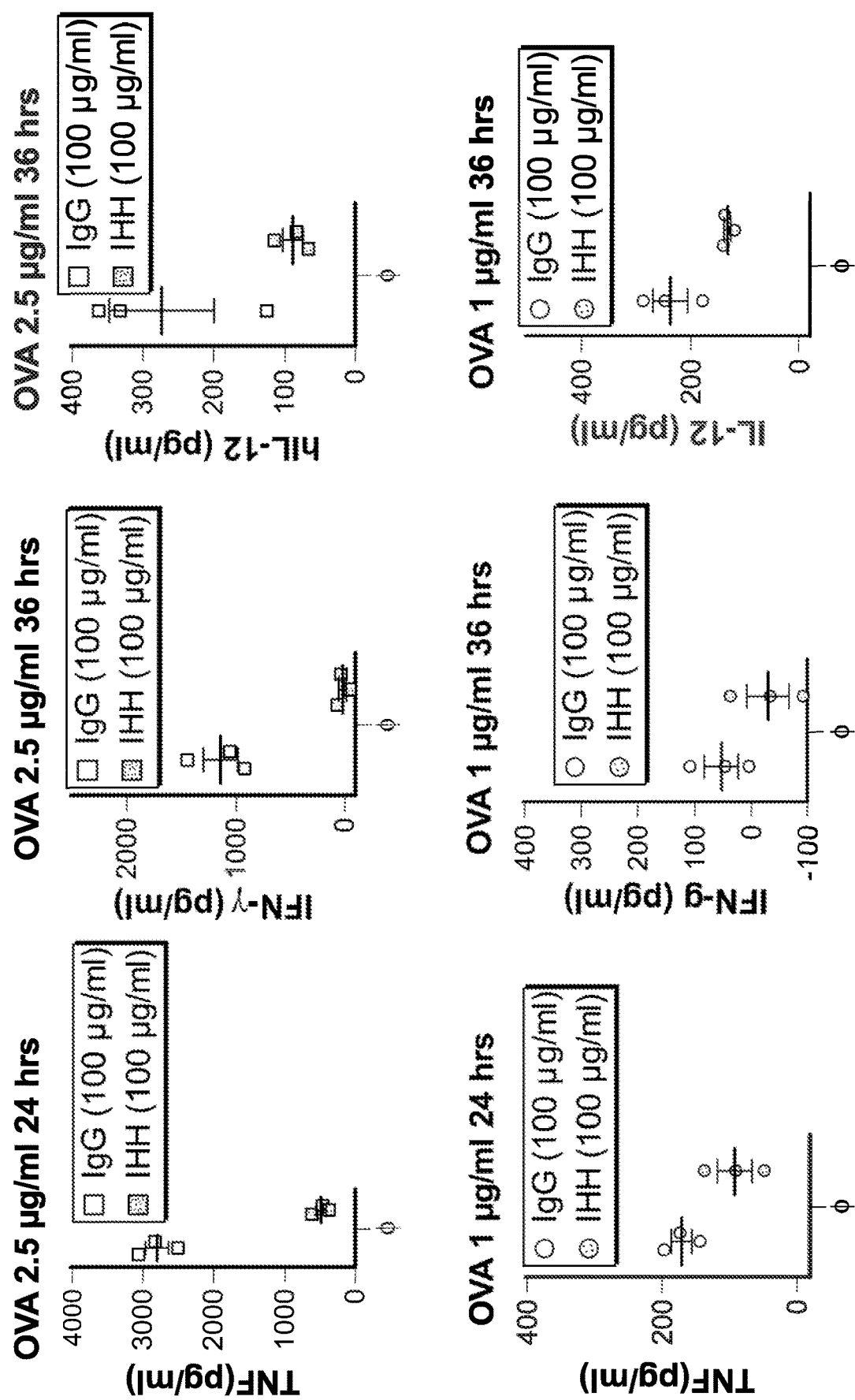
FIG. 17 shows the results of a whole blood assay using human blood in which the release of tumor necrosis factor-α (TNF-α), interferon-γ (IFN-γ), and interleukin-12 (IL-12) was measured in the presence of NIP-OVA-IgG complexes or NIP-OVA-IHH complexes.

The whole blood assay described above was adapted for use with whole blood from humans. To whole heparized blood from human subjects was added pre-formed immune complexes of NIP-OVA at various concentrations from 1.0 µg/ml to 100 µg/ml with a stable concentration of either anti-NIP human IgG or anti-NIP-IHH mutated to not bind FcRn. The whole blood samples were incupated at 37° C.

and the cytokine levels were measured by either ELISA or bead array after 24 or 36 hours. As shown in FIG. 17, the NIP-OVA-IgG immune complexes stimulated release of multiple different cytokines, while the lack of response from NIP-OVA-IHH immune complexes demonstrate that the effect measured in the assay was FcRn-dependent.

Figure 18:
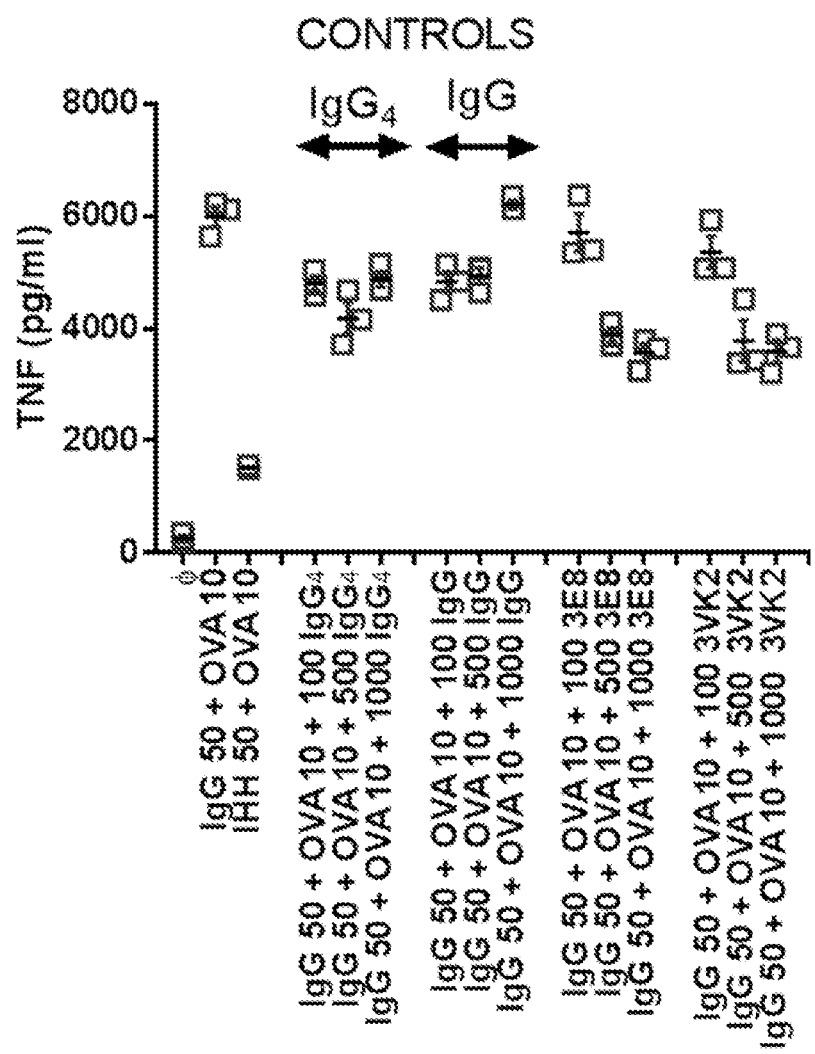
FIG. 18 shows the results of another whole blood assay using human blood in which the effect of H3E8 and H3Vk2 was tested against irrelevant IgG4 and IgG1 controls.
Figure 19:
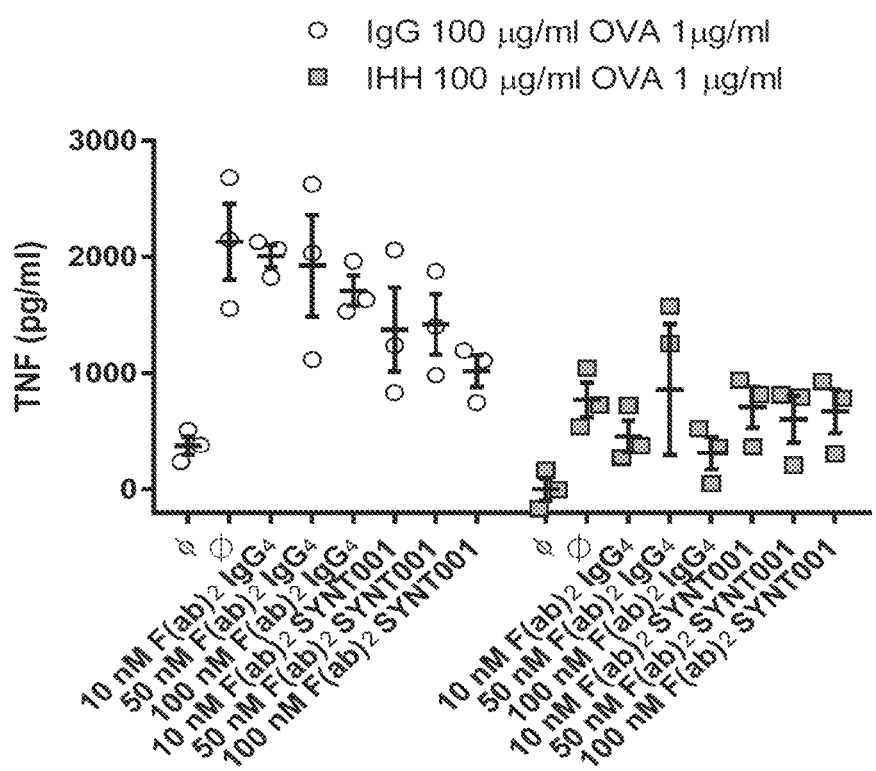
FIG. 19 shows the results of another whole blood assay using human blood using test and control antibodies in F(ab')$_2$ format.

FIG. 18 shows that addition of NIP-OVA-IgG in the presence of the anti-FcRn antibodies H3E8 and H3Vκ2 in IgG4 format resulted in diminution of the amount of cytokines produced. The assay was re-performed with the H3Vκ2 and control antibodies in F(ab')$_2$ format. The results are shown in FIG. 19, which demonstrates the effectiveness of the anti-FcRn antibodies described herein to block one of the effects of the interaction between FcRn and IC in whole human blood.

Example 9

IgG Clearance Study

An in vivo study using transgeneic mice was conducted to examine the effects of anti-FcRn antibodies on human IgG clearance. Twenty (20) 14.9 weeks±3 days old hFcRn TG mice hemizygous for the human FCGRT transgene were divided into groups 1 and 2 each containing five females and five males. On Day 0, all mice were pre-dosed by IV injection with human IVIG at 245 mg/kg admixed with 5 mg/kg of the hen egg lysozyme-specific humanized IgG1 mAb, HuLys11, for a total 250 mg/kg IgG. Blood samples were collected from each mouse at 48, 56, 72, 80, 96, 120, and 144 hours post IV injection with human IgG//HuLys11. One hour following the blood draw at 48 hours, 20 mg/kg of H3Vκ2 or PBS was administered IV. Plasma concentrations of HuLys 11 were quantified by ELISA. Treatment with 20 mg/kg H3Vκ2 yielded a highly significant 3× reduction (p=0.0001) in the plasma concentrations of HuLys11 compared with the PBS control group. This result demonstrates that hFcRn blockade by H3Vκ2 promotes the clearance of hIgG from the circulation.

Figure 15:
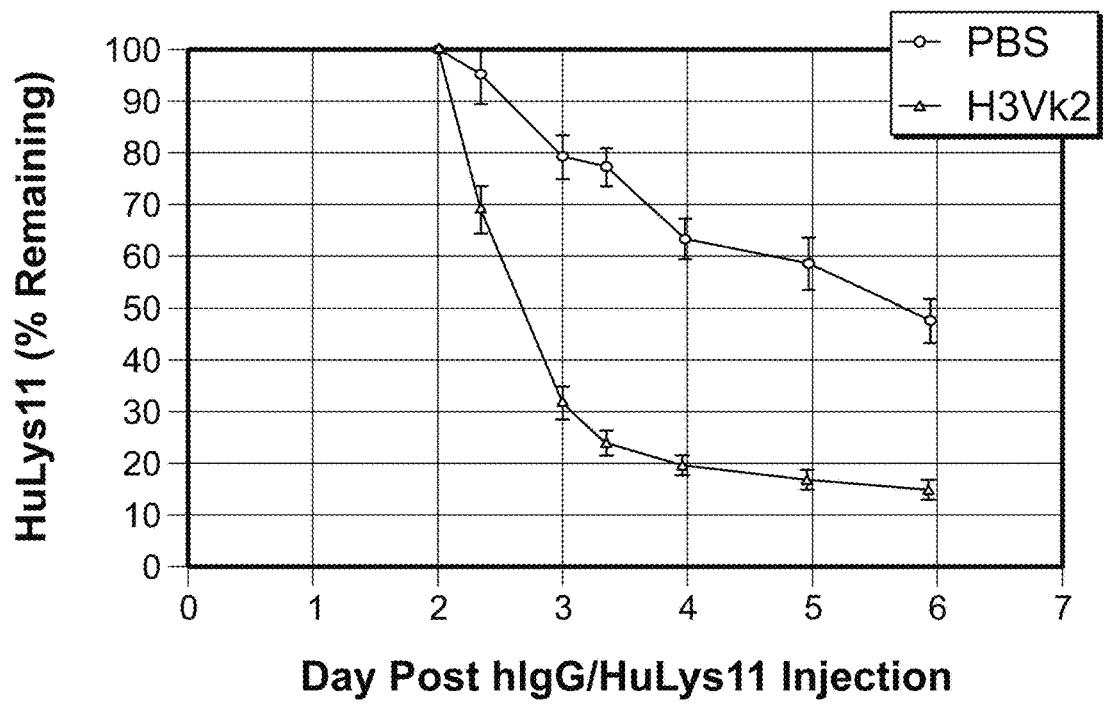
FIG. 15 shows the effects of H3Vk2 on hIgG catabolism in hFcRn transgeneic mice. Data are plotted as percent (±standard error) HuLys11 (human IgG1) remaining based on the amount of HuLys11 in the plasma of mice at 48 hours prior to injection of 20 mg/kg H3Vk2 at 2 hours after the 48 hour blood draw. The first data point collected after H3 Vk2 treatment was at 6 hours post dosing during Day 3.

FIG. 15 shows the results of the study plotted as percent (±standard error) HuLys11 (human IgG1) remaining based on the amount of HuLys11 in the plasma of mice at 48 hours prior to injection of 20 mg/kg SYNT001 at 2 hours after the 48 hour blood draw.

Example 10

Immune Complex Clearance Study

An in vivo study using transgeneic mice was conducted to examine the effects of anti-FcRn antibodies on multimeric immune complexes formed in vitro and infused intravenously into hFcRn TG mice according to Qiao SW, PNAS 2008. Sixteen (16) 8.1 weeks+/−3 days old hFcRn Tg mice hemizygous for the human FCGRT transgene were randomized into 2 groups of 8 mice (4 males/4 females). Multimeric ICs were formed by incubating 750 µg/mL of $^{NIP}$hIgG anti-NIP with 75 µg/mL NIP conjugated-ovalbumin (with 11 NIP molecules per OVA) for 20 minutes at room temperature in PBS. On Day 0, eight mice from each group were pre-dosed by IV injection with $^{NIP}$hIgG/NIP-OVA IC at 7.5 mg/kg and 0.75 mg/kg, respectively. This is equivalent to 150 µg $^{NIP}$hIgG+15 µg NIP-OVA for a 20 g body weight dose. Blood samples were collected at 24, 32, 48, 56, 72, 96, and 120 hours post IV injection with immune complexes. One hour following the blood draw at 24 hours, 20 mg/kg of H3Vκ2 or PBS was administered IV. Plasma concentrations of $^{NIP}$hIgG were quantified by ELISA. The results of this in vivo experiment confirm that H3Vκ2 inhibits the protection afforded by FcRn on the catabolism of immune complexes formed between IgG and antigen similarly to that seen in Example 9 for monomeric IgG.

Figure 16:
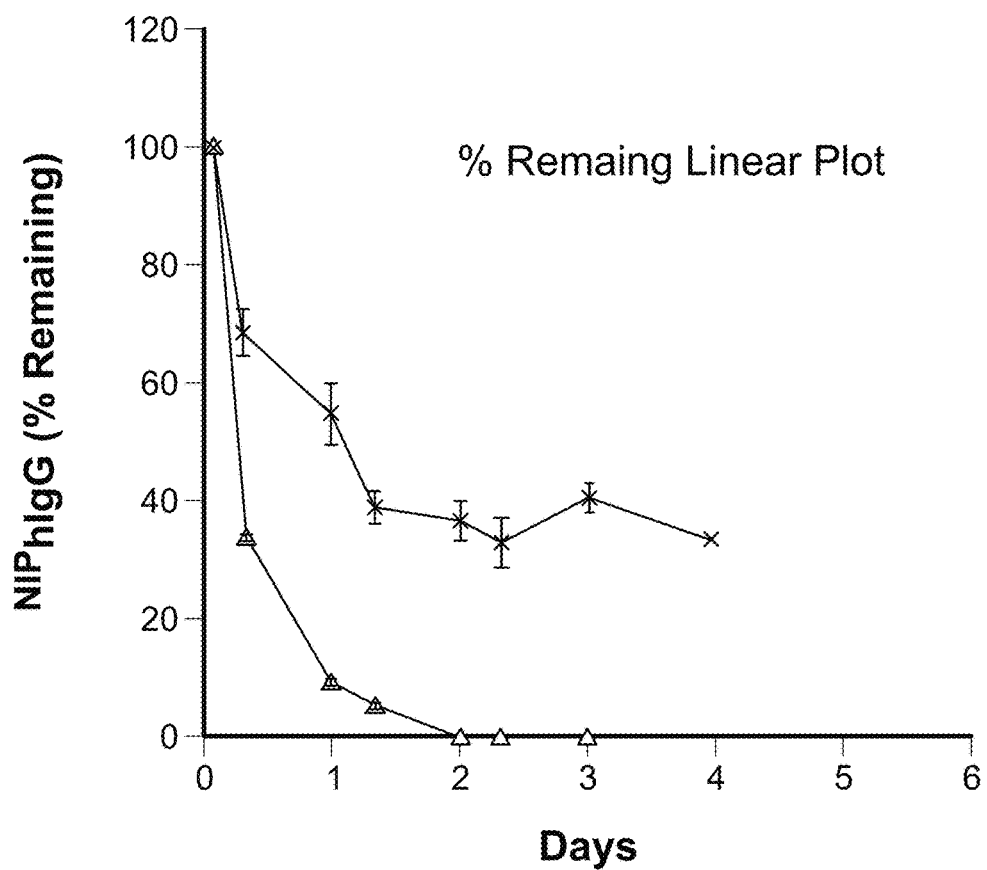
FIG. 16 shows the effects of H3Vk2 on multimeric immune complex (IC) catabolism in hFcRn transgeneic mice. The study was designed according to Qiao SW, PNAS 2008. Results are plotted as percent (±standard error) IC remaining based on the 24 hour baselines at the indicated time points.

FIG. 16 shows the results of the study plotted as as the mean % IC remaining based on the 24 hr baselines (±standard error) at the indicated time points.

Example 11

Monocyte FcRn Expression

The monocyte FcRn expression of cynomolgus monkeys whole blood samples to characterize the pharmacokinetic properties and response of additional pharmacodynamic markers following injection of anti-FcRn antibodies. Cynomolgus monkeys were dosed once weekly via intravenous injection with either vehicle (Group 1), H3Vκ2 at 10 mg/kg/dose (Group 2), H3Vκ2 at 40 mg/kg/dose (Group 3), or H3E8 at 40 mg/kg/dose (Group 4) for four weeks, followed by a four week recovery period. Whole blood samples were collected by venipuncture into tubes containing K$_2$EDTA anti-coagulant and kept at room temperature until analyzed. Two samples were taken prior to the initial injection of anti-FcRn antibodies, at two hours following the first injection, then immediately prior to and two hours following each subsequent injection. An aliquot of blood was used to measure the white blood cell count (total, absolute and percent differential) by ADVIA. White blood cell counts and the total lymphocyte counts (TLC) were reported as lymphocytes per µL of whole blood (cells/µL). The monocytes cell counts were reported as a relative percentage (%) as well as lymphocytes per µL of whole blood (cells/µL).

Extra-cellular and intra-cellular monocyte FcRn expression levels were analyzed using were analyzed by flow cytometry using a FACSCanto™ II flow cytometer with the FACSDiva™ software. For the extra-cellular and intra-cellular FcRn receptor expression on monocytes, the geometric mean fluorescence intensity (GeoMFI) of FcRn expression in CD45+CD14+FcRn+ cells and the percentage value of the CD14+ monocytes expressing FcRn from the CD14+ monocyte population were reported. In addition, monocytes (CD45+/CD14+) absolute counts and relative percentages were reported.

In the majority of dosed animals, when compared to the pre-study time points, a trend towards a decrease was obtained for the geomean fluorescence intensity (GeoMFI) for the extra-cellular FcRn expression on the CD45+/CD14+ FcRn+ cells 2 hours postdose at each time point, as shown in Table 15. These changes were considered to be a result of increased binding of the anti-FcRn antibodies to the FcRn receptor. Generally, the geoMFI values returned to the pre-study levels prior to each scheduled dose. This pattern was observed across the treated groups and the magnitude of decrease was similar between groups receiving H3Vκ2 at 10 mg/kg/dose, H3Vκ2 at 40 mg/kg/dose, and H3E8 at 40 mg/kg/dose. No changes were observed in the relative percentage of CD45+/CD14+/FcRn+ for extra-cellular FcRn expression in CD14+ monocytes.

When taking into account the overall variability and lack of trends at each time point, there were no SYNT001-H3Vk2 or SYNT001-H3E8-related changes in white blood cell count, in the relative percentages and geomean of CD45+/CD14+/FcRn+ for intra-cellular FcRn expression in CD14+ monocytes in all treated groups during the main and recovery periods.

These data suggest that cell surface monocyte FcRn expression may be used as a surrogate marker for anti-FcRn antibody drug levels.

TABLE 15

Monocyte FcRn expression level

| | Group 1 | | Group 2 | | Group 2 | | Group 4 | |
|---|---|---|---|---|---|---|---|---|
| | Animal ID | Fold Change | Animal ID | Fold Change | Animal ID | Fold Change | Animal ID | Fold Change |
| Day 1 - 2 h | 1001 | 0.88 | 2001 | 0.41 | 3001 | 0.54 | 4001 | 0.34 |
| Day 8 - 0 h | | 0.89 | | 1.14 | | 1.10 | | 0.80 |
| Day 8 - 2 h | | 0.87 | | 0.63 | | 0.61 | | 0.59 |
| Day 15 - 0 h | | 0.88 | | 1.09 | | 1.08 | | 0.86 |
| Day 15 - 2 h | | 0.80 | | 0.72 | | 0.57 | | 0.65 |
| Day 22 - 0 h | | 0.73 | | 0.87 | | 0.88 | | 0.70 |
| Day 22 - 2 h | | 0.82 | | 0.53 | | 0.61 | | 0.48 |
| Day 57 | | 0.82 | | 0.88 | | 0.96 | | 0.77 |
| Day 1 - 2 h | 1002 | 0.82 | 2002 | 0.53 | 3002 | 0.57 | 4002 | 0.73 |
| Day 8 - 0 h | | 1.00 | | 1.11 | | 1.00 | | 1.12 |
| Day 8 - 2 h | | 0.91 | | 0.61 | | 0.55 | | 0.87 |
| Day 15 - 0 h | | 0.97 | | 1.20 | | 1.15 | | 0.92 |
| Day 15 - 2 h | | 0.90 | | 0.77 | | 0.61 | | 0.65 |
| Day 22 - 0 h | | 0.73 | | 0.81 | | 0.69 | | 0.77 |
| Day 22 - 2 h | | 0.78 | | 0.59 | | 0.54 | | 0.59 |
| Day 57 | | 0.96 | | 0.99 | | 0.94 | | 0.92 |
| Day 1 - 2 h | 1003 | clotted | 2003 | 0.57 | 3003 | 0.70 | 4003 | 0.6 |
| Day 8 - 0 h | | 0.95 | | 1.00 | | 1.06 | | 1.11 |
| Day 8 - 2 h | | 0.90 | | 0.59 | | 0.71 | | 0.82 |
| Day 15 - 0 h | | 0.97 | | 1.01 | | 0.95 | | 1.06 |
| Day 15 - 2 h | | 0.88 | | 0.62 | | 0.68 | | 0.72 |
| Day 22 - 0 h | | 0.73 | | 0.71 | | 0.77 | | 0.89 |
| Day 22 - 2 h | | 0.78 | | 0.50 | | 0.59 | | 0.65 |
| Day 57 | | 0.82 | | 0.87 | | 1.08 | | 1.05 |

Example 12

X-Ray Structure Determination of Human FcRn:H3Vk2 Fab Binding Complex at 2.4 Å Resolution Nucleotide sequences corresponding to the secreted soluble portions of the extracellular domain of the human FcRn receptor (alpha p51 and beta-2M subunits) were separately cloned into mammalian expression plasmids and sequence verified. The alpha subunit contained a D125A mutation to produce a non-glycosylated protein. Additionally, a TEV protease site followed by a polyhistidine tag was fused to the C-terminus of the alpha subunit to assist purification.

Adherent HEK293 cells were co-transfected with expression plasmids coding for the alpha and beta subunits and single colonies were isolated under hygromycin selection and screened for expression. The highest expressing clone was adapted to suspension culture and expanded for protein production. Secreted FcRn was purified from cell media using a nickel affinity and gel filtration chromatography. The purification tag was removed using TEV protease prior to complex formation and crystallization. Gel filtration profile and SDS-PAGE analysis of purified FcRn indicated both subunits (alpha chain and beta chain) of the FcRn heterodimer. Yields of approximately 1 mg of purified FcRn per liter of cell culture was obtained. Biological activity was verified through binding of purified human FcRn to human IgG-sepharose at low pH (5.5) followed by elution at high pH (8.5).

H3Vk2 Fab was produced and purified from the H3Vk2 antibody by papain digestion and mixed with purified FcRn in a 1:1 stoichiometric ratio. Crystals of the FcRn:Fab complex were grown at 4° C. in a crystallization buffer containing 0.1 M CHES (pH 9.5) and 50% PEG200. Complex formation was verified through SDS-PAGE and silver staining of a washed crystal.

X-ray diffraction data to 2.4 Å resolution were collected from beamline NE-CAT 24-ID-E and processed. The structure of the FcRn:H3Vk Fab complex was solved by molecular replacement techniques and refined using conventional crystallography software. The structure of the FcRn:H3Vk2 Fab complex was resolved to 2.4 Å resolution with excellent geometry and refinement statistics. H3Vk2 Fab was observed to be bound to FcRn in a 1:1 stoichiometric ratio.

The results indicate that residues at positions 85-88, 113-116, and 130-133 of the alpha chain of human FcRn (SEQ ID NO: 79) lie at the interface between FcRn and H3VK2, e.g. these residues form a portion of the conformational epitope recognized by H3VK2. Additionally, residues 1-3 and 59 of the beta chain of human FcRn (SEQ ID NO: 80) lie at the interface between FcRn and H3VK2. The overall interaction between FcRn and H3VK2 involves hydrogen bonding, hydrophobic interactions and Van der Walls contacts, as well as an ionic interaction between R103 of the heavy chain of H3VK2 and E133 of SEQ ID NO: 79, which formed a salt bridge. Additionally a π-π (pi-pi) interaction was observed between the side chain of Y52 of H3VK2 heavy chain and the side chain of E115 of SEQ ID NO: 79. Furthermore, a displacement of up to 3 Å was observed in the FcRn:H3VK2 Fab complex, along residues 58-80 and 145-171 of the FcRn alpha chain (SEQ ID NO: 79).

The following sequence relates to amino acid residues 1-267 the alpha chain of human FcRn:

(SEQ ID NO: 79)
AESHLSLLYHLTAVSSPAPGTPAFWVSGWLGPQQYLSYNSLRGEAEPCG

AWVWENQVSWYWEKETTDLRIKEKLFLEAFKALGGKGPYTLQGLLGCEL

GPDNTSVPTAKFALNGEEFMNFDLKQGTWGGDWPEALAISQRWQQQDKA

ANKELTFLLFSCPHRLREHLERGRGNLEWKEPPSMRLKARPSSPGFSVL

TCSAFSFYPPELQLRFLRNGLAAGTGQGDFGPNSDGSFHASSSLTVKSG

DEHHYCCIVQHAGLAQPLRVEL

The following sequence relates to amino acid residues 1-99 of the beta chain (beta-2-microglobulin) of human FcRn:

(SEQ ID NO: 80)
IQRTPKIQVYSRHPAENGKSNFLNCYVSGFHPSDIEVDLLKNGERIEKVE
HSDLSFSKDWSFYLLYYTEFTPTEKDEYACRVNHVTLSQPKIVKWDRDM.

The underlined regions represent the binding site of H3VK2 to the alpha chain and beta chain of human FcRn as evidenced by the resolution of the FcRn:H3VK2 Fab complex. See also Table 16 below for a summary

TABLE 16

| Residues | Sequence |
|---|---|
| Alpha Chain (SEQ ID NO: 79) | |
| 85-88 | KGPY |
| 113-116 | NGEE |
| 130

```
<400> SEQUENCE: 4

Glu Ile Tyr Pro Arg Ser Gly Asn Thr Tyr Tyr Asn Glu Lys Phe Lys
1               5                   10                  15

Gly

<210> SEQ ID NO 5
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 5 aag gca agt gac cac att aat aat tgg tta gcc                          33
Lys Ala Ser Asp His Ile Asn Asn Trp Leu Ala
1               5                   10

<210> SEQ ID NO 6
<211> LENGTH: 11
<212> TYPE: PRT
<213> ORGANISM: Mus musculus

<400> SEQUENCE: 6

Lys Ala Ser Asp His Ile Asn Asn Trp Leu Ala
1               5                   10

<210> SEQ ID NO 7
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 7 ggt gca acc agt ttg gaa act                                          21
Gly Ala Thr Ser Leu Glu Thr
1               5

<210> SEQ ID NO 8
<211> LENGTH: 7
<212> TYPE: PRT
<213> ORGANISM: Mus musculus

<400> SEQUENCE: 8

Gly Ala Thr Ser Leu Glu Thr
1               5

<210> SEQ ID NO 9
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 9 caa cag tat tgg agt act ccg tac acg                                  27
Gln Gln Tyr Trp Ser Thr Pro Tyr Thr
1               5

<210> SEQ ID NO 10
<211> LENGTH: 9
<212> TYPE: PRT
<213> ORGANISM: Mus musculus
```

<400> SEQUENCE: 10

Gln Gln Tyr Trp Ser Thr Pro Tyr Thr
1               5

<210> SEQ ID NO 11
<211> LENGTH: 354
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(354)
<220> FEATURE:
<221> NAME/KEY: misc_feature
<222> LOCATION: (91)..(105)
<223> OTHER INFORMATION: The "n" stands for a, g, c, or t
<220> FEATURE:
<221> NAME/KEY: misc_feature
<222> LOCATION: (91)..(105)
<223> OTHER INFORMATION: CDR
<220> FEATURE:
<221> NAME/KEY: misc_feature
<222> LOCATION: (148)..(198)
<223> OTHER INFORMATION: The "n" stands for a, g, c, or t
<220> FEATURE:
<221> NAME/KEY: misc_feature
<222> LOCATION: (148)..(198)
<223> OTHER INFORMATION: CDR
<220> FEATURE:
<221> NAME/KEY: misc_feature
<222> LOCATION: (295)..(321)
<223> OTHER INFORMATION: The "n" stands for a, g, c, or t
<220> FEATURE:
<221> NAME/KEY: misc_feature
<222> LOCATION: (295)..(321)
<223> OTHER INFORMATION: CDR

<400> SEQUENCE: 11

| cag gtt cag ctg gtg cag tct gga gct gag ctg aag aag cct ggg gct | 48 |
|---|---|
| Gln Val Gln Leu Val Gln Ser Gly Ala Glu Leu Lys Lys Pro Gly Ala | |
| 1               5                   10                  15 | |

| tca gtg aag ctg tcc tgc aag gct tct ggc tac acc ttc aca nnn nnn | 96 |
|---|---|
| Ser Val Lys Leu Ser Cys Lys Ala Ser Gly Tyr Thr Phe Thr Xaa Xaa | |
|         20                  25                  30 | |

| nnn nnn nnn tgg gtg aag cag gcc act gga cag ggc ctt gag tgg att | 144 |
|---|---|
| Xaa Xaa Xaa Trp Val Lys Gln Ala Thr Gly Gln Gly Leu Glu Trp Ile | |
|     35                  40                  45 | |

| gga nnn nnn nnn nnn nnn nnn nnn nnn nnn nnn nnn nnn nnn nnn | 192 |
|---|---|
| Gly Xaa Xaa Xaa Xaa Xaa Xaa Xaa Xaa Xaa Xaa Xaa Xaa Xaa Xaa | |
| 50                  55                  60 | |

| nnn nnn aga gcc aca ctg act gca gac aaa tcc acg agc aca gcg tac | 240 |
|---|---|
| Xaa Xaa Arg Ala Thr Leu Thr Ala Asp Lys Ser Thr Ser Thr Ala Tyr | |
| 65                  70                  75                  80 | |

| atg gag ctc cgc agc ctg aga tct gag gac tct gcg gtc tat ttc tgt | 288 |
|---|---|
| Met Glu Leu Arg Ser Leu Arg Ser Glu Asp Ser Ala Val Tyr Phe Cys | |
|             85                  90                  95 | |

| gca aga nnn nnn nnn nnn nnn nnn nnn nnn nnn cgg ggc aca ggg acc | 336 |
|---|---|
| Ala Arg Xaa Xaa Xaa Xaa Xaa Xaa Xaa Xaa Xaa Arg Gly Thr Gly Thr | |
|             100                 105                 110 | |

| acg gtc acc gtc tcc tca | 354 |
|---|---|
| Thr Val Thr Val Ser Ser | |
|         115 | |

<210> SEQ ID NO 12
<211> LENGTH: 118
<212> TYPE: PRT
<213> ORGANISM: Artificial Sequence

```
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (32)..(32)
<223> OTHER INFORMATION: The 'Xaa' at location 32 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (34)..(34)
<223> OTHER INFORMATION: The 'Xaa' at location 34 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (35)..(35)
<223> OTHER INFORMATION: The 'Xaa' at location 35 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (51)..(51)
<223> OTHER INFORMATION: The 'Xaa' at location 51 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (52)..(52)
<223> OTHER INFORMATION: The 'Xaa' at location 52 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (53)..(53)
<223> OTHER INFORMATION: The 'Xaa' at location 53 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (54)..(54)
<223> OTHER INFORMATION: The 'Xaa' at location 54 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (55)..(55)
<223> OTHER INFORMATION: The 'Xaa' at location 55 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (56)..(56)
<223> OTHER INFORMATION: The 'Xaa' at location 56 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (57)..(57)
<223> OTHER INFORMATION: The 'Xaa' at location 57 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
```

```
<221> NAME/KEY: misc_feature
<222> LOCATION: (58)..(58)
<223> OTHER INFORMATION: The 'Xaa' at location 58 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (59)..(59)
<223> OTHER INFORMATION: The 'Xaa' at location 59 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (60)..(60)
<223> OTHER INFORMATION: The 'Xaa' at location 60 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (61)..(61)
<223> OTHER INFORMATION: The 'Xaa' at location 61 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (62)..(62)
<223> OTHER INFORMATION: The 'Xaa' at location 62 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (63)..(63)
<223> OTHER INFORMATION: The 'Xaa' at location 63 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (64)..(64)
<223> OTHER INFORMATION: The 'Xaa' at location 64 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (65)..(65)
<223> OTHER INFORMATION: The 'Xaa' at location 65 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (66)..(66)
<223> OTHER INFORMATION: The 'Xaa' at location 66 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (99)..(99)
<223> OTHER INFORMATION: The 'Xaa' at location 99 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (100)..(100)
<223> OTHER INFORMATION: The 'Xaa' at location 100 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (101)..(101)
<223> OTHER INFORMATION: The 'Xaa' at location 101 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (102)..(102)
<223> OTHER INFORMATION: The 'Xaa' at location 102 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
```

-continued

```
<222> LOCATION: (103)..(103)
<223> OTHER INFORMATION: The 'Xaa' at location 103 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (104)..(104)
<223> OTHER INFORMATION: The 'Xaa' at location 104 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (105)..(105)
<223> OTHER INFORMATION: The 'Xaa' at location 105 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (106)..(106)
<223> OTHER INFORMATION: The 'Xaa' at location 106 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (107)..(107)
<223> OTHER INFORMATION: The 'Xaa' at location 107 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<223> OTHER INFORMATION: Synthetic Construct

<400> SEQUENCE: 12

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Xaa Xaa
            20                  25                  30

Xaa Xaa Xaa Trp Val Lys Gln Ala Thr Gly Gln Gly Leu Glu Trp Ile
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Xaa Xaa Xaa Xaa Xaa Xaa Xaa Xaa Arg Gly Thr Gly Thr
            100                 105                 110

Thr Val Thr Val Ser Ser
        115

<210> SEQ ID NO 13
<211> LENGTH: 354
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(354)
<220> FEATURE:
<221> NAME/KEY: misc_feature
<222> LOCATION: (91)..(105)
<223> OTHER INFORMATION: CDR
<220> FEATURE:
<221> NAME/KEY: misc_feature
<222> LOCATION: (91)..(105)
<223> OTHER INFORMATION: The "n" stands for a, g, c, or t
<220> FEATURE:
<221> NAME/KEY: misc_feature
<222> LOCATION: (148)..(198)
<223> OTHER INFORMATION: CDR
```

<220> FEATURE:
<221> NAME/KEY: misc_feature
<222> LOCATION: (148)..(198)
<223> OTHER INFORMATION: The "n" stands for a, g, c, or t
<220> FEATURE:
<221> NAME/KEY: misc_feature
<222> LOCATION: (295)..(321)
<223> OTHER INFORMATION: CDR
<220> FEATURE:
<221> NAME/KEY: misc_feature
<222> LOCATION: (295)..(321)
<223> OTHER INFORMATION: The "n" stands for a, g, c, or t

<400> SEQUENCE: 13

```
cag gtt cag ctg gtg cag tct gga gct gag gtg aag aag cct ggg gct      48
Gln Val Gln Leu Val Gln Ser Gly Ala Glu Val Lys Lys Pro Gly Ala
1               5                   10                  15 tca gtg aag ctg tcc tgc aag gct tct ggc tac acc ttc aca nnn nnn      96
Ser Val Lys Leu Ser Cys Lys Ala Ser Gly Tyr Thr Phe Thr Xaa Xaa
            20                  25                  30 nnn nnn nnn tgg gtg aag cag gcc cct gga cag ggc ctt gag tgg att     144
Xaa Xaa Xaa Trp Val Lys Gln Ala Pro Gly Gln Gly Leu Glu Trp Ile
        35                  40                  45 gga nnn nnn nnn nnn nnn nnn nnn nnn nnn nnn nnn nnn nnn              192
Gly Xaa Xaa Xaa Xaa Xaa Xaa Xaa Xaa Xaa Xaa Xaa Xaa Xaa
    50                  55                  60 nnn nnn aga gcc aca ctg act gca gac aaa tcc acg agc aca gcg tac     240
Xaa Xaa Arg Ala Thr Leu Thr Ala Asp Lys Ser Thr Ser Thr Ala Tyr
65                  70                  75                  80 atg gag ctc cgc agc ctg aga tct gag gac act gcg gtc tat ttc tgt     288
Met Glu Leu Arg Ser Leu Arg Ser Glu Asp Thr Ala Val Tyr Phe Cys
                85                  90                  95 gca aga nnn nnn nnn nnn nnn nnn nnn nnn nnn cgg ggc aca ggg acc     336
Ala Arg Xaa Xaa Xaa Xaa Xaa Xaa Xaa Xaa Xaa Arg Gly Thr Gly Thr
                100                 105                 110 acg gtc acc gtc tcc tca                                              354
Thr Val Thr Val Ser Ser
        115
```

<210> SEQ ID NO 14
<211> LENGTH: 118
<212> TYPE: PRT
<213> ORGANISM: Artificial Sequence
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (32)..(32)
<223> OTHER INFORMATION: The 'Xaa' at location 32 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (34)..(34)
<223> OTHER INFORMATION: The 'Xaa' at location 34 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (35)..(35)

```
<223> OTHER INFORMATION: The 'Xaa' at location 35 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (51)..(51)
<223> OTHER INFORMATION: The 'Xaa' at location 51 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (52)..(52)
<223> OTHER INFORMATION: The 'Xaa' at location 52 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (53)..(53)
<223> OTHER INFORMATION: The 'Xaa' at location 53 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (54)..(54)
<223> OTHER INFORMATION: The 'Xaa' at location 54 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (55)..(55)
<223> OTHER INFORMATION: The 'Xaa' at location 55 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (56)..(56)
<223> OTHER INFORMATION: The 'Xaa' at location 56 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (57)..(57)
<223> OTHER INFORMATION: The 'Xaa' at location 57 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (58)..(58)
<223> OTHER INFORMATION: The 'Xaa' at location 58 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (59)..(59)
<223> OTHER INFORMATION: The 'Xaa' at location 59 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (60)..(60)
<223> OTHER INFORMATION: The 'Xaa' at location 60 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (61)..(61)
<223> OTHER INFORMATION: The 'Xaa' at location 61 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (62)..(62)
<223> OTHER INFORMATION: The 'Xaa' at location 62 stands for Lys, Asn,
```

-continued

```
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (63)..(63)
<223> OTHER INFORMATION: The 'Xaa' at location 63 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (64)..(64)
<223> OTHER INFORMATION: The 'Xaa' at location 64 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (65)..(65)
<223> OTHER INFORMATION: The 'Xaa' at location 65 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (66)..(66)
<223> OTHER INFORMATION: The 'Xaa' at location 66 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (99)..(99)
<223> OTHER INFORMATION: The 'Xaa' at location 99 stands for Lys, Asn,
        Arg, Ser, Thr, Ile, Met, Glu, Asp, Gly, Ala, Val, Gln, His, Pro,
        Leu, Tyr, Trp, Cys, or Phe.
<220> FEATURE:
<221> NAME/KEY: misc_feature
<222> LOCATION: (100)..(100)
<223> OTHER INFORMATION: The 'Xaa' at location 100 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (101)..(101)
<223> OTHER INFORMATION: The 'Xaa' at location 101 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (102)..(102)
<223> OTHER INFORMATION: The 'Xaa' at location 102 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (103)..(103)
<223> OTHER INFORMATION: The 'Xaa' at location 103 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (104)..(104)
<223> OTHER INFORMATION: The 'Xaa' at location 104 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (105)..(105)
<223> OTHER INFORMATION: The 'Xaa' at location 105 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (106)..(106)
<223> OTHER INFORMATION: The 'Xaa' at location 106 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (107)..(107)
<223> OTHER INFORMATION: The 'Xaa' at location 107 stands for Lys,
        Asn, Arg, Ser, Thr, Ile, Met, Glu, Asp, Gly, Ala, Val, Gln, His,
```

Pro, Leu, Tyr, Trp, Cys, or Phe.
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Xaa Xaa
            20                  25                  30

Xaa Xaa Xaa Trp Val Lys Gln Ala Pro Gly Gln Gly Leu Glu Trp Ile
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Ala Thr Leu Thr Ala Asp Lys Ser Thr Ser Thr Ala Tyr
65                  70                  75                  80

Met Glu Leu Arg Ser Leu Arg Ser Glu Asp Thr Ala Val Tyr Phe Cys
                85                  90                  95

Ala Arg Xaa Xaa Xaa Xaa Xaa Xaa Xaa Xaa Arg Gly Thr Gly Thr
            100                 105                 110

Thr Val Thr Val Ser Ser
        115

<210> SEQ ID NO 15
<211> LENGTH: 354
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(354)
<220> FEATURE:
<221> NAME/KEY: misc_feature
<222> LOCATION: (91)..(105)
<223> OTHER INFORMATION: The "n" stands for a, g, c, or t
<220> FEATURE:
<221> NAME/KEY: misc_feature
<222> LOCATION: (91)..(105)
<223> OTHER INFORMATION: CDR
<220> FEATURE:
<221> NAME/KEY: misc_feature
<222> LOCATION: (148)..(198)
<223> OTHER INFORMATION: The "n" stands for a, g, c, or t
<220> FEATURE:
<221> NAME/KEY: misc_feature
<222> LOCATION: (148)..(198)
<223> OTHER INFORMATION: CDR
<220> FEATURE:
<221> NAME/KEY: misc_feature
<222> LOCATION: (295)..(321)
<223> OTHER INFORMATION: The "n" stands for a, g, c, or t
<220> FEATURE:
<221> NAME/KEY: misc_feature
<222> LOCATION: (295)..(321)
<223> OTHER INFORMATION: CDR

<400> SEQUENCE: 15 cag gtt cag ctg gtg cag tct gga gct gag gtg aag aag cct ggg gct      48
Gln Val Gln Leu Val Gln Ser Gly Ala Glu Val Lys Lys Pro Gly Ala
1               5                   10                  15 tca gtg aag gtg tcc tgc aag gct tct ggc tac acc ttc aca nnn nnn      96
Ser Val Lys Val Ser Cys Lys Ala Ser Gly Tyr Thr Phe Thr Xaa Xaa
            20                  25                  30 nnn nnn nnn tgg gtg cga cag gcc cct gga cag ggc ctt gag tgg att     144
Xaa Xaa Xaa Trp Val Arg Gln Ala Pro Gly Gln Gly Leu Glu Trp Ile
        35                  40                  45

```
gga nnn nnn nnn nnn nnn nnn nnn nnn nnn nnn nnn nnn nnn         192
Gly Xaa Xaa Xaa Xaa Xaa Xaa Xaa Xaa Xaa Xaa Xaa Xaa Xaa
    50              55                  60 nnn nnn aga gcc aca att act gca gac aaa tcc acg agc aca gcg tac 240
Xaa Xaa Arg Ala Thr Ile Thr Ala Asp Lys Ser Thr Ser Thr Ala Tyr
65              70                  75                  80 atg gag ctc cgc agc ctg aga tct gag gac act gcg gtc tat tac tgt 288
Met Glu Leu Arg Ser Leu Arg Ser Glu Asp Thr Ala Val Tyr Tyr Cys
                85                  90                  95 gca aga nnn nnn nnn nnn nnn nnn nnn nnn cgg ggc aca ggg acc     336
Ala Arg Xaa Xaa Xaa Xaa Xaa Xaa Xaa Xaa Arg Gly Thr Gly Thr
            100                 105             110 acg gtc acc gtc tcc tca                                         354
Thr Val Thr Val Ser Ser
        115
```

```
<210> SEQ ID NO 16
<211> LENGTH: 118
<212> TYPE: PRT
<213> ORGANISM: Artificial Sequence
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (32)..(32)
<223> OTHER INFORMATION: The 'Xaa' at location 32 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (34)..(34)
<223> OTHER INFORMATION: The 'Xaa' at location 34 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (35)..(35)
<223> OTHER INFORMATION: The 'Xaa' at location 35 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (51)..(51)
<223> OTHER INFORMATION: The 'Xaa' at location 51 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (52)..(52)
<223> OTHER INFORMATION: The 'Xaa' at location 52 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (53)..(53)
<223> OTHER INFORMATION: The 'Xaa' at location 53 stands for Lys, Asn,
      Arg, Ser, Thr, Ile, Met, Glu, Asp, Gly, Ala, Val, Gln, His, Pro,
      Leu, Tyr, Trp, Cys, or Phe.
```

```
<220> FEATURE:
<221> NAME/KEY: misc_feature
<222> LOCATION: (54)..(54)
<223> OTHER INFORMATION: The 'Xaa' at location 54 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (55)..(55)
<223> OTHER INFORMATION: The 'Xaa' at location 55 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (56)..(56)
<223> OTHER INFORMATION: The 'Xaa' at location 56 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (57)..(57)
<223> OTHER INFORMATION: The 'Xaa' at location 57 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (58)..(58)
<223> OTHER INFORMATION: The 'Xaa' at location 58 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (59)..(59)
<223> OTHER INFORMATION: The 'Xaa' at location 59 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (60)..(60)
<223> OTHER INFORMATION: The 'Xaa' at location 60 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (61)..(61)
<223> OTHER INFORMATION: The 'Xaa' at location 61 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (62)..(62)
<223> OTHER INFORMATION: The 'Xaa' at location 62 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (63)..(63)
<223> OTHER INFORMATION: The 'Xaa' at location 63 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (64)..(64)
<223> OTHER INFORMATION: The 'Xaa' at location 64 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (65)..(65)
<223> OTHER INFORMATION: The 'Xaa' at location 65 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (66)..(66)
<223> OTHER INFORMATION: The 'Xaa' at location 66 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
```

```
<221> NAME/KEY: misc_feature
<222> LOCATION: (99)..(99)
<223> OTHER INFORMATION: The 'Xaa' at location 99 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (100)..(100)
<223> OTHER INFORMATION: The 'Xaa' at location 100 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (101)..(101)
<223> OTHER INFORMATION: The 'Xaa' at location 101 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (102)..(102)
<223> OTHER INFORMATION: The 'Xaa' at location 102 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (103)..(103)
<223> OTHER INFORMATION: The 'Xaa' at location 103 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (104)..(104)
<223> OTHER INFORMATION: The 'Xaa' at location 104 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (105)..(105)
<223> OTHER INFORMATION: The 'Xaa' at location 105 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (106)..(106)
<223> OTHER INFORMATION: The 'Xaa' at location 106 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (107)..(107)
<223> OTHER INFORMATION: The 'Xaa' at location 107 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<223> OTHER INFORMATION: Synthetic Construct

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Xaa Xaa Xaa Trp Val Arg Gln Ala Pro Gly Gln Gly Leu Glu Trp Ile
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Ala Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Xaa Xaa Xaa Xaa Xaa Xaa Xaa Xaa Arg Gly Thr Gly Thr
            100                 105                 110
```

```
Thr Val Thr Val Ser Ser
        115

<210> SEQ ID NO 17
<211> LENGTH: 354
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(354)
<220> FEATURE:
<221> NAME/KEY: misc_feature
<222> LOCATION: (91)..(105)
<223> OTHER INFORMATION: The "n" stands for a, g, c, or t
<220> FEATURE:
<221> NAME/KEY: misc_feature
<222> LOCATION: (91)..(105)
<223> OTHER INFORMATION: CDR
<220> FEATURE:
<221> NAME/KEY: misc_feature
<222> LOCATION: (148)..(198)
<223> OTHER INFORMATION: The "n" stands for a, g, c, or t
<220> FEATURE:
<221> NAME/KEY: misc_feature
<222> LOCATION: (148)..(198)
<223> OTHER INFORMATION: CDR
<220> FEATURE:
<221> NAME/KEY: misc_feature
<222> LOCATION: (295)..(321)
<223> OTHER INFORMATION: The "n" stands for a, g, c, or t
<220> FEATURE:
<221> NAME/KEY: misc_feature
<222> LOCATION: (295)..(321)
<223> OTHER INFORMATION: CDR

<400> SEQUENCE: 17 cag gtt cag ctg gtg cag tct gga gct gag gtg aag aag cct ggg gct      48
Gln Val Gln Leu Val Gln Ser Gly Ala Glu Val Lys Lys Pro Gly Ala
1               5                   10                  15 tca gtg aag gtg tcc tgc aag gct tct ggc tac acc ttc aca nnn nnn      96
Ser Val Lys Val Ser Cys Lys Ala Ser Gly Tyr Thr Phe Thr Xaa Xaa
            20                  25                  30 nnn nnn nnn tgg gtg cga cag gcc cct gga cag ggc ctt gag tgg att     144
Xaa Xaa Xaa Trp Val Arg Gln Ala Pro Gly Gln Gly Leu Glu Trp Ile
        35                  40                  45 gga nnn nnn nnn nnn nnn nnn nnn nnn nnn nnn nnn nnn nnn nnn         192
Gly Xaa Xaa Xaa Xaa Xaa Xaa Xaa Xaa Xaa Xaa Xaa Xaa Xaa Xaa
    50                  55                  60 nnn nnn aga gtc aca att act gca gac aaa tcc acg agc aca gcg tac     240
Xaa Xaa Arg Val Thr Ile Thr Ala Asp Lys Ser Thr Ser Thr Ala Tyr
65                  70                  75                  80 atg gag ctc cgc agc ctg aga tct gag gac act gcg gtc tat tac tgt     288
Met Glu Leu Arg Ser Leu Arg Ser Glu Asp Thr Ala Val Tyr Tyr Cys
                85                  90                  95 gca aga nnn nnn nnn nnn nnn nnn nnn nnn nnn cgg ggc aca ggg acc     336
Ala Arg Xaa Xaa Xaa Xaa Xaa Xaa Xaa Xaa Xaa Arg Gly Thr Gly Thr
            100                 105                 110 acg gtc acc gtc tcc tca                                             354
Thr Val Thr Val Ser Ser
        115

<210> SEQ ID NO 18
<211> LENGTH: 118
<212> TYPE: PRT
<213> ORGANISM: Artificial Sequence
<220> FEATURE:
<221> NAME/KEY: misc_feature
```

```
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (32)..(32)
<223> OTHER INFORMATION: The 'Xaa' at location 32 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (34)..(34)
<223> OTHER INFORMATION: The 'Xaa' at location 34 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (35)..(35)
<223> OTHER INFORMATION: The 'Xaa' at location 35 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (51)..(51)
<223> OTHER INFORMATION: The 'Xaa' at location 51 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (52)..(52)
<223> OTHER INFORMATION: The 'Xaa' at location 52 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (53)..(53)
<223> OTHER INFORMATION: The 'Xaa' at location 53 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (54)..(54)
<223> OTHER INFORMATION: The 'Xaa' at location 54 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (55)..(55)
<223> OTHER INFORMATION: The 'Xaa' at location 55 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (56)..(56)
<223> OTHER INFORMATION: The 'Xaa' at location 56 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (57)..(57)
<223> OTHER INFORMATION: The 'Xaa' at location 57 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (58)..(58)
```

```
<223> OTHER INFORMATION: The 'Xaa' at location 58 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (59)..(59)
<223> OTHER INFORMATION: The 'Xaa' at location 59 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (60)..(60)
<223> OTHER INFORMATION: The 'Xaa' at location 60 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (61)..(61)
<223> OTHER INFORMATION: The 'Xaa' at location 61 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (62)..(62)
<223> OTHER INFORMATION: The 'Xaa' at location 62 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (63)..(63)
<223> OTHER INFORMATION: The 'Xaa' at location 63 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (64)..(64)
<223> OTHER INFORMATION: The 'Xaa' at location 64 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (65)..(65)
<223> OTHER INFORMATION: The 'Xaa' at location 65 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (66)..(66)
<223> OTHER INFORMATION: The 'Xaa' at location 66 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (99)..(99)
<223> OTHER INFORMATION: The 'Xaa' at location 99 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (100)..(100)
<223> OTHER INFORMATION: The 'Xaa' at location 100 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (101)..(101)
<223> OTHER INFORMATION: The 'Xaa' at location 101 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (102)..(102)
<223> OTHER INFORMATION: The 'Xaa' at location 102 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (103)..(103)
<223> OTHER INFORMATION: The 'Xaa' at location 103 stands for Lys,
```

```
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (104)..(104)
<223> OTHER INFORMATION: The 'Xaa' at location 104 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (105)..(105)
<223> OTHER INFORMATION: The 'Xaa' at location 105 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (106)..(106)
<223> OTHER INFORMATION: The 'Xaa' at location 106 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<221> NAME/KEY: misc_feature
<222> LOCATION: (107)..(107)
<223> OTHER INFORMATION: The 'Xaa' at location 107 stands for Lys,
        Asn, Arg, Ser, Thr, Ile, Met, Glu, Asp, Gly, Ala, Val, Gln, His,
        Pro, Leu, Tyr, Trp, Cys, or Phe.
<220> FEATURE:
<223> OTHER INFORMATION: Synthetic Construct

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Xaa Xaa Xaa Trp Val Arg Gln Ala Pro Gly Gln Gly Leu Glu Trp Ile
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Xaa Xaa Xaa Xaa Xaa Xaa Xaa Xaa Arg Gly Thr Gly Thr
            100                 105                 110

Thr Val Thr Val Ser Ser
        115

<210> SEQ ID NO 19
<211> LENGTH: 321
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(321)

<400> SEQUENCE: 19 gac atc cag atg aca caa tct cct tcc tac ttg tct gca tct gta gga        48
Asp Ile Gln Met Thr Gln Ser Pro Ser Tyr Leu Ser Ala Ser Val Gly
1               5                   10                  15 gac aga gtc acc att act tgc aag gca agt gac cac att aat aat tgg        96
Asp Arg Val Thr Ile Thr Cys Lys Ala Ser Asp His Ile Asn Asn Trp
            20                  25                  30 tta gcc tgg tat cag cag aaa cca gga cag gct cct agg ctc tta ata      144
Leu Ala Trp Tyr Gln Gln Lys Pro Gly Gln Ala Pro Arg Leu Leu Ile
        35                  40                  45
```

```
tct ggt gca acc agt ttg gaa act ggg gtt cct tca aga ttc agt ggc    192
Ser Gly Ala Thr Ser Leu Glu Thr Gly Val Pro Ser Arg Phe Ser Gly
    50                  55                  60 agt gga act gga aag gat tac act ctc acc att agc agt ctt cag act    240
Ser Gly Thr Gly Lys Asp Tyr Thr Leu Thr Ile Ser Ser Leu Gln Thr
65                  70                  75                  80 gaa gat ttt gct acg tat tac tgt caa cag tat tgg agt act ccg tac    288
Glu Asp Phe Ala Thr Tyr Tyr Cys Gln Gln Tyr Trp Ser Thr Pro Tyr
                85                  90                  95 acg ttc gga ggg ggg acc aag gtg gaa ata aaa                         321
Thr Phe Gly Gly Gly Thr Lys Val Glu Ile Lys
                100                 105

<210> SEQ ID NO 20
<211> LENGTH: 107
<212> TYPE: PRT
<213> ORGANISM: Artificial Sequence
<220> FEATURE:
<223> OTHER INFORMATION: Synthetic Construct

<400> SEQUENCE: 20

Asp Ile Gln Met Thr Gln Ser Pro Ser Tyr Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys Gln Gln Tyr Trp Ser Thr Pro Tyr
                85                  90                  95

Thr Phe Gly Gly Gly Thr Lys Val Glu Ile Lys
                100                 105

<210> SEQ ID NO 21
<211> LENGTH: 321
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(321)

<400> SEQUENCE: 21 gac atc cag atg aca caa tct cct tcc tcc ttg tct gca tct gta gga    48
Asp Ile Gln Met Thr Gln Ser Pro Ser Ser Leu Ser Ala Ser Val Gly
1               5                   10                  15 gac aga gtc acc att act tgc aag gca agt gac cac att aat aat tgg    96
Asp Arg Val Thr Ile Thr Cys Lys Ala Ser Asp His Ile Asn Asn Trp
            20                  25                  30 tta gcc tgg tat cag cag aaa cca gga cag gct cct agg ctc tta ata    144
Leu Ala Trp Tyr Gln Gln Lys Pro Gly Gln Ala Pro Arg Leu Leu Ile
        35                  40                  45 tct ggt gca acc agt ttg gaa act ggg gtt cct tca aga ttc agt ggc    192
Ser Gly Ala Thr Ser Leu Glu Thr Gly Val Pro Ser Arg Phe Ser Gly
    50                  55                  60 agt gga act gga aag gat tac act ctc acc att agc agt ctt cag cct    240
Ser Gly Thr Gly Lys Asp Tyr Thr Leu Thr Ile Ser Ser Leu Gln Pro
65                  70                  75                  80
```

```
                 65                  70                  75                  80
gaa gat ttt gct acg tat tac tgt caa cag tat tgg agt act ccg tac       288
Glu Asp Phe Ala Thr Tyr Tyr Cys Gln Gln Tyr Trp Ser Thr Pro Tyr
                 85                  90                  95 acg ttc gga ggg ggg acc aag gtg gaa ata aaa                           321
Thr Phe Gly Gly Gly Thr Lys Val Glu Ile Lys
                100                 105
```

<210> SEQ ID NO 22
<211> LENGTH: 107
<212> TYPE: PRT
<213> ORGANISM: Artificial Sequence
<220> FEATURE:
<223> OTHER INFORMATION: Synthetic Construct

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
                20                  25                  30

Leu Ala Trp Tyr Gln Gln Lys Pro Gly Gln Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Thr Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Tyr
                85                  90                  95

Thr Phe Gly Gly Gly Thr Lys Val Glu Ile Lys
                100                 105
```

<210> SEQ ID NO 23
<211> LENGTH: 321
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(321)

<400> SEQUENCE: 23

```
gac atc cag atg aca caa tct cct tcc tcc ttg tct gca tct gta gga       48
Asp Ile Gln Met Thr Gln Ser Pro Ser Ser Leu Ser Ala Ser Val Gly
1               5                   10                  15 gac aga gtc acc att act tgc aag gca agt gac cac att aat aat tgg       96
Asp Arg Val Thr Ile Thr Cys Lys Ala Ser Asp His Ile Asn Asn Trp
                20                  25                  30 tta gcc tgg tat cag cag aaa cca gga cag gct cct agg ctc tta ata      144
Leu Ala Trp Tyr Gln Gln Lys Pro Gly Gln Ala Pro Arg Leu Leu Ile
            35                  40                  45 tct ggt gca acc agt ttg gaa act ggg gtt cct tca aga ttc agt ggc      192
Ser Gly Ala Thr Ser Leu Glu Thr Gly Val Pro Ser Arg Phe Ser Gly
        50                  55                  60 agt gga tct gga aag gat ttc act ctc acc att agc agt ctt cag cct      240
Ser Gly Ser Gly Lys Asp Phe Thr Leu Thr Ile Ser Ser Leu Gln Pro
65                  70                  75                  80 gaa gat ttt gct acg tat tac tgt caa cag tat tgg agt act ccg tac      288
Glu Asp Phe Ala Thr Tyr Tyr Cys Gln Gln Tyr Trp Ser Thr Pro Tyr
                85                  90                  95 acg ttc gga ggg ggg acc aag gtg gaa ata aaa                          321
```

Thr Phe Gly Gly Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Phe Thr Leu Thr Ile Ser Ser Leu Gln Pro
65                  70                  75                  80

Glu Asp Phe Ala Thr Tyr Tyr Cys Gln Gln Tyr Trp Ser Thr Pro Tyr
                85                  90                  95

Thr Phe Gly Gly Gly Thr Lys Val Glu Ile Lys
            100                 105

<210> SEQ ID NO 25
<211> LENGTH: 321
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(321)

<400> SEQUENCE: 25 gac atc cag atg aca caa tct cct tcc tcc ttg tct gca tct gta gga        48
Asp Ile Gln Met Thr Gln Ser Pro Ser Ser Leu Ser Ala Ser Val Gly
1               5                   10                  15 gac aga gtc acc att act tgc aag gca agt gac cac att aat aat tgg        96
Asp Arg Val Thr Ile Thr Cys Lys Ala Ser Asp His Ile Asn Asn Trp
            20                  25                  30 tta gcc tgg tat cag cag aaa cca gga cag gct cct agg ctc tta ata       144
Leu Ala Trp Tyr Gln Gln Lys Pro Gly Gln Ala Pro Arg Leu Leu Ile
        35                  40                  45 tct ggt gca acc agt ttg gaa act ggg gtt cct tca aga ttc agt ggc       192
Ser Gly Ala Thr Ser Leu Glu Thr Gly Val Pro Ser Arg Phe Ser Gly
    50                  55                  60 agt gga tct gga aca gat ttc act ctc acc att agc agt ctt cag cct       240
Ser Gly Ser Gly Thr Asp Phe Thr Leu Thr Ile Ser Ser Leu Gln Pro
65                  70                  75                  80 gaa gat ttt gct acg tat tac tgt caa cag tat tgg agt act ccg tac       288
Glu Asp Phe Ala Thr Tyr Tyr Cys Gln Gln Tyr Trp Ser Thr Pro Tyr
                85                  90                  95 acg ttc gga ggg ggg acc aag gtg gaa ata aaa                           321
Thr Phe Gly Gly Gly Thr Lys Val Glu Ile Lys
            100                 105

<210> SEQ ID NO 26
<211> LENGTH: 107
<212> TYPE: PRT

<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Ser Thr Pro Tyr
                85                  90                  95

Thr Phe Gly Gly Gly Thr Lys Val Glu Ile Lys
            100                 105

<210> SEQ ID NO 27
<211> LENGTH: 9
<212> TYPE: PRT
<213> ORGANISM: Artificial Sequence
<220> FEATURE:
<223> OTHER INFORMATION: Synthesized

<400> SEQUENCE: 27

Ser Thr Thr Val Ser Pro Ala Asp Phe
1               5

<210> SEQ ID NO 28
<211> LENGTH: 118
<212> TYPE: PRT
<213> ORGANISM: Artificial Sequence
<220> FEATURE:
<223> OTHER INFORMATION: affinity matured

<400> SEQUENCE: 28

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Ala Thr Gly Gln Gly Leu Glu Trp Ile
        35                  40                  45

Gly Glu Ile Tyr Pro Arg Ser Gly Asn Thr Tyr Tyr Asn Glu Lys Phe
50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Ser Pro Ala Asp Phe Arg Gly Thr Gly Thr
            100                 105                 110

Thr Val Thr Val Ser Ser
        115

<210> SEQ ID NO 29
<211> LENGTH: 9
<212> TYPE: PRT
<213> ORGANISM: Artificial Sequence

```
<220> FEATURE:
<223> OTHER INFORMATION: affinity matured

<400> SEQUENCE: 29

Ser Thr Thr Val Ser Pro Pro Ile
1               5

<210> SEQ ID NO 30
<211> LENGTH: 118
<212> TYPE: PRT
<213> ORGANISM: Artificial Sequence
<220> FEATURE:
<223> OTHER INFORMATION: affinity matured

<400> SEQUENCE: 30

Gln Val Gln Leu Val Gln Ser Gly Ala Glu Leu Lys Lys Pro Gly Ala
1               5                  10                  15

Ser Val Lys Leu Ser Cys Lys Ala Ser Gly Tyr Thr Phe Thr Ser Tyr
                20                  25                  30

Gly Ile Ser Trp Val Lys Gln Ala Thr Gly Gln Gly Leu Glu Trp Ile
            35                  40                  45

Gly Glu Ile Tyr Pro Arg Ser Gly Asn Thr Tyr Tyr Asn Glu Lys Phe
        50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Ser Pro Pro Ile Trp Gly Thr Gly Thr
            100                 105                 110

Thr Val Thr Val Ser Ser
        115

<210> SEQ ID NO 31
<211> LENGTH: 9
<212> TYPE: PRT
<213> ORGANISM: Artificial Sequence
<220> FEATURE:
<223> OTHER INFORMATION: affinity matured

<400> SEQUENCE: 31

Ser Thr Thr Val Ser Pro Pro Ala His
1               5

<210> SEQ ID NO 32
<211> LENGTH: 118
<212> TYPE: PRT
<213> ORGANISM: Artificial Sequence
<220> FEATURE:
<223> OTHER INFORMATION: affinity matured

<400> SEQUENCE: 32

Gln Val Gln Leu Val Gln Ser Gly Ala Glu Leu Lys Lys Pro Gly Ala
1               5                  10                  15

Ser Val Lys Leu Ser Cys Lys Ala Ser Gly Tyr Thr Phe Thr Ser Tyr
                20                  25                  30

Gly Ile Ser Trp Val Lys Gln Ala Thr Gly Gln Gly Leu Glu Trp Ile
            35                  40                  45

Gly Glu Ile Tyr Pro Arg Ser Gly Asn Thr Tyr Tyr Asn Glu Lys Phe
        50                  55                  60

Lys Gly Arg Ala Thr Leu Thr Ala Asp Lys Ser Thr Ser Thr Ala Tyr
65                  70                  75                  80
```

Met Glu Leu Arg Ser Leu Lys Ser Glu Asp Ser Ala Val Tyr Phe Cys
            85                  90                  95

Ala Arg Ser Thr Thr Val Ser Pro Pro Ala His Trp Gly Thr Gly Thr
            100                 105                 110

Thr Val Thr Val Ser Ser
        115

<210> SEQ ID NO 33
<211> LENGTH: 9
<212> TYPE: PRT
<213> ORGANISM: Artificial Sequence
<220> FEATURE:
<223> OTHER INFORMATION: affinity matured

<400> SEQUENCE: 33

Ser Thr Thr Val Ala Pro Pro Arg Leu
1               5

<210> SEQ ID NO 34
<211> LENGTH: 118
<212> TYPE: PRT
<213> ORGANISM: Artificial Sequence
<220> FEATURE:
<223> OTHER INFORMATION: affinity matured

<400> SEQUENCE: 34

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Ala Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
            85                  90                  95

Ala Arg Ser Thr Thr Val Ala Pro Pro Arg Leu Trp Gly Thr Gly Thr
            100                 105                 110

Thr Val Thr Val Ser Ser
        115

<210> SEQ ID NO 35
<211> LENGTH: 9
<212> TYPE: PRT
<213> ORGANISM: Artificial Sequence
<220> FEATURE:
<223> OTHER INFORMATION: affinity matured

<400> SEQUENCE: 35

Ser Thr Thr Val His Pro Asp Arg Asn
1               5

<210> SEQ ID NO 36
<211> LENGTH: 118
<212> TYPE: PRT
<213> ORGANISM: Artificial Sequence
<220> FEATURE:
<223> OTHER INFORMATION: affinity matured

<400> SEQUENCE: 36

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
                20                  25                  30

Gly Ile Ser Trp Val Lys Gln Ala Thr Gly Gln Gly Leu Glu Trp Ile
                35                  40                  45

Gly Glu Ile Tyr Pro Arg Ser Gly Asn Thr Tyr Tyr Asn Glu Lys Phe
            50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val His Pro Asp Arg Asn Trp Gly Thr Gly Thr
                100                 105                 110

Thr Val Thr Val Ser Ser
        115

<210> SEQ ID NO 37
<211> LENGTH: 9
<212> TYPE: PRT
<213> ORGANISM: Artificial Sequence
<220> FEATURE:
<223> OTHER INFORMATION: affinity matured

<400> SEQUENCE: 37

Ser Thr Thr Val Ser Pro Pro Ala Leu
1               5

<210> SEQ ID NO 38
<211> LENGTH: 118
<212> TYPE: PRT
<213> ORGANISM: Artificial Sequence
<220> FEATURE:
<223> OTHER INFORMATION: affinity matured

<400> SEQUENCE: 38

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
                20                  25                  30

Gly Ile Ser Trp Val Lys Gln Ala Thr Gly Gln Gly Leu Glu Trp Ile
                35                  40                  45

Gly Glu Ile Tyr Pro Arg Ser Gly Asn Thr Tyr Tyr Asn Glu Lys Phe
            50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Ser Pro Pro Ala Leu Trp Gly Thr Gly Thr
                100                 105                 110

Thr Val Thr Val Ser Ser
        115

<210> SEQ ID NO 39
<211> LENGTH: 9
<212> TYPE: PRT
<213> ORGANISM: Artificial Sequence
<220> FEATURE:
<223> OTHER INFORMATION: affinity matured

<400> SEQUENCE: 39

Ser Thr Thr Val His Pro Asp His Asn
1               5

<210> SEQ ID NO 40
<211> LENGTH: 118
<212> TYPE: PRT
<213> ORGANISM: Artificial Sequence
<220> FEATURE:
<223> OTHER INFORMATION: affinity matured

<400> SEQUENCE: 40

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
                20                  25                  30

Gly Ile Ser Trp Val Lys Gln Ala Thr Gly Gln Gly Leu Glu Trp Ile
            35                  40                  45

Gly Glu Ile Tyr Pro Arg Ser Gly Asn Thr Tyr Tyr Asn Glu Lys Phe
        50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val His Pro Asp His Asn Trp Gly Thr Gly Thr
                100                 105                 110

Thr Val Thr Val Ser Ser
            115

<210> SEQ ID NO 41
<211> LENGTH: 9
<212> TYPE: PRT
<213> ORGANISM: Artificial Sequence
<220> FEATURE:
<223> OTHER INFORMATION: affinity matured

<400> SEQUENCE: 41

Ser Thr Thr Val Ser Pro Pro His Leu
1               5

<210> SEQ ID NO 42
<211> LENGTH: 118
<212> TYPE: PRT
<213> ORGANISM: Artificial Sequence
<220> FEATURE:
<223> OTHER INFORMATION: affinity matured

<400> SEQUENCE: 42

Gln Val Gln Leu Val Gln Ser Gly Ala Glu Pro Lys Lys Pro Gly Ala
1               5                   10                  15

Ser Val Lys Leu Ser Cys Lys Ala Ser Gly Tyr Thr Phe Thr Ser Tyr
                20                  25                  30

Gly Ile Ser Trp Val Lys Gln Ala Thr Gly Gln Gly Leu Glu Trp Ile
            35                  40                  45

Gly Glu Ile Tyr Pro Arg Ser Gly Asn Thr Tyr Tyr Asn Glu Lys Phe
        50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys

```
                85                  90                  95
Ala Arg Ser Thr Thr Val Ser Pro Pro His Leu Trp Gly Thr Gly Thr
            100                 105                 110

Thr Val Thr Val Ser Ser
        115

<210> SEQ ID NO 43
<211> LENGTH: 9
<212> TYPE: PRT
<213> ORGANISM: Artificial Sequence
<220> FEATURE:
<223> OTHER INFORMATION: affinity matured

<400> SEQUENCE: 43

Ser Thr Thr Val Ala Pro Pro Leu
1               5

<210> SEQ ID NO 44
<211> LENGTH: 118
<212> TYPE: PRT
<213> ORGANISM: Artificial Sequence
<220> FEATURE:
<223> OTHER INFORMATION: affinity matured

<400> SEQUENCE: 44

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Ala Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Ala Pro Pro Leu Trp Gly Thr Gly Thr
            100                 105                 110

Thr Val Thr Val Ser Ser
        115

<210> SEQ ID NO 45
<211> LENGTH: 9
<212> TYPE: PRT
<213> ORGANISM: Artificial Sequence
<220> FEATURE:
<223> OTHER INFORMATION: affinity matured

<400> SEQUENCE: 45

Ser Thr Thr Val Ser Pro Pro His Leu
1               5

<210> SEQ ID NO 46
<211> LENGTH: 118
<212> TYPE: PRT
<213> ORGANISM: Artificial Sequence
<220> FEATURE:
<223> OTHER INFORMATION: affinity matured

<400> SEQUENCE: 46

Gln Val Gln Leu Val Gln Ser Gly Ala Glu Leu Lys Lys Pro Gly Ala
```

```
            1               5                  10                 15
Ser Val Lys Leu Ser Cys Lys Ala Ser Gly Tyr Thr Phe Thr Ser Tyr
            20                 25                 30

Gly Ile Ser Trp Val Lys Gln Ala Thr Gly Gln Gly Leu Glu Trp Ile
            35                 40                 45

Gly Glu Ile Tyr Pro Arg Ser Gly Asn Thr Tyr Tyr Asn Glu Lys Phe
        50                 55                 60

Lys Gly Arg Ala Thr Leu Thr Ala Asp Lys Ser Thr Ser Thr Ala Tyr
65                      70                 75                 80

Met Glu Leu Arg Ser Leu Arg Ser Glu Asp Ser Ala Val Tyr Phe Cys
                    85                 90                 95

Ala Arg Ser Thr Thr Val Ser Pro Pro His Leu Trp Gly Thr Gly Thr
                100                105                110

Thr Val Thr Val Ser Ser
            115

<210> SEQ ID NO 47
<211> LENGTH: 9
<212> TYPE: PRT
<213> ORGANISM: Artificial Sequence
<220> FEATURE:
<223> OTHER INFORMATION: affinity matured

<400> SEQUENCE: 47

Ser Thr Thr Val Ala Pro Pro Gly His
1               5

<210> SEQ ID NO 48
<211> LENGTH: 118
<212> TYPE: PRT
<213> ORGANISM: Artificial Sequence
<220> FEATURE:
<223> OTHER INFORMATION: affinity matured

<400> SEQUENCE: 48

Gln Val Gln Leu Val Gln Ser Gly Ala Glu Leu Lys Lys Pro Gly Ala
1               5                  10                 15

Ser Val Lys Leu Ser Cys Lys Ala Ser Gly Tyr Thr Phe Thr Ser Tyr
            20                 25                 30

Gly Ile Ser Trp Val Lys Gln Ala Thr Gly Gln Gly Leu Glu Trp Ile
            35                 40                 45

Gly Glu Ile Tyr Pro Arg Ser Gly Asn Thr Tyr Tyr Asn Glu Lys Phe
        50                 55                 60

Lys Gly Arg Ala Thr Leu Thr Ala Asp Lys Ser Thr Ser Thr Ala Tyr
65                      70                 75                 80

Met Glu Leu Arg Ser Leu Arg Ser Glu Asp Ser Ala Val Tyr Phe Cys
                    85                 90                 95

Ala Arg Ser Thr Thr Val Ala Pro Pro Gly His Trp Gly Thr Gly Thr
                100                105                110

Thr Val Thr Val Ser Ser
            115

<210> SEQ ID NO 49
<211> LENGTH: 9
<212> TYPE: PRT
<213> ORGANISM: Artificial Sequence
<220> FEATURE:
<223> OTHER INFORMATION: affinity matured

<400> SEQUENCE: 49
```

Ser Thr Thr Val Ser Pro Pro Arg Val
1               5

<210> SEQ ID NO 50
<211> LENGTH: 118
<212> TYPE: PRT
<213> ORGANISM: Artificial Sequence
<220> FEATURE:
<223> OTHER INFORMATION: affinity matured

<400> SEQUENCE: 50

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Ala Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Ser Pro Pro Arg Val Trp Gly Thr Gly Thr
            100                 105                 110

Thr Val Thr Val Ser Ser
        115

<210> SEQ ID NO 51
<211> LENGTH: 9
<212> TYPE: PRT
<213> ORGANISM: Artificial Sequence
<220> FEATURE:
<223> OTHER INFORMATION: affinity matured

<400> SEQUENCE: 51

Ser Thr Thr Val Ser Pro Pro Pro Leu
1               5

<210> SEQ ID NO 52
<211> LENGTH: 118
<212> TYPE: PRT
<213> ORGANISM: Artificial Sequence
<220> FEATURE:
<223> OTHER INFORMATION: affinity matured

<400> SEQUENCE: 52

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Ala Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Ser Pro Pro Leu Trp Gly Thr Gly Thr
            100                 105                 110

Thr Val Thr Val Ser Ser
        115

<210> SEQ ID NO 53
<211> LENGTH: 9
<212> TYPE: PRT
<213> ORGANISM: Artificial Sequence
<220> FEATURE:
<223> OTHER INFORMATION: affinity matured

<400> SEQUENCE: 53

Ser Thr Thr Val Ala Pro Pro Ala His
1               5

<210> SEQ ID NO 54
<211> LENGTH: 118
<212> TYPE: PRT
<213> ORGANISM: Artificial Sequence
<220> FEATURE:
<223> OTHER INFORMATION: affinity matured

<400> SEQUENCE: 54

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Ala Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Ala Pro Pro Ala His Trp Gly Thr Gly Thr
            100                 105                 110

Thr Val Thr Val Ser Ser
        115

<210> SEQ ID NO 55
<211> LENGTH: 9
<212> TYPE: PRT
<213> ORGANISM: Artificial Sequence
<220> FEATURE:
<223> OTHER INFORMATION: affinity matured

<400> SEQUENCE: 55

Ser Thr Thr Val Arg Pro Pro Gly Ile
1               5

<210> SEQ ID NO 56
<211> LENGTH: 118
<212> TYPE: PRT
<213> ORGANISM: Artificial Sequence
<220> FEATURE:
<223> OTHER INFORMATION: affinity matured

<400> SEQUENCE: 56

Gln Val Gln Leu Val Gln Ser Gly Ala Glu Leu Lys Lys Pro Gly Ala
1               5                   10                  15

```
Ser Val Lys Leu Ser Cys Lys Ala Ser Gly Tyr Thr Phe Thr Ser Tyr
            20                  25                  30

Gly Ile Ser Trp Val Lys Gln Ala Thr Gly Gln Gly Leu Glu Trp Ile
            35                  40                  45

Gly Glu Ile Tyr Pro Arg Ser Gly Asn Thr Tyr Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Arg Pro Pro Gly Ile Trp Gly Thr Gly Thr
            100                 105                 110

Thr Val Thr Val Ser Ser
        115
```

<210> SEQ ID NO 57
<211> LENGTH: 9
<212> TYPE: PRT
<213> ORGANISM: Artificial Sequence
<220> FEATURE:
<223> OTHER INFORMATION: affinity matured

<400> SEQUENCE: 57

```
Ser Thr Thr Val Ser Ala Pro Gly Val
1               5
```

<210> SEQ ID NO 58
<211> LENGTH: 118
<212> TYPE: PRT
<213> ORGANISM: Artificial Sequence
<220> FEATURE:
<223> OTHER INFORMATION: affinity matured

<400> SEQUENCE: 58

```
Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Ala Thr Gly Gln Gly Leu Glu Trp Ile
            35                  40                  45

Gly Glu Ile Tyr Pro Arg Ser Gly Asn Thr Tyr Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Glu Asp Ser Ala Val Tyr Phe Cys
                85                  90                  95

Ala Arg Ser Thr Thr Val Ser Ala Pro Gly Val Trp Gly Thr Gly Thr
            100                 105                 110

Thr Val Thr Val Ser Ser
        115
```

<210> SEQ ID NO 59
<211> LENGTH: 9
<212> TYPE: PRT
<213> ORGANISM: Artificial Sequence
<220> FEATURE:
<223> OTHER INFORMATION: affinity matured

```
<400> SEQUENCE: 59

Asn Thr Tyr Gly Asn Asn Pro His Thr
1               5

<210> SEQ ID NO 60
<211> LENGTH: 107
<212> TYPE: PRT
<213> ORGANISM: Artificial Sequence
<220> FEATURE:
<223> OTHER INFORMATION: affinity matured

<400> SEQUENCE: 60

Asp Ile Gln Met Thr Gln Ser Pro Ser Tyr Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys Asn Thr Tyr Gly Asn Asn Pro His
                85                  90                  95

Thr Phe Gly Gly Gly Thr Lys Val Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: affinity matured

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys Asn Thr Tyr Gly Asn Asn Pro His
                85                  90                  95

Thr Phe Gly Gly Gly Thr Lys Val Glu Ile Lys
            100                 105

<210> SEQ ID NO 62
<211> LENGTH: 9
<212> TYPE: PRT
<213> ORGANISM: Artificial Sequence
<220> FEATURE:
<223> OTHER INFORMATION: affinity matured

<400> SEQUENCE: 62

His Gln Tyr Tyr Asn Thr Pro Tyr Thr
1               5
```

```
<210> SEQ ID NO 63
<211> LENGTH: 107
<212> TYPE: PRT
<213> ORGANISM: Artificial Sequence
<220> FEATURE:
<223> OTHER INFORMATION: affinity matured

<400> SEQUENCE: 63

Asp Ile Gln Met Thr Gln Ser Pro Ser Tyr Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys His Gln Tyr Tyr Asn Thr Pro Tyr
                85                  90                  95

Thr Phe Gly Gly Gly Thr Lys Val Glu Ile Lys
            100                 105

<210> SEQ ID NO 64
<211> LENGTH: 107
<212> TYPE: PRT
<213> ORGANISM: Artificial Sequence
<220> FEATURE:
<223> OTHER INFORMATION: affinity matured

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys His Gln Tyr Tyr Asn Thr Pro Tyr
                85                  90                  95

Thr Phe Gly Gly Gly Thr Lys Val Glu Ile Lys
            100                 105

<210> SEQ ID NO 65
<211> LENGTH: 9
<212> TYPE: PRT
<213> ORGANISM: Artificial Sequence
<220> FEATURE:
<223> OTHER INFORMATION: affinity matured

<400> SEQUENCE: 65

His Gln Tyr Tyr Ser Thr Pro Tyr Thr
1               5

<210> SEQ ID NO 66
<211> LENGTH: 107
<212> TYPE: PRT
<213> ORGANISM: Artificial Sequence
```

<220> FEATURE:
<223> OTHER INFORMATION: affinity matured

<400> SEQUENCE: 66

Asp Ile Gln Met Thr Gln Ser Pro Ser Tyr Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys His Gln Tyr Tyr Ser Thr Pro Tyr
                85                  90                  95

Thr Phe Gly Gly Gly Thr Lys Val Glu Ile Lys
            100                 105

<210> SEQ ID NO 67
<211> LENGTH: 107
<212> TYPE: PRT
<213> ORGANISM: Artificial Sequence
<220> FEATURE:
<223> OTHER INFORMATION: affinity matured

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys His Gln Tyr Tyr Ser Thr Pro Tyr
                85                  90                  95

Thr Phe Gly Gly Gly Thr Lys Val Glu Ile Lys
            100                 105

<210> SEQ ID NO 68
<211> LENGTH: 9
<212> TYPE: PRT
<213> ORGANISM: Artificial Sequence
<220> FEATURE:
<223> OTHER INFORMATION: affinity matured

<400> SEQUENCE: 68

Gln Gln Tyr Tyr Ser Thr Pro Tyr Thr
1               5

<210> SEQ ID NO 69
<211> LENGTH: 107
<212> TYPE: PRT
<213> ORGANISM: Artificial Sequence
<220> FEATURE:
<223> OTHER INFORMATION: affinity matured

<400> SEQUENCE: 69

Asp Ile Gln Met Thr Gln Ser Pro Ser Tyr Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys Gln Gln Tyr Tyr Ser Thr Pro Tyr
                85                  90                  95

Thr Phe Gly Gly Gly Thr Lys Val Glu Ile Lys
            100                 105

<210> SEQ ID NO 70
<211> LENGTH: 107
<212> TYPE: PRT
<213> ORGANISM: Artificial Sequence
<220> FEATURE:
<223> OTHER INFORMATION: affinity matured

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
50                  55                  60

Ser Gly Thr Gly Lys Asp Tyr Thr Leu Thr Ile Ser Ser Leu Gln Thr
65                  70                  75                  80

Glu Asp Phe Ala Thr Tyr Tyr Cys Gln Gln Tyr Tyr Ser Thr Pro Tyr
                85                  90                  95

Thr Phe Gly Gly Gly Thr Lys Val Glu Ile Lys
            100                 105

<210> SEQ ID NO 71
<211> LENGTH: 21
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t

```
<220> FEATURE:
<221> NAME/KEY: misc_feature
<222> LOCATION: (16)..(16)
<223> OTHER INFORMATION: n is a, c, g, or t

<400> SEQUENCE: 71
kncnncnncn ncsvcnwcyg g                                              21

<210> SEQ ID NO 72
<211> LENGTH: 33
<212> TYPE: DNA
<213> ORGANISM: Artificial Sequence
<220> FEATURE:
<223> OTHER INFORMATION: synthetic sequence

<400> SEQUENCE: 72
tgtmrsvmgt vskrsrrcwm cyycbwcryc ttc                                 33

<210> SEQ ID NO 73
<211> LENGTH: 6
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (2)..(2)
<223> OTHER INFORMATION: residue is A R or S
<220> FEATURE:
<221> NAME/KEY: VARIANT
<222> LOCATION: (5)..(5)
<223> OTHER INFORMATION: residue is G or R
<220> FEATURE:
<221> NAME/KEY: VARIANT
<222> LOCATION: (6)..(6)
<223> OTHER INFORMATION: residue is I L or V

<400> SEQUENCE: 73

Val Xaa Pro Pro Xaa Xaa
1               5

<210> SEQ ID NO 74
<211> LENGTH: 9
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (5)..(5)
<223> OTHER INFORMATION: residue is A or R or S
<220> FEATURE:
<221> NAME/KEY: VARIANT
<222> LOCATION: (8)..(8)
<223> OTHER INFORMATION: residue is G or R
<220> FEATURE:
<221> NAME/KEY: VARIANT
<222> LOCATION: (9)..(9)
<223> OTHER INFORMATION: residue is I L or V

<400> SEQUENCE: 74

Ser Thr Thr Val Xaa Pro Pro Xaa Xaa
1               5

<210> SEQ ID NO 75
<211> LENGTH: 6
<212> TYPE: PRT
<213> ORGANISM: Artificial Sequence
<220> FEATURE:
<223> OTHER INFORMATION: consensus
```

```
<220> FEATURE:
<221> NAME/KEY: VARIANT
<222> LOCATION: (2)..(2)
<223> OTHER INFORMATION: residue is A R or S
<220> FEATURE:
<221> NAME/KEY: VARIANT
<222> LOCATION: (5)..(5)
<223> OTHER INFORMATION: residue is A G H P or R
<220> FEATURE:
<221> NAME/KEY: VARIANT
<222> LOCATION: (6)..(6)
<223> OTHER INFORMATION: residue is H I L or V

<400> SEQUENCE: 75

Val Xaa Pro Pro Xaa Xaa
1               5

<210> SEQ ID NO 76
<211> LENGTH: 9
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (5)..(5)
<223> OTHER INFORMATION: residue is A R or S
<220> FEATURE:
<221> NAME/KEY: VARIANT
<222> LOCATION: (8)..(8)
<223> OTHER INFORMATION: residue is A G H P or R
<220> FEATURE:
<221> NAME/KEY: VARIANT
<222> LOCATION: (9)..(9)
<223> OTHER INFORMATION: residue is H I L or V

<400> SEQUENCE: 76

Ser Thr Thr Val Xaa Pro Pro Xaa Xaa
1               5

<210> SEQ ID NO 77
<211> LENGTH: 6
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (2)..(2)
<223> OTHER INFORMATION: residue is A H R or S
<220> FEATURE:
<221> NAME/KEY: VARIANT
<222> LOCATION: (3)..(3)
<223> OTHER INFORMATION: residue is A or P
<220> FEATURE:
<221> NAME/KEY: VARIANT
<222> LOCATION: (3)..(4)
<223> OTHER INFORMATION: at least one of 3 and 4 is P
<220> FEATURE:
<221> NAME/KEY: VARIANT
<222> LOCATION: (4)..(4)
<223> OTHER INFORMATION: residue is A D or P
<220> FEATURE:
<221> NAME/KEY: VARIANT
<222> LOCATION: (5)..(5)
<223> OTHER INFORMATION: residue is A D G H P or R
<220> FEATURE:
<221> NAME/KEY: VARIANT
<222> LOCATION: (6)..(6)
<223> OTHER INFORMATION: residue is H I L or V
<220> FEATURE:
<221> NAME/KEY: VARIANT
<222> LOCATION: (6)..(6)
<223> OTHER INFORMATION: residue is F H I L N or V
```

<400> SEQUENCE: 77

Val Xaa Xaa Xaa Xaa
1               5

<210> SEQ ID NO 78
<211> LENGTH: 9
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (5)..(5)
<223> OTHER INFORMATION: residue is A H R or S
<220> FEATURE:
<221> NAME/KEY: VARIANT
<222> LOCATION: (6)..(6)
<223> OTHER INFORMATION: residue is A or P
<220> FEATURE:
<221> NAME/KEY: VARIANT
<222> LOCATION: (6)..(7)
<223> OTHER INFORMATION: at least one of 6 and 7 is P
<220> FEATURE:
<221> NAME/KEY: VARIANT
<222> LOCATION: (7)..(7)
<223> OTHER INFORMATION: residue is A D or P
<220> FEATURE:
<221> NAME/KEY: VARIANT
<222> LOCATION: (8)..(8)
<223> OTHER INFORMATION: residue is A D G H or P
<220> FEATURE:
<221> NAME/KEY: VARIANT
<222> LOCATION: (9)..(9)
<223> OTHER INFORMATION: residue is F H I L N or V

<400> SEQUENCE: 78

Ser Thr Thr Val Xaa Xaa Xaa Xaa Xaa
1               5

<210> SEQ ID NO 79
<211> LENGTH: 267
<212> TYPE: PRT
<213> ORGANISM: Homo sapiens

<400> SEQUENCE: 79

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
                20                  25                  30

Gln Gln Tyr Leu Ser Tyr Asn Ser Leu Arg Gly Glu Ala Glu Pro Cys
            35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

```
His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
            195                 200                 205

Gln Leu Arg Phe Leu Arg Asn Gly Leu Ala Ala Gly Thr Gly Gln Gly
            210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu
                260                 265

<210> SEQ ID NO 80
<211> LENGTH: 99
<212> TYPE: PRT
<213> ORGANISM: Homo sapiens

<400> SEQUENCE: 80

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
            35                  40                  45

Val Glu His Ser Asp Leu Ser Phe Ser Lys Asp Trp Ser Phe Tyr Leu
50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```

We claim:

1. An antibody or antigen-binding fragment thereof which binds to FcRn comprising a heavy chain variable region and a light chain variable region, wherein each of the heavy chain and the light chain variable regions comprises a CDR1, CDR2, and CDR3; and
wherein:
the sequence of CDR1 of the heavy chain is SEQ ID NO:2; and
the sequence of CDR2 of the heavy chain is SEQ ID NO:4; and
the sequence of CDR3 of the heavy chain is SEQ ID NO:55; and
the sequence of CDR1 of the light chain is SEQ ID NO:6; and
the sequence of CDR2 of the light chain is SEQ ID NO:8; and
the sequence of CDR3 of the light chain is SEQ ID NO:10.

2. The antibody or antigen-binding fragment of claim 1, wherein the sequence of the heavy chain variable region is SEQ ID NO:56, and wherein the sequence of the light chain variable region is SEQ ID NO:22.

* * * * *